United States Patent
Singh et al.

(10) Patent No.: US 12,129,310 B2
(45) Date of Patent: Oct. 29, 2024

(54) MATERIALS AND METHODS FOR ENHANCED LINKER TARGETING

(71) Applicant: Janssen Biotech, Inc., Horsham, PA (US)

(72) Inventors: Sanjaya Singh, Blue Bell, PA (US); Rajkumar Ganesan, Blue Bell, PA (US); Jun Chen, New Hope, PA (US); Iqbal S. Grewal, Newton, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 41 days.

(21) Appl. No.: 18/122,948

(22) Filed: Mar. 17, 2023

(65) Prior Publication Data

US 2023/0374156 A1   Nov. 23, 2023

Related U.S. Application Data

(62) Division of application No. 17/672,471, filed on Feb. 15, 2022, now Pat. No. 11,639,396.

(60) Provisional application No. 63/149,872, filed on Feb. 16, 2021, provisional application No. 63/149,892, filed on Feb. 16, 2021, provisional application No. 63/149,883, filed on Feb. 16, 2021, provisional application No. 63/149,865, filed on Feb. 16, 2021, provisional application No. 63/149,857, filed on Feb. 16, 2021.

(51) Int. Cl.
  *C07K 16/42*  (2006.01)
  *G01N 33/68*  (2006.01)

(52) U.S. Cl.
  CPC .......... *C07K 16/42* (2013.01); *G01N 33/6857* (2013.01); *C07K 2317/14* (2013.01); *C07K 2317/34* (2013.01)

(58) Field of Classification Search
  None
  See application file for complete search history.

(56) References Cited

FOREIGN PATENT DOCUMENTS

| WO | 199515982 A2 | 6/1995 |
|----|--------------|--------|
| WO | 2021019386 A1 | 2/2021 |

OTHER PUBLICATIONS

International Search Report and Written Opinion mailed Jul. 11, 2022 in connection with PCT/US22/016454.
Bryan N. et al., "Differential splicing of the apoptosis-associated speck like protein containing a caspase inflammasomes" Journal of Inflammation, Biomed Central, London, GB, vol. 7, No. 1, May 10, 2010, p. 23.
Jones G. et al., "Variable linking region immunogenicity using malarial peptide carrier protein conjungates of defined compositions" Immunology Letters, Elsevier BV, NL, vol. 26, No. 3, Dec. 1, 1990, pp. 285-290.
Office Action issued Aug. 26, 2022 in connection with U.S. Appl. No. 17/672,471.
Schroeder et al. (J Allergy Clin Immunol 2010, 125:S41-S52).
Lloyd et al. (Protein Engineering, Design & Selection 2009, 22:159-168).
Rudikoff et al. (Proc Natl Acad Sci USA 1982 vol. 79 p. 1979).
Maccallum et al. (J. Mol. Biol. 1996 262, 732-7 45).
Pascalis et al. (The Journal of Immunology (2002) 169, 3076-3084).
Gasset et al. (BBRC 2003, 307:198-205).
Vajdos et al. (J. Mol. Biol. (2002) 320, 415-428).
Chen etal. (J. Mol. Bio. (1999) 293, 865-881).
Wu et al. (J. Mol. Biol. (1999) 294, 151-162).
Padlan et al. (PNAS 1989, 86:5938-5942).
Lamminmaki et al. (JBC 2001, 276:36687-36694).
Piche-Nicholas etal. MABS 2018, 10:81-94.

*Primary Examiner* — Sharon X Wen

(74) *Attorney, Agent, or Firm* — Arnold & Porter Kaye Scholer

(57) ABSTRACT

Molecules, including antibodies and antigen-binding fragments thereof that specifically bind to a linker peptide, and methods of producing and using the described antibodies and antigen-binding fragments are presented herein. Also presented herein methods of generating antibodies that specifically bind to an immunorecessive epitope.

16 Claims, 18 Drawing Sheets

Specification includes a Sequence Listing.

MATERIALS AND METHODS FOR ENHANCED LINKER TARGETING

CROSS REFERENCE TO RELATED APPLICATIONS

This patent application is a divisional of U.S. patent application Ser. No. 17/672,471, filed Feb. 15, 2022, which claims priority to U.S. Provisional Application No. 63/149,857, filed Feb. 16, 2021, U.S. Provisional Application No. 63/149,865, filed Feb. 16, 2021, U.S. Provisional Application No. 63/149,872, filed Feb. 16, 2021, U.S. Provisional Application No. 63/149,883, filed Feb. 16, 2021, and U.S. Provisional Application No. 63/149,892, filed Feb. 16, 2021, the disclosure of each of which is herein incorporated by reference in its entirety.

SEQUENCE LISTING

The instant application contains a Sequence Listing which has been submitted electronically in XML format and is hereby incorporated by reference in its entirety. Said XML copy, created on Apr. 4, 2023, is named 253505_000169_SL.xml and is 116,843 bytes in size.

FIELD OF THE INVENTION

The disclosure provided herein relates to molecules, such as antibodies and antigen-binding fragments, that specifically bind to a linker peptide, and methods of producing and using same. The disclosure provided herein also relates to methods of generating such molecules, including antibodies, that specifically bind to an immunorecessive epitope.

BACKGROUND

A polypeptide linker termed MSCD331 (GGSEGKSSGSGSESKSTGGS; SEQ ID NO: 98) is routinely used to genetically fuse different heavy chain variable (VH) and light chain variable (VL) regions to form single-chain variable fragment (scFv) molecules. These scFv molecules can subsequently be part of a bispecific antibody or a chimeric antigen receptor (CAR) on engineered immune cells and cell lines. Hence, monoclonal antibodies (mAbs) with high specificity against the MSCD331 linker could serve as an essential tool reagent in biological measurement and molecular modelling of scFvs, bispecific antibodies, and CARs.

There is relatively limited availability of monospecific antisera and mAbs against linker peptides. This is attributed to, for example, poor immunogenicity of linker peptides. One strategy in such cases has been to couple the peptide to larger carrier proteins that have good immunogenicity. However, the immune response to the linker peptide is often masked by the overwhelming response to the carrier protein, thereby hindering the development of anti-linker specific monoclones.

SUMMARY OF THE INVENTION

Accordingly, there is a need for antibodies with high specificity against the MSCD331 linker as well as improved methods for generating antibodies that specifically bind to an immunorecessive epitope such as a linker peptide, which is met by the present invention.

In one aspect, provided herein is an isolated antibody, or antigen-binding fragment thereof, that specifically binds to a linker peptide comprising the amino acid sequence of GGSEGKSSGSGSESKSTGGS (SEQ ID NO: 98).

In some embodiments, the isolated antibody, or antigen-binding fragment thereof, specifically binds to a linker peptide consisting of the amino acid sequence of GGSEGKSSGSGSESKSTGGS (SEQ ID NO: 98).

In some embodiments, the isolated antibody, or antigen-binding fragment thereof, comprises
a heavy chain complementarity determining region 1 (CDR1), a heavy chain CDR2, and a heavy chain CDR3 of a heavy chain variable region (VH) comprising an amino acid sequence of SEQ ID NO: 21, 23, 27, 29, 31, 33, 35, 37, 39, 41, 43, 45, or 47, or a sequence having at least 80% identity thereto; and/or
a light chain CDR1, a light chain CDR2, and a light chain CDR3 of a light chain variable region (VL) comprising an amino acid sequence of SEQ ID NO: 68, 70, 72, 74, 76, 78, 80, 82, 84, 86, 88, 90, 92, 94, or 96, or a sequence having at least 80% identity thereto.

In some embodiments, the isolated antibody, or antigen-binding fragment thereof, comprises
a heavy chain CDR1, a heavy chain CDR2 and a heavy chain CDR3 of a VH comprising an amino acid sequence of SEQ ID NO: 21, and a light chain CDR1, a light chain CDR2 and a light chain CDR3 of a VL comprising an amino acid sequence of SEQ ID NO: 80;
a heavy chain CDR1, a heavy chain CDR2 and a heavy chain CDR3 of a VH comprising an amino acid sequence of SEQ ID NO: 23, and a light chain CDR1, a light chain CDR2 and a light chain CDR3 of a VL comprising an amino acid sequence of SEQ ID NO: 74;
a heavy chain CDR1, a heavy chain CDR2 and a heavy chain CDR3 of a VH comprising an amino acid sequence of SEQ ID NO: 25, and a light chain CDR1, a light chain CDR2 and a light chain CDR3 of a VL comprising an amino acid sequence of SEQ ID NO: 74;
a heavy chain CDR1, a heavy chain CDR2 and a heavy chain CDR3 of a VH comprising an amino acid sequence of SEQ ID NO: 27, and a light chain CDR1, a light chain CDR2 and a light chain CDR3 of a VL comprising an amino acid sequence of SEQ ID NO: 72;
a heavy chain CDR1, a heavy chain CDR2 and a heavy chain CDR3 of a VH comprising an amino acid sequence of SEQ ID NO: 29, and a light chain CDR1, a light chain CDR2 and a light chain CDR3 of a VL comprising an amino acid sequence of SEQ ID NO: 74;
a heavy chain CDR1, a heavy chain CDR2 and a heavy chain CDR3 of a VH comprising an amino acid sequence of SEQ ID NO: 29, and a light chain CDR1, a light chain CDR2 and a light chain CDR3 of a VL comprising an amino acid sequence of SEQ ID NO: 96;
a heavy chain CDR1, a heavy chain CDR2 and a heavy chain CDR3 of a VH comprising an amino acid sequence of SEQ ID NO: 29, and a light chain CDR1, a light chain CDR2 and a light chain CDR3 of a VL comprising an amino acid sequence of SEQ ID NO: 76;
a heavy chain CDR1, a heavy chain CDR2 and a heavy chain CDR3 of a VH comprising an amino acid sequence of SEQ ID NO: 29, and a light chain CDR1, a light chain CDR2 and a light chain CDR3 of a VL comprising an amino acid sequence of SEQ ID NO: 72;
a heavy chain CDR1, a heavy chain CDR2 and a heavy chain CDR3 of a VH comprising an amino acid sequence of SEQ ID NO: 31, and a light chain CDR1, a light chain CDR2 and a light chain CDR3 of a VL comprising an amino acid sequence of SEQ ID NO: 74;

a heavy chain CDR1, a heavy chain CDR2 and a heavy chain CDR3 of a VH comprising an amino acid sequence of SEQ ID NO: 33, and a light chain CDR1, a light chain CDR2 and a light chain CDR3 of a VL comprising an amino acid sequence of SEQ ID NO: 70;

a heavy chain CDR1, a heavy chain CDR2 and a heavy chain CDR3 of a VH comprising an amino acid sequence of SEQ ID NO: 33, and a light chain CDR1, a light chain CDR2 and a light chain CDR3 of a VL comprising an amino acid sequence of SEQ ID NO: 94;

a heavy chain CDR1, a heavy chain CDR2 and a heavy chain CDR3 of a VH comprising an amino acid sequence of SEQ ID NO: 35, and a light chain CDR1, a light chain CDR2 and a light chain CDR3 of a VL comprising an amino acid sequence of SEQ ID NO: 70;

a heavy chain CDR1, a heavy chain CDR2 and a heavy chain CDR3 of a VH comprising an amino acid sequence of SEQ ID NO: 37, and a light chain CDR1, a light chain CDR2 and a light chain CDR3 of a VL comprising an amino acid sequence of SEQ ID NO: 76;

a heavy chain CDR1, a heavy chain CDR2 and a heavy chain CDR3 of a VH comprising an amino acid sequence of SEQ ID NO: 37, and a light chain CDR1, a light chain CDR2 and a light chain CDR3 of a VL comprising an amino acid sequence of SEQ ID NO: 78;

a heavy chain CDR1, a heavy chain CDR2 and a heavy chain CDR3 of a VH comprising an amino acid sequence of SEQ ID NO: 37, and a light chain CDR1, a light chain CDR2 and a light chain CDR3 of a VL comprising an amino acid sequence of SEQ ID NO: 82;

a heavy chain CDR1, a heavy chain CDR2 and a heavy chain CDR3 of a VH comprising an amino acid sequence of SEQ ID NO: 37, and a light chain CDR1, a light chain CDR2 and a light chain CDR3 of a VL comprising an amino acid sequence of SEQ ID NO: 84;

a heavy chain CDR1, a heavy chain CDR2 and a heavy chain CDR3 of a VH comprising an amino acid sequence of SEQ ID NO: 37, and a light chain CDR1, a light chain CDR2 and a light chain CDR3 of a VL comprising an amino acid sequence of SEQ ID NO: 72;

a heavy chain CDR1, a heavy chain CDR2 and a heavy chain CDR3 of a VH comprising an amino acid sequence of SEQ ID NO: 39, and a light chain CDR1, a light chain CDR2 and a light chain CDR3 of a VL comprising an amino acid sequence of SEQ ID NO: 76;

a heavy chain CDR1, a heavy chain CDR2 and a heavy chain CDR3 of a VH comprising an amino acid sequence of SEQ ID NO: 41, and a light chain CDR1, a light chain CDR2 and a light chain CDR3 of a VL comprising an amino acid sequence of SEQ ID NO: 92;

a heavy chain CDR1, a heavy chain CDR2 and a heavy chain CDR3 of a VH comprising an amino acid sequence of SEQ ID NO: 41, and a light chain CDR1, a light chain CDR2 and a light chain CDR3 of a VL comprising an amino acid sequence of SEQ ID NO: 68;

a heavy chain CDR1, a heavy chain CDR2 and a heavy chain CDR3 of a VH comprising an amino acid sequence of SEQ ID NO: 43, and a light chain CDR1, a light chain CDR2 and a light chain CDR3 of a VL comprising an amino acid sequence of SEQ ID NO: 86;

a heavy chain CDR1, a heavy chain CDR2 and a heavy chain CDR3 of a VH comprising an amino acid sequence of SEQ ID NO: 45, and a light chain CDR1, a light chain CDR2 and a light chain CDR3 of a VL comprising an amino acid sequence of SEQ ID NO: 88; or a heavy chain CDR1, a heavy chain CDR2 and a heavy chain CDR3 of a VH comprising an amino acid sequence of SEQ ID NO: 47, and a light chain CDR1, a light chain CDR2 and a light chain CDR3 of a VL comprising an amino acid sequence of SEQ ID NO: 90.

In some embodiments, the isolated antibody, or antigen-binding fragment thereof, comprises a heavy chain complementarity determining region 1 (CDR1) comprising the amino acid sequence of SEQ ID NO: 1, a heavy chain CDR2 comprising the amino acid sequence of SEQ ID NO: 2, and a heavy chain CDR3 comprising the amino acid sequence of SEQ ID NO: 3;

a heavy chain CDR1 comprising the amino acid sequence of SEQ ID NO: 4, a heavy chain CDR2 comprising the amino acid sequence of SEQ ID NO: 5, and a heavy chain CDR3 comprising the amino acid sequence of SEQ ID NO: 3;

a heavy chain CDR1 comprising the amino acid sequence of SEQ ID NO: 7, a heavy chain CDR2 comprising the amino acid sequence of SEQ ID NO: 8, and a heavy chain CDR3 comprising the amino acid sequence of SEQ ID NO: 9;

a heavy chain CDR1 comprising the amino acid sequence of SEQ ID NO: 10, a heavy chain CDR2 comprising the amino acid sequence of SEQ ID NO: 8, and a heavy chain CDR3 comprising the amino acid sequence of SEQ ID NO: 9;

a heavy chain CDR1 comprising the amino acid sequence of SEQ ID NO: 11, a heavy chain CDR2 comprising the amino acid sequence of SEQ ID NO: 12, and a heavy chain CDR3 comprising the amino acid sequence of SEQ ID NO: 13;

a heavy chain CDR1 comprising the amino acid sequence of SEQ ID NO: 11, a heavy chain CDR2 comprising the amino acid sequence of SEQ ID NO: 14, and a heavy chain CDR3 comprising the amino acid sequence of SEQ ID NO: 15;

a heavy chain CDR1 comprising the amino acid sequence of SEQ ID NO: 16, a heavy chain CDR2 comprising the amino acid sequence of SEQ ID NO: 17, and a heavy chain CDR3 comprising the amino acid sequence of SEQ ID NO: 18; or a heavy chain CDR1 comprising the amino acid sequence of SEQ ID NO: 19, a heavy chain CDR2 comprising the amino acid sequence of SEQ ID NO: 8, and a heavy chain CDR3 comprising the amino acid sequence of SEQ ID NO: 20.

In some embodiments, the isolated antibody or antigen-binding fragment comprises a light chain CDR1 comprising the amino acid sequence of SEQ ID NO: 49, a light chain CDR2 comprising the amino acid sequence of SEQ ID NO: 50, and a light chain CDR3 comprising the amino acid sequence of SEQ ID NO: 51;

a light chain CDR1 comprising the amino acid sequence of SEQ ID NO: 52, a light chain CDR2 comprising the amino acid sequence of SEQ ID NO: 50, and a light chain CDR3 comprising the amino acid sequence of SEQ ID NO: 54;

a light chain CDR1 comprising the amino acid sequence of SEQ ID NO: 52, a light chain CDR2 comprising the amino acid sequence of SEQ ID NO: 53, and a light chain CDR3 comprising the amino acid sequence of SEQ ID NO: 54;

a light chain CDR1 comprising the amino acid sequence of SEQ ID NO: 49, a light chain CDR2 comprising the amino acid sequence of SEQ ID NO: 50, and a light chain CDR3 comprising the amino acid sequence of SEQ ID NO: 57;
- a light chain CDR1 comprising the amino acid sequence of SEQ ID NO: 55, a light chain CDR2 comprising the amino acid sequence of SEQ ID NO: 56, and a light chain CDR3 comprising the amino acid sequence of SEQ ID NO: 60;
- a light chain CDR1 comprising the amino acid sequence of SEQ ID NO: 58, a light chain CDR2 comprising the amino acid sequence of SEQ ID NO: 50, and a light chain CDR3 comprising the amino acid sequence of SEQ ID NO: 51;
- a light chain CDR1 comprising the amino acid sequence of SEQ ID NO: 61, a light chain CDR2 comprising the amino acid sequence of SEQ ID NO: 59, and a light chain CDR3 comprising the amino acid sequence of SEQ ID NO: 63;
- a light chain CDR1 comprising the amino acid sequence of SEQ ID NO: 64, a light chain CDR2 comprising the amino acid sequence of SEQ ID NO: 56, and a light chain CDR3 comprising the amino acid sequence of SEQ ID NO: 65; or
- a light chain CDR1 comprising the amino acid sequence of SEQ ID NO: 66, a light chain CDR2 comprising the amino acid sequence of SEQ ID NO: 62, and a light chain CDR3 comprising the amino acid sequence of SEQ ID NO: 67.

In some embodiments, the isolated antibody or antigen-binding fragment comprises the heavy chain CDR1, the heavy chain CDR2, the heavy chain CDR3, the light chain CDR1, the light chain CDR2 and the light chain CDR3 comprising the amino acid sequence of
- a) SEQ ID NOs: 1, 2, 3, 49, 50, and 57, respectively;
- b) SEQ ID NOs: 4, 5, 3, 49, 50, and 57, respectively;
- c) SEQ ID NOs: 7, 8, 9, 52, 53, and 54, respectively;
- d) SEQ ID NOs: 7, 8, 9, 49, 50, and 57, respectively;
- e) SEQ ID NOs: 7, 8, 9, 66, 62, and 67, respectively;
- f) SEQ ID NOs: 10, 8, 9, 52, 50, and 54, respectively;
- g) SEQ ID NOs: 10, 8, 9, 52, 53, and 54, respectively;
- h) SEQ ID NOs: 10, 8, 9, 64, 56, and 65, respectively;
- i) SEQ ID NOs: 10, 8, 9, 55, 56, and 60, respectively;
- j) SEQ ID NOs: 11, 12, 13, 49, 50, and 51, respectively;
- k) SEQ ID NOs: 11, 14, 15, 58, 50, and 51, respectively;
- l) SEQ ID NOs: 16, 17, 18, 61, 59, and 63, respectively; or
- m) SEQ ID NOs: 19, 8, 20, 49, 50, and 51, respectively.

In some embodiments, the isolated antibody or antigen-binding fragment comprises
- a heavy chain variable region (VH) comprising an amino acid sequence of SEQ ID NO: 21, 23, 25, 27, 29, 31, 33, 35, 37, 39, 41, 43, 45, or 47, or a sequence having at least 80% identity thereto; and/or
- a light chain variable region (VL) comprising an amino acid sequence of SEQ ID NO: 68, 70, 72, 74, 76, 78, 80, 82, 84, 86, 88, 90, 92, 94, or 96, or a sequence having at least 80% identity thereto.

In some embodiments, the isolated antibody or antigen-binding fragment comprises
- a heavy chain variable region (VH) comprising an amino acid sequence encoded by a nucleotide sequence of SEQ ID NO: 22, 24, 26, 28, 30, 32, 34, 36, 38, 40, 42, 44, 46, or 48, or a sequence having at least 80% identity thereto; and/or
- a light chain variable region (VL) comprising an amino acid sequence encoded by a nucleotide sequence of SEQ ID NO: 69, 71, 73, 75, 77, 79, 81, 83, 85, 87, 89, 91, 93, 95, or 97, or a sequence having at least 80% identity thereto.

In some embodiments, the isolated antibody or antigen-binding fragment comprises
- a heavy chain variable region comprising an amino acid sequence of SEQ ID NO: 21, or a sequence having at least 80% identity thereto, and a light chain variable region comprising an amino acid sequence of SEQ ID NO: 80, or a sequence having at least 80% identity thereto;
- a heavy chain variable region comprising an amino acid sequence of SEQ ID NO: 23, or a sequence having at least 80% identity thereto, and a light chain variable region comprising an amino acid sequence of SEQ ID NO: 74, or a sequence having at least 80% identity thereto;
- a heavy chain variable region comprising an amino acid sequence of SEQ ID NO: 25, or a sequence having at least 80% identity thereto, and a light chain variable region comprising an amino acid sequence of SEQ ID NO: 74, or a sequence having at least 80% identity thereto;
- a heavy chain variable region comprising an amino acid sequence of SEQ ID NO: 27, or a sequence having at least 80% identity thereto, and a light chain variable region comprising an amino acid sequence of SEQ ID NO: 72, or a sequence having at least 80% identity thereto;
- a heavy chain variable region comprising an amino acid sequence of SEQ ID NO: 29, or a sequence having at least 80% identity thereto, and a light chain variable region comprising an amino acid sequence of SEQ ID NO: 74, or a sequence having at least 80% identity thereto;
- a heavy chain variable region comprising an amino acid sequence of SEQ ID NO: 29, or a sequence having at least 80% identity thereto, and a light chain variable region comprising an amino acid sequence of SEQ ID NO: 96, or a sequence having at least 80% identity thereto;
- a heavy chain variable region comprising an amino acid sequence of SEQ ID NO: 29, or a sequence having at least 80% identity thereto, and a light chain variable region comprising an amino acid sequence of SEQ ID NO: 76, or a sequence having at least 80% identity thereto;
- a heavy chain variable region comprising an amino acid sequence of SEQ ID NO: 29, or a sequence having at least 80% identity thereto, and a light chain variable region comprising an amino acid sequence of SEQ ID NO: 72, or a sequence having at least 80% identity thereto;
- a heavy chain variable region comprising an amino acid sequence of SEQ ID NO: 31, or a sequence having at least 80% identity thereto, and a light chain variable region comprising an amino acid sequence of SEQ ID NO: 74, or a sequence having at least 80% identity thereto;
- a heavy chain variable region comprising an amino acid sequence of SEQ ID NO: 33, or a sequence having at least 80% identity thereto, and a light chain variable region comprising an amino acid sequence of SEQ ID NO: 70, or a sequence having at least 80% identity thereto;
- a heavy chain variable region comprising an amino acid sequence of SEQ ID NO: 33, or a sequence having at least 80% identity thereto, and a light chain variable region comprising an amino acid sequence of SEQ ID NO: 94, or a sequence having at least 80% identity thereto;

a heavy chain variable region comprising an amino acid sequence of SEQ ID NO: 35, or a sequence having at least 80% identity thereto, and a light chain variable region comprising an amino acid sequence of SEQ ID NO: 70, or a sequence having at least 80% identity thereto;

a heavy chain variable region comprising an amino acid sequence of SEQ ID NO: 37, or a sequence having at least 80% identity thereto, and a light chain variable region comprising an amino acid sequence of SEQ ID NO: 76, or a sequence having at least 80% identity thereto;

a heavy chain variable region comprising an amino acid sequence of SEQ ID NO: 37, or a sequence having at least 80% identity thereto, and a light chain variable region comprising an amino acid sequence of SEQ ID NO: 78, or a sequence having at least 80% identity thereto;

a heavy chain variable region comprising an amino acid sequence of SEQ ID NO: 37, or a sequence having at least 80% identity thereto, and a light chain variable region comprising an amino acid sequence of SEQ ID NO: 82, or a sequence having at least 80% identity thereto;

a heavy chain variable region comprising an amino acid sequence of SEQ ID NO: 37, or a sequence having at least 80% identity thereto, and a light chain variable region comprising an amino acid sequence of SEQ ID NO: 84, or a sequence having at least 80% identity thereto;

a heavy chain variable region comprising an amino acid sequence of SEQ ID NO: 37, or a sequence having at least 80% identity thereto, and a light chain variable region comprising an amino acid sequence of SEQ ID NO: 72, or a sequence having at least 80% identity thereto;

a heavy chain variable region comprising an amino acid sequence of SEQ ID NO: 39, or a sequence having at least 80% identity thereto, and a light chain variable region comprising an amino acid sequence of SEQ ID NO: 76, or a sequence having at least 80% identity thereto;

a heavy chain variable region comprising an amino acid sequence of SEQ ID NO: 41, or a sequence having at least 80% identity thereto, and a light chain variable region comprising an amino acid sequence of SEQ ID NO: 92, or a sequence having at least 80% identity thereto;

a heavy chain variable region comprising an amino acid sequence of SEQ ID NO: 41, or a sequence having at least 80% identity thereto, and a light chain variable region comprising an amino acid sequence of SEQ ID NO: 68, or a sequence having at least 80% identity thereto;

a heavy chain variable region comprising an amino acid sequence of SEQ ID NO: 43, or a sequence having at least 80% identity thereto, and a light chain variable region comprising an amino acid sequence of SEQ ID NO: 86, or a sequence having at least 80% identity thereto;

a heavy chain variable region comprising an amino acid sequence of SEQ ID NO: 45, or a sequence having at least 80% identity thereto, and a light chain variable region comprising an amino acid sequence of SEQ ID NO: 88, or a sequence having at least 80% identity thereto; or a heavy chain variable region comprising an amino acid sequence of SEQ ID NO: 47, or a sequence having at least 80% identity thereto, and a light chain variable region comprising an amino acid sequence of SEQ ID NO: 90, or a sequence having at least 80% identity thereto.

In some embodiments, the isolated antibody or antigen-binding fragment comprises a heavy chain variable region comprising an amino acid sequence encoded by the nucleotide sequence of SEQ ID NO: 22, or a sequence having at least 80% identity thereto, and a light chain variable region comprising an amino acid sequence encoded by the nucleotide sequence of SEQ ID NO: 81, or a sequence having at least 80% identity thereto;

a heavy chain variable region comprising an amino acid sequence encoded by the nucleotide sequence of SEQ ID NO: 24, or a sequence having at least 80% identity thereto, and a light chain variable region comprising an amino acid sequence encoded by the nucleotide sequence of SEQ ID NO: 75, or a sequence having at least 80% identity thereto;

a heavy chain variable region comprising an amino acid sequence encoded by the nucleotide sequence of SEQ ID NO: 26, or a sequence having at least 80% identity thereto, and a light chain variable region comprising an amino acid sequence encoded by the nucleotide sequence of SEQ ID NO: 75, or a sequence having at least 80% identity thereto;

a heavy chain variable region comprising an amino acid sequence encoded by the nucleotide sequence of SEQ ID NO: 28, or a sequence having at least 80% identity thereto, and a light chain variable region comprising an amino acid sequence encoded by the nucleotide sequence of SEQ ID NO: 73, or a sequence having at least 80% identity thereto;

a heavy chain variable region comprising an amino acid sequence encoded by the nucleotide sequence of SEQ ID NO: 30, or a sequence having at least 80% identity thereto, and a light chain variable region comprising an amino acid sequence encoded by the nucleotide sequence of SEQ ID NO: 75, or a sequence having at least 80% identity thereto;

a heavy chain variable region comprising an amino acid sequence encoded by the nucleotide sequence of SEQ ID NO: 30, or a sequence having at least 80% identity thereto, and a light chain variable region comprising an amino acid sequence encoded by the nucleotide sequence of SEQ ID NO: 97, or a sequence having at least 80% identity thereto;

a heavy chain variable region comprising an amino acid sequence encoded by the nucleotide sequence of SEQ ID NO: 30, or a sequence having at least 80% identity thereto, and a light chain variable region comprising an amino acid sequence encoded by the nucleotide sequence of SEQ ID NO: 77, or a sequence having at least 80% identity thereto;

a heavy chain variable region comprising an amino acid sequence encoded by the nucleotide sequence of SEQ ID NO: 30, or a sequence having at least 80% identity thereto, and a light chain variable region comprising an amino acid sequence encoded by the nucleotide sequence of SEQ ID NO: 73, or a sequence having at least 80% identity thereto;

a heavy chain variable region comprising an amino acid sequence encoded by the nucleotide sequence of SEQ ID NO: 32, or a sequence having at least 80% identity thereto, and a light chain variable region comprising an amino acid sequence encoded by the nucleotide sequence of SEQ ID NO: 75, or a sequence having at least 80% identity thereto;

a heavy chain variable region comprising an amino acid sequence encoded by the nucleotide sequence of SEQ ID NO: 34, or a sequence having at least 80% identity thereto, and a light chain variable region comprising an amino acid sequence encoded by the nucleotide sequence of SEQ ID NO: 71, or a sequence having at least 80% identity thereto;

a heavy chain variable region comprising an amino acid sequence encoded by the nucleotide sequence of SEQ ID NO: 34, or a sequence having at least 80% identity thereto, and a light chain variable region comprising an amino acid sequence encoded by the nucleotide sequence of SEQ ID NO: 95, or a sequence having at least 80% identity thereto;

a heavy chain variable region comprising an amino acid sequence encoded by the nucleotide sequence of SEQ ID NO: 36, or a sequence having at least 80% identity thereto, and a light chain variable region comprising an amino acid sequence encoded by the nucleotide sequence of SEQ ID NO: 71, or a sequence having at least 80% identity thereto;

a heavy chain variable region comprising an amino acid sequence encoded by the nucleotide sequence of SEQ ID NO: 38, or a sequence having at least 80% identity thereto, and a light chain variable region comprising an amino acid sequence encoded by the nucleotide sequence of SEQ ID NO: 77, or a sequence having at least 80% identity thereto;

a heavy chain variable region comprising an amino acid sequence encoded by the nucleotide sequence of SEQ ID NO: 38, or a sequence having at least 80% identity thereto, and a light chain variable region comprising an amino acid sequence encoded by the nucleotide sequence of SEQ ID NO: 79, or a sequence having at least 80% identity thereto;

a heavy chain variable region comprising an amino acid sequence encoded by the nucleotide sequence of SEQ ID NO: 38, or a sequence having at least 80% identity thereto, and a light chain variable region comprising an amino acid sequence encoded by the nucleotide sequence of SEQ ID NO: 83, or a sequence having at least 80% identity thereto;

a heavy chain variable region comprising an amino acid sequence encoded by the nucleotide sequence of SEQ ID NO: 38, or a sequence having at least 80% identity thereto, and a light chain variable region comprising an amino acid sequence encoded by the nucleotide sequence of SEQ ID NO: 85, or a sequence having at least 80% identity thereto;

a heavy chain variable region comprising an amino acid sequence encoded by the nucleotide sequence of SEQ ID NO: 38, or a sequence having at least 80% identity thereto, and a light chain variable region comprising an amino acid sequence encoded by the nucleotide sequence of SEQ ID NO: 73, or a sequence having at least 80% identity thereto;

a heavy chain variable region comprising an amino acid sequence encoded by the nucleotide sequence of SEQ ID NO: 40, or a sequence having at least 80% identity thereto, and a light chain variable region comprising an amino acid sequence encoded by the nucleotide sequence of SEQ ID NO: 77, or a sequence having at least 80% identity thereto;

a heavy chain variable region comprising an amino acid sequence encoded by the nucleotide sequence of SEQ ID NO: 42, or a sequence having at least 80% identity thereto, and a light chain variable region comprising an amino acid sequence encoded by the nucleotide sequence of SEQ ID NO: 93, or a sequence having at least 80% identity thereto;

a heavy chain variable region comprising an amino acid sequence encoded by the nucleotide sequence of SEQ ID NO: 42, or a sequence having at least 80% identity thereto, and a light chain variable region comprising an amino acid sequence encoded by the nucleotide sequence of SEQ ID NO: 69, or a sequence having at least 80% identity thereto;

a heavy chain variable region comprising an amino acid sequence encoded by the nucleotide sequence of SEQ ID NO: 44, or a sequence having at least 80% identity thereto, and a light chain variable region comprising an amino acid sequence encoded by the nucleotide sequence of SEQ ID NO: 87, or a sequence having at least 80% identity thereto;

a heavy chain variable region comprising an amino acid sequence encoded by the nucleotide sequence of SEQ ID NO: 46, or a sequence having at least 80% identity thereto, and a light chain variable region comprising an amino acid sequence encoded by the nucleotide sequence of SEQ ID NO: 89, or a sequence having at least 80% identity thereto; or a heavy chain variable region comprising an amino acid sequence encoded by the nucleotide sequence of SEQ ID NO: 48, or a sequence having at least 80% identity thereto, and a light chain variable region comprising an amino acid sequence encoded by the nucleotide sequence of SEQ ID NO: 91, or a sequence having at least 80% identity thereto.

In some embodiments, the isolated antibody or antigen-binding fragment does not specifically bind to the amino acid sequence GGGGSGGGGSGGGGSGGGGS (SEQ ID NO: 99).

In some embodiments, the isolated antibody or antigen-binding fragment does not specifically bind to Immunoglobulin G (IgG).

In some embodiments, the isolated antibody or antigen-binding fragment is recombinant.

In some embodiments, the isolated antibody or antigen-binding fragment is a human antibody, a monoclonal antibody, a single chain antibody, a Fab, a Fab', a F(ab')2, a Fv, or a scFv.

In some embodiments, the isolated antibody or antigen-binding fragment is of IgG1, IgG2, IgG3, or IgG4 isotype.

In another aspect, provided herein is an isolated polynucleotide encoding the isolated antibody or antigen-binding fragment described herein.

In some embodiments, the isolated polynucleotide comprises
a VH-encoding nucleotide sequence of SEQ ID NO: 22, 24, 26, 28, 30, 32, 34, 36, 38, 40, 42, 44, 46, or 48, or a sequence having at least 80% identity thereto; and/or
a VL-encoding nucleotide sequence of SEQ ID NO: 69, 71, 73, 75, 77, 79, 81, 83, 85, 87, 89, 91, 93, 95, or 97, or a sequence having at least 80% identity thereto.

In some embodiments, the isolated polynucleotide comprises
a VH-encoding nucleotide sequence of SEQ ID NO: 22, or a sequence having at least 80% identity thereto, and a VL-encoding nucleotide sequence of SEQ ID NO: 81, or a sequence having at least 80% identity thereto;
a VH-encoding nucleotide sequence of SEQ ID NO: 24, or a sequence having at least 80% identity thereto, and a VL-encoding nucleotide sequence of SEQ ID NO: 75, or a sequence having at least 80% identity thereto;
a VH-encoding nucleotide sequence of SEQ ID NO: 26, or a sequence having at least 80% identity thereto, and a VL-encoding nucleotide sequence of SEQ ID NO: 75, or a sequence having at least 80% identity thereto;
a VH-encoding nucleotide sequence of SEQ ID NO: 28, or a sequence having at least 80% identity thereto, and a VL-encoding nucleotide sequence of SEQ ID NO: 73, or a sequence having at least 80% identity thereto;
a VH-encoding nucleotide sequence of SEQ ID NO: 30, or a sequence having at least 80% identity thereto, and a VL-encoding nucleotide sequence of SEQ ID NO: 75, or a sequence having at least 80% identity thereto;
a VH-encoding nucleotide sequence of SEQ ID NO: 30, or a sequence having at least 80% identity thereto, and a VL-encoding nucleotide sequence of SEQ ID NO: 97, or a sequence having at least 80% identity thereto;
a VH-encoding nucleotide sequence of SEQ ID NO: 30, or a sequence having at least 80% identity thereto, and a VL-encoding nucleotide sequence of SEQ ID NO: 77, or a sequence having at least 80% identity thereto;
a VH-encoding nucleotide sequence of SEQ ID NO: 30, or a sequence having at least 80% identity thereto, and a VL-encoding nucleotide sequence of SEQ ID NO: 73, or a sequence having at least 80% identity thereto;
a VH-encoding nucleotide sequence of SEQ ID NO: 32, or a sequence having at least 80% identity thereto, and a VL-encoding nucleotide sequence of SEQ ID NO: 75, or a sequence having at least 80% identity thereto;
a VH-encoding nucleotide sequence of SEQ ID NO: 34, or a sequence having at least 80% identity thereto, and a VL-encoding nucleotide sequence of SEQ ID NO: 71, or a sequence having at least 80% identity thereto;
a VH-encoding nucleotide sequence of SEQ ID NO: 34, or a sequence having at least 80% identity thereto, and a VL-encoding nucleotide sequence of SEQ ID NO: 95, or a sequence having at least 80% identity thereto;
a VH-encoding nucleotide sequence of SEQ ID NO: 36, or a sequence having at least 80% identity thereto, and a VL-encoding nucleotide sequence of SEQ ID NO: 71, or a sequence having at least 80% identity thereto;
a VH-encoding nucleotide sequence of SEQ ID NO: 38, or a sequence having at least 80% identity thereto, and a VL-encoding nucleotide sequence of SEQ ID NO: 77, or a sequence having at least 80% identity thereto;
a VH-encoding nucleotide sequence of SEQ ID NO: 38, or a sequence having at least 80% identity thereto, and a VL-encoding nucleotide sequence of SEQ ID NO: 79, or a sequence having at least 80% identity thereto;
a VH-encoding nucleotide sequence of SEQ ID NO: 38, or a sequence having at least 80% identity thereto, and a VL-encoding nucleotide sequence of SEQ ID NO: 83, or a sequence having at least 80% identity thereto;
a VH-encoding nucleotide sequence of SEQ ID NO: 38, or a sequence having at least 80% identity thereto, and a VL-encoding nucleotide sequence of SEQ ID NO: 85, or a sequence having at least 80% identity thereto;
a VH-encoding nucleotide sequence of SEQ ID NO: 38, or a sequence having at least 80% identity thereto, and a VL-encoding nucleotide sequence of SEQ ID NO: 73, or a sequence having at least 80% identity thereto;
a VH-encoding nucleotide sequence of SEQ ID NO: 40, or a sequence having at least 80% identity thereto, and a VL-encoding nucleotide sequence of SEQ ID NO: 77, or a sequence having at least 80% identity thereto;
a VH-encoding nucleotide sequence of SEQ ID NO: 42, or a sequence having at least 80% identity thereto, and a VL-encoding nucleotide sequence of SEQ ID NO: 93, or a sequence having at least 80% identity thereto;
a VH-encoding nucleotide sequence of SEQ ID NO: 42, or a sequence having at least 80% identity thereto, and a VL-encoding nucleotide sequence of SEQ ID NO: 69, or a sequence having at least 80% identity thereto;
a VH-encoding nucleotide sequence of SEQ ID NO: 44, or a sequence having at least 80% identity thereto, and a VL-encoding nucleotide sequence of SEQ ID NO: 87, or a sequence having at least 80% identity thereto;
a VH-encoding nucleotide sequence of SEQ ID NO: 46, or a sequence having at least 80% identity thereto, and a VL-encoding nucleotide sequence of SEQ ID NO: 89, or a sequence having at least 80% identity thereto; or
a VH-encoding nucleotide sequence of SEQ ID NO: 48, or a sequence having at least 80% identity thereto, and a VL-encoding nucleotide sequence of SEQ ID NO: 91, or a sequence having at least 80% identity thereto.

In another aspect, provided herein is a vector comprising the polynucleotide encoding the isolated antibody or antigen-binding fragment described herein.

In another aspect, provided herein is a recombinant cell expressing the isolated antibody or antigen-binding fragment described herein. In some embodiments, the cell is a hybridoma. In some embodiments, the antibody or antigen-binding fragment is recombinantly produced.

In another aspect, provided herein is a recombinant cell comprising the polynucleotide or the vector encoding the isolated antibody or antigen-binding fragment described herein. In some embodiments, the cell is a hybridoma. In some embodiments, the antibody or antigen-binding fragment is recombinantly produced.

In another aspect, provided herein is a kit comprising (i) the isolated antibody or antigen-binding fragment described herein, or the polynucleotide or the vector encoding the said isolated antibody or antigen-binding fragment; and (ii) packaging for the same.

In another aspect, provided herein is an affinity matrix comprising the isolated antibody or antigen-binding fragment described herein.

In another aspect, provided herein is a method of producing the isolated antibody or antigen-binding fragment described herein, wherein said method comprises culturing the recombinant cell described herein and isolating said antibody or antigen-binding fragment.

In another aspect, provided herein is a method of detecting a polypeptide comprising a linker peptide comprising the amino acid sequence of GGSEGKSSGSGSESKSTGGS (SEQ ID NO: 98) in a sample, said method comprising (i) contacting the sample with the isolated antibody or antigen-binding fragment described herein, and (ii) detecting the binding of the polypeptide to said isolated antibody or antigen-binding fragment.

In another aspect, provided herein is a method of detecting a polypeptide comprising a linker peptide comprising the amino acid sequence of GGSEGKSSGSGSESKSTGGS (SEQ ID NO: 98) in a sample, said method comprising (i)

contacting the sample with an antibody means capable of binding to said linker peptide, and (ii) detecting the binding of the polypeptide to said antibody means.

In another aspect, provided herein is a method of measuring the amount of a polypeptide comprising a linker peptide comprising the amino acid sequence of GGSEGKSSGSGSESKSTGGS (SEQ ID NO: 98) in a sample, said method comprising (i) contacting the sample with the isolated antibody or antigen-binding fragment described herein, and (ii) quantitating the binding of the polypeptide to said isolated antibody or antigen-binding fragment.

In another aspect, provided herein is a method of measuring the amount of a polypeptide comprising a linker peptide comprising the amino acid sequence of GGSEGKSSGSGSESKSTGGS (SEQ ID NO: 98) in a sample, said method comprising (i) contacting the sample with an antibody means capable of binding to said linker peptide, and (ii) quantitating the binding of the polypeptide to said isolated antibody means.

In some embodiments of the method of measuring the amount of a polypeptide comprising a linker peptide of SEQ ID NO: 98, the method further comprises comparing the binding measured in step (ii) to a control value. In some embodiments, the control value is a predetermined value.

In various embodiments, the polypeptide comprising a linker peptide comprising the amino acid sequence of GGSEGKSSGSGSESKSTGGS (SEQ ID NO: 98) is an antibody, antigen-binding fragment, or a chimeric antigen receptor. In some embodiments, the antibody or antigen-binding fragment is a human antibody, a monoclonal antibody, a single chain antibody, a Fab, a Fab', a F(ab')2, a Fv, or a scFv. In some embodiments, the antibody or antigen-binding fragment is a multi-specific antibody or antigen-binding fragment. In some embodiments, the antibody or antigen binding fragment is a bispecific antibody or antigen-binding fragment.

In another aspect, provided herein is a method of generating an antibody that specifically binds to an immunorecessive epitope, comprising
a) immunizing an adult animal with a plurality of tolerogens,
b) administering to the adult animal an agent that selectively kills rapidly proliferating lymphocytes,
c) immunizing the adult animal with a plurality of immunogens, each of said immunogens comprising the immunorecessive epitope conjugated to one of the tolerogens used in step (a),
d) obtaining B lymphocytes from the adult animal after step (c),
e) screening hybridomas or an antibody library generated from the B lymphocytes obtained in step (d) for a candidate antibody which specifically binds to the immunorecessive epitope; and
f) isolating the antibody identified in step (e) as specifically binding to the immunorecessive epitope.

In some embodiments of the antibody generation method, step (c) comprises, after the initial immunization, administering to the adult animal one or more booster doses of said immunogen or of an immunogen comprising the immunorecessive epitope conjugated to a different tolerogen used in step (a).

In some embodiments of the antibody generation method, the agent is an alkylating agent. In some embodiments, the agent is cyclophosphamide.

In some embodiments of the antibody generation method, step (b) is repeated at least once. In some embodiments, step (b) is repeated twice.

In some embodiments of the antibody generation method, the immunorecessive epitope is a peptide of less than 50 amino acids in length. In some embodiments, the immunorecessive epitope is a peptide of about 10-30 amino acids in length. In some embodiments, the immunorecessive epitope is a peptide of about 20 amino acids in length. In some embodiments, the immunorecessive epitope is a peptide of about 14 amino acids in length.

In some embodiments of the antibody generation method, the tolerogen is a carrier protein. In some embodiments, the carrier protein is selected from ovalbumin (OVA), keyhole limpet haemocyanin (KLH), and blue carrier protein (BCP).

In some embodiments of the antibody generation method, said animal is a mouse.

BRIEF DESCRIPTION OF THE DRAWINGS

FIG. 2A displays ELISA data obtained from the first animal cohort (Cohort 1); FIG. 2B displays ELISA data obtained from the second animal cohort (Cohort 2); and, FIG. 2C displays ELISA data obtained from the third animal cohort (Cohort 3).

FIG. 3A displays flow cytometry data obtained from first animal cohort (Cohort 1); FIG. 3B displays flow cytometry data obtained from the second animal cohort (Cohort 2); and, FIG. 3C, displays flow cytometry data obtained from the third animal cohort (Cohort 3). Figure discloses "G4S" as SEQ ID NO: 100.

FIG. 9A and FIG. 9B show such data as acquired via ELISA-based methods for binding against GP5B83-HL-scFv-HSA-His (GC5W47) and CD9B441-HL-ScFv-His (A003W10), respectively. An unrelated his-tagged antigen, CD70 (CD70-His), was used for counter-screening (FIG. 9C). Monoclones derived from different hybrid parents are indicated by different shapes, as summarized in the reference table. Binding of MSCD331 specific sera (positive control for FIGS. 9A-9B) or CD70 and His-specific sera (positive controls for FIG. 9C), and secondary antibody alone (negative control) to the cell lines are also shown. The absorbance (optical density, O.D.) was measured at 450 nm.

DETAILED DESCRIPTION

Definitions

Figure 1:
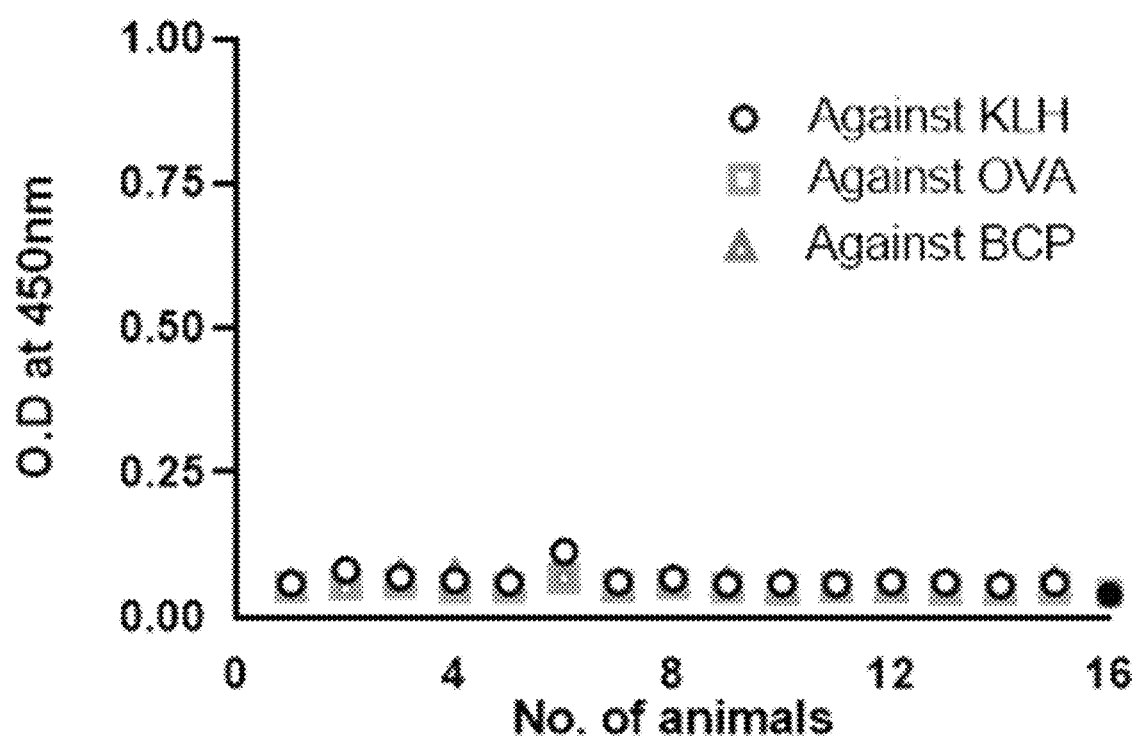
FIG. 1 demonstrates sera from animals on day 7 post tolerization showing no binding to tolerogens. Sera from tolerized animals were diluted 1:100 in assay diluent and plated onto keyhole limpet haemocyanin (KLH)-, ovalbumin (OVA)-, and blue carrier protein (BCP)-(open shapes) coated plates to determine presence of any tolerogen specific titer. The sera titers were compared to secondary alone control (filled shapes). The absorbance (optical density, O.D.) was measured at 450 nm.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extra-chromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" antibody or antigen-binding fragment, as used herein, is intended to refer to an antibody or antigen-binding fragment which is substantially free of other antibodies or antigen-binding fragments having different antigenic specificities (for instance, an isolated antibody that specifically binds to the linker peptide of SEQ ID NO: 98 is substantially free of antibodies that specifically bind antigens other than the linker peptide of SEQ ID NO: 98). An isolated antibody may specifically binds to an epitope, isoform or variant of the linker peptide of SEQ ID NO: 98.

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=# of identical positions/total # of positions ×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include linker specific antibodies, or antigen-binding fragments, that have framework, scaffold, or other non-binding regions that do not share significant identity with the antibodies and antigen-binding fragments described herein, but do incorporate one or more CDRs or other sequences needed to confer binding that are 90%, 91%, 92%, 93%, 94%, 95%, 96%, 97%, 98%, or 99% identical to such sequences described herein.

A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The terms "express" and "produce" (or "expression" and "production") are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

An "effective amount" or "therapeutically effective amount" refers to an amount effective, at dosages and for periods of time necessary, to achieve a desired therapeutic result. A therapeutically effective amount of an anti-linker antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

"Antibody" refers to all isotypes of immunoglobulins (IgG, IgA, IgE, IgM, IgD, and IgY) including various monomeric, polymeric and chimeric forms, unless otherwise specified. Specifically encompassed by the term "antibody" are polyclonal antibodies, monoclonal antibodies (mAbs), and antibody-like polypeptides, such as chimeric antibodies and humanized antibodies.

"Antigen-binding fragments" are any proteinaceous structure that may exhibit binding affinity for a particular antigen. Antigen-binding fragments include those provided by any known technique, such as enzymatic cleavage, peptide synthesis, and recombinant techniques. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies (e.g., scFv), linear antibodies, single domain antibodies such as sdAb (either VL or VH), camelid VHH domains, multi-specific antibodies formed from antibody fragments, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, a monovalent fragment consisting of the VL, VH, CL and CH1 domains, or a monovalent antibody as described in WO2007059782, bivalent fragments comprising two Fab fragments linked by a disulfide bridge at the hinge region, a Fd fragment consisting essentially of the VH and CH1 domains; a Fv fragment consisting essentially of the VL and VH domains of a single arm of an antibody, a dAb fragment (Ward et al., Nature 341, 544-546 (1989)), which consists essentially of a VH domain and also called domain antibodies (Holt et al; Trends Biotechnol. 2003 November; 21(11): 484-90); camelid or nanobodies (Revets et al; Expert Opin Biol Ther. 2005 January; 5(1):111-24); an isolated complementarity determining region (CDR), and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase.

The terms "CDR", and its plural "CDRs", refer to a complementarity determining region (CDR) of which three make up the binding character of a light chain variable region (LCDR1, LCDR2 and LCDR3) and three make up the binding character of a heavy chain variable region (HCDR1, HCDR2 and HCDR3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat et al., Sequences of Proteins of Immunological Interest, 5th ed. NIH Publication No. 91-3242 (1991); Chothia et al., "Canonical Structures For the Hypervariable Regions of Immunoglobulins," J. Mol. Biol. 196:901 (1987); and MacCallum et al., "Antibody-Antigen Interactions: Contact Analysis and Binding Site Topography," J. Mol. Biol. 262:732 (1996)), each of which is hereby incorporated by reference in its entirety.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia et al., "Canonical Structures For the Hypervariable Regions of Immunoglobulins," J. Mol. Biol. 196: 901 (1987); Chothia et al., "Conformations of Immunoglobulin Hypervariable Regions," I 342:877 (1989); Martin and Thornton, "Structural Families in Loops of Homologous Proteins: Automatic Classification, Modelling and Application to Antibodies," J. Mol. Biol. 263:800 (1996), each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

"Specifically bind" or "bind specifically" or derivatives thereof when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a Kd of less than about $1×10^{-8}$ M, as measured by a surface plasmon resonance assay or a cell-binding assay. Phrases such as "[antigen]-specific" antibody (e.g., linker-specific antibody) are meant to convey that the recited antibody specifically binds the recited antigen.

A "vector" is a replicon, such as plasmid, phage, cosmid, or virus in which another nucleic acid segment may be operably inserted so as to bring about the replication or expression of the segment.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

The term "sample" as used herein refers to any composition or mixture that can contain an analyte of interest. The sample may be a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term "sample," as used herein, encompasses materials removed from a subject or materials present in a subject.

The term "immunorecessive epitope" as used herein is intended to refer to epitopes that are typically not efficient for use in generating an antibody response by immunization, at least so far as polyclonal and monoclonal antibody production is concerned. Such immunorecessive epitopes will generally be less abundant and/or less antigenic than other epitopes commonly associated with them in the immunogen. Even under circumstances wherein the immunorecessive epitope can elicit a strong antibody response, this response can be, for example, statistically masked by the overall number of antibodies produced as a consequence of the antigenic challenge due to other epitopes associated with the immunorecessive epitope in the immunogen (referred to as "immunodominant epitopes"). In some embodiments, the immunorecessive epitope is a short peptide of less than about 50 amino acids in length, for example, about 6-40 amino acids, about 8-35 amino acids, about 10-30 amino acids, about 10-20 amino acids, about 15-25 amino acids, about 14 amino acid or about 20 amino acids. In one specific embodiment, the immunorecessive epitope is the linker peptide of SEQ ID NO: 98, or a fragment thereof.

The term "tolerogen" as used herein refers to an antigenic agent which promotes the development of tolerance in a subject (e.g., an animal). The term "tolerance" as used herein refers to a decreased level of an immune response, a delay in the onset or progression of an immune response and/or a reduced risk of the onset or progression of an immune response. Any part of an immunogen that does not bear the epitope against which the immune response is to be elicited can be used as a tolerogen. For example, wild-type CHO-K1 cells can be used as a tolerogen when antigen-expressing CHO-K1 cells are used as an immunogen, or Fc can be used as a tolerogen when Fc-tagged antigen is being used as an immunogen. Non-limiting examples of tolerogens include peptides, proteins, and cells. In some embodiments, tolerogens used herein include, for example, carrier proteins such as ovalbumin (OVA), keyhole limpet haemocyanin (KLH), and blue carrier protein (BCP).

The term "immunogen" as used herein refers to an antigenic agent that is capable of eliciting an immune response in a subject (e.g, an animal). In some embodiments, immunogens used herein comprise an immunorecessive epitope, such as a short linker peptide, conjugated to a carrier protein described herein.

The embodiments described herein are not limited to particular methods, reagents, compounds, compositions or biological systems, which can, of course, vary.

Linker-Specific Antibodies and Antigen-Binding Fragments

Described herein are isolated antibodies or antigen-binding fragments that specifically bind to the linker peptide comprising the amino acid sequence of GGSEGKSSGSGS-ESKSTGGS (SEQ ID NO: 98). In some embodiments, the described isolated antibodies or antigen-binding fragments thereof specifically bind to a linker peptide consisting of the amino acid sequence of GGSEGKSSGSGSESKSTGGS (SEQ ID NO: 98).

The general structure of an antibody molecule comprises an antigen binding domain, which includes heavy and light chains, and the Fc domain, which serves a variety of functions, including complement fixation and binding antibody receptors. In some embodiments, the isolated antibodies or antigen-binding fragments antibody may specifically binds to a fragment or a variant of the linker peptide of SEQ ID NO: 98.

The described linker-specific antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The linker-specific antibodies and antigen-binding fragments may be derived from any species by recombinant means. For example, the antibodies or antigen-binding fragments may be mouse, rat, goat, horse, swine, bovine, chicken, rabbit, camelid, donkey, human, or chimeric versions thereof. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

The antibodies may include monoclonal antibodies including murine, human, humanized and chimeric monoclonal antibodies, polyclonal, antigen-binding fragments, bispecific or multispecific antibodies, monomeric, dimeric, tetrameric or multimeric antibodies, single chain antibodies, domain antibodies and any other modified configuration of the immunoglobulin molecule that comprises an antigen binding site of the required specificity. The antibody can be a naturally-occurring antibody, e.g., an antibody isolated and/or purified from a mammal, e.g., a murine, primate, mouse, rabbit, goat, horse, chicken, hamster, human, etc. Alternatively, the antibody can be an engineered (e.g., genetically-engineered) antibody.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

Humanized antibodies have antigen binding sites derived from non-human species and the variable region frameworks are derived from human immunoglobulin sequences. Human antibodies have heavy and light chain variable regions in which both the framework and the antigen binding site are derived from sequences of human origin.

The antibodies or antigen-binding fragments described herein can occur in a variety of forms, but will include one or more of the antibody CDRs shown in Table 1. In some embodiments are provided a linker-specific antibody, or an antigen-binding fragment thereof, comprising a heavy chain comprising a CDR1, a CDR2, and a CDR3 of any one of the antibodies described in Table 1. In some embodiments are provided a linker-specific antibody, or an antigen-binding fragment thereof, comprising a heavy chain comprising a CDR1, a CDR2, and a CDR3 of any one of the antibodies described in Table 1 and a light chain comprising a CDR1, a CDR2, and a CDR3 of any one of the antibodies described in Table 1.

In some embodiments are provided a linker-specific antibody, or an antigen-binding fragment thereof, comprising a heavy chain comprising a heavy chain variable domain of any one of the antibodies described in Table 2. In some embodiments are provided a linker-specific antibody, or an antigen-binding fragment thereof, comprising a light chain comprising a light chain variable domain of any one of the antibodies described in Table 2. In some embodiments are provided a linker-specific antibody, or an antigen-binding fragment thereof, comprising a heavy chain comprising a heavy chain variable domain of any one of the antibodies described in Table 2 and a light chain comprising a light chain variable domain of any one of the antibodies described in Table 2. In some embodiments, the heavy chain variable domain of a linker-specific antibody described herein, or an antigen-binding fragment thereof, is encoded by a VH-encoding nucleotide sequence described in Table 2. In some embodiments, the light chain variable domain of a linker-specific antibody described herein, or an antigen-binding fragment thereof, is encoded by a VL-encoding nucleotide sequence described in Table 2.

TABLE 1

Exemplary anti-linker antibodies and their CDR sequences

| Clone Name | Sample name | HCDR1 | SEQ ID NO | HCDR2 | SEQ ID NO | HCDR3 | SEQ ID NO | Sample name | LCDR1 | SEQ ID NO | LCDR2 | SEQ ID NO | LCDR3 | SEQ ID NO |
|---|---|---|---|---|---|---|---|---|---|---|---|---|---|---|
| 13D5F7 | VH1 | GFNIKNTY | 11 | IDPTNGNT | 12 | AGLGSNYFYSDV | 13 | VK1 | QSLLDSDGKTY | 49 | LVS | | WQGTHFPRT | 51 |
| 16B1A7 | VH2 | GYTFTRYW | 10 | IHPSDSDT | 8 | LTMPVEGDY | 9 | VK2 | QSLLDSDGETY | 52 | LVS | | WQGTFFPRT | 54 |
| 16B1C7 | VH3 | GYTFTRYW | 10 | IHPSDSDT | 8 | LTMPVEGDY | 9 | VK3 | QSLLDSDGETY | 52 | LVS | | WQGTFFPRT | 54 |
| 16B1D4 | VH4 | GYTFTRYW | 10 | IHPSDSDT | 8 | LTMPVEGDY | 9 | VK4 | QSLLDSDGETY | 52 | LVS | | WQGTFFPRT | 54 |
| 16B1E3 | VH5 | GYPFTRYW | 10 | IHPSDSDT | 8 | LTMPVEGDY | 9 | VK5 | QSLLDSDGETY | 52 | LVS | | WQGTFFPRT | 54 |
| 17G3D6 | VH6 | GYPFTRYW | 7 | IHPSDSDT | 8 | LTMPVEGDY | 9 | VK7 | QSLLDSDGKTY | 49 | LVS | | WQGTFFPYT | 57 |
| 17F3H6 | VH7 | GYPFTRYW | 7 | IHPSDSDT | 8 | LTMPVEGDY | 9 | VK6 | QSLLDSDGETY | 52 | QVS | | WQGTFFPRT | 54 |
| 17G3E9 | VH8 | GYPFTRYW | 7 | IHPSDSDT | 8 | LTMPVEGDY | 9 | VK8 | QSLLDSDGKTY | 49 | LVS | | WQGTFFPYT | 57 |
| 17G3B2 | VH9 | GYPFTRYW | 10 | IHPSDSDT | 8 | LTMPVEGDY | 9 | VK9 | QSLLDSDGKTY | 49 | LVS | | WQGTFFPYT | 57 |
| 18B4B4 | VH10 | GYTFTRYW | 10 | IHPSDSDT | 8 | LTMPVEGDY | 9 | VK10 | QSLLDSDGETY | 52 | QVS | | WQGTFFPRT | 54 |
| 18B4F3 | VH11 | GYTFTRYW | 10 | IHPSDSDT | 8 | LTMPVEGDY | 9 | VK11 | QSLLDSDGETY | 52 | QVS | | WQGTFFPRT | 54 |
| 18B4G2 | VH12 | GYTFTRYW | 10 | IHPSDSDT | 8 | LTMPVEGDY | 9 | VK12 | QSLLDSDGETY | 52 | QVS | | WQGTFFPRT | 54 |
| 18B4F5 | VH13 | GYTFTRYW | 10 | IHPSDSDT | 8 | LTMPVEGDY | 9 | VK13 | QSLLDSDGETY | 52 | QVS | | WQGTFFPRT | 54 |
| 19D1E9 | VH14 | GITFRNYW | 1 | IRLKSDYYAT | 2 | TGFDWDDY | 3 | VK14 | QSLLDSDGKTY | 49 | LVS | | WQGTFFPYT | 57 |
| 21H7C10 | VH15 | GYTFTRYW | 10 | IHPSDSDT | 8 | LTMPVEGDY | 9 | VK15 | QSLLDSDGETY | 52 | QVS | | WQGTFFPRT | 54 |

TABLE 1-continued

Exemplary anti-linker antibodies and their CDR sequences

| Clone Name | Sample name | HCDR1 | SEQ ID NO | HCDR2 | SEQ ID NO | HCDR3 | SEQ ID NO | Sample name | LCDR1 | SEQ ID NO | LCDR2 | SEQ ID NO | LCDR3 | SEQ ID NO |
|---|---|---|---|---|---|---|---|---|---|---|---|---|---|---|
| 21H7C6 | VH16 | GYTFTRYW | 10 | IHPSDSDT | 8 | LTMPVEGDY | 9 | VK16 | ENIYSY | 55 | NAK | | QHHYVTPPT | 60 |
| 21H7H10 | VH17 | GYTFTRYW | 10 | IHPSDSDT | 8 | LTMPVEGDY | 9 | VK17 | ENIYSY | 55 | NAK | | QHHYVTPPT | 60 |
| 22H5B12 | VH18 | GYPFTRYW | 7 | IHPSDSDT | 8 | LTMPVEGDY | 9 | VK18 | QSLLDSDGETY | 52 | QVS | | WQGTFFPRT | 54 |
| 22H5G10 | VH19 | GYPFTRYW | 7 | IHPSDSDT | 8 | LTMPVEGDY | 9 | VK19 | QSLLDSDGETY | 52 | QVS | | WQGTFFPRT | 54 |
| 22H5B7 | VH20 | GYPFTRYW | 7 | IHPSDSDT | 8 | LTMPVEGDY | 9 | VK20 | QSLLDSDGETY | 52 | QVS | | WQGTFFPRT | 54 |
| 22H5C1 | VH21 | GYPFTRYW | 7 | IHPSDSDT | 8 | LTMPVEGDY | 9 | VK21 | QSLLDSDGETY | 52 | QVS | | WQGTFFPRT | 54 |
| 22H5F12 | VH22 | GYPFTRYW | 7 | IHPSDSDT | 8 | LTMPVEGDY | 9 | VK22 | QSLLDSDGETY | 52 | QVS | | WQGTFFPRT | 54 |
| 23F1A3 | VH23 | GYTFTRYW | 10 | IHPSDSDT | 8 | LTMPVEGDY | 9 | VK23 | QSLLDSDGETY | 52 | QVS | | WQGTFFPRT | 54 |
| 23F1E1 | VH24 | GYTFTRYW | 10 | IHPSDSDT | 8 | LTMPVEGDY | 9 | VK24 | QSLLDSDGETY | 52 | QVS | | WQGTFFPRT | 54 |
| 23F1E7 | VH25 | GYTFTRYW | 10 | IHPSDSDT | 8 | LTMPVEGDY | 9 | VK25 | QSLLDSDGETY | 52 | QVS | | WQGTFFPRT | 54 |
| 30H3A3 | VH26 | GFNIKNTY | 11 | IDPANGYT | 14 | AAFSSYVGYFDV | 15 | VK26 | QSLLETDGRTY | 58 | LVS | | WQGTHFPRT | 51 |
| 30H3C4 | VH27 | GFNIKNTY | 11 | IDPANGYT | 14 | AAFSSYVGYFDV | 15 | VK27 | QSLLETDGRTY | 58 | LVS | | WQGTHFPRT | 51 |
| 7C2H8 | VH28 | GYTFTDYY | 16 | INPNHGGS | 17 | ARIGIYHGDYGEFDY | 18 | VK28 | KSLLHSNGNTY | 61 | RMS | | MQHLKYPFT | 63 |
| 8H9F11 | VH29 | GYTFTSYW | 19 | IHPSDSDT | 8 | ASFITTVGDV | 20 | VK29 | QSLLDSDGKTY | 49 | LVS | | WQGTHFPRT | 51 |
| 16B1F4 | VH30 | GYTFTRYW | 10 | IHPSDSDT | 8 | LTMPVEGDY | 9 | VK30 | QSLLDSDGETY | 52 | LVS | | WQGTFFPRT | 54 |
| 13D5C10 | VH31 | GFNIKNTY | 11 | IDPTNGNT | 12 | AGLGSNYFYSDV | 13 | VK31 | QSLLDSDGKTY | 49 | LVS | | WQGTHFPRT | 51 |

TABLE 1-continued

Exemplary anti-linker antibodies and their CDR sequences

| Clone Name | Sample name | HCDR1 | SEQ ID NO | HCDR2 | SEQ ID NO | HCDR3 | SEQ ID NO | Sample name | LCDR1 | SEQ ID NO | LCDR2 | SEQ ID NO | LCDR3 | SEQ ID NO |
|---|---|---|---|---|---|---|---|---|---|---|---|---|---|---|
| 16B1F10 | VH32 | GYTFTRYW | 10 | IHPSDSDT | 8 | LTMPVEGDY | 9 | VK32 | GNIHNY | 64 | NAK | | QHFWNAPYT | 65 |
| 16B1C1 | VH33 | GYTFTRYW | 10 | IHPSDSDT | 8 | LTMPVEGDY | 9 | VK33 | QSLLDSDGETY | 52 | LVS | | WQGTFFPRT | 54 |
| 17G3D11 | VH34 | GITFSNYW | 4 | IRMRSDNYAT | 5 | TGFDWDDY | 3 | VK34 | QSLLDSDGKTY | 49 | LVS | | WQGTHFPYT | 57 |
| 17G3F6 | VH35 | GITFSNYW | 4 | IRMRSDNYAT | 5 | TGFDWDDY | 3 | VK35 | QSLLDSDGKTY | 49 | LVS | | WQGTHFPYT | 57 |
| 18B4B10 | VH36 | GYTFTRYW | 10 | IHPSDSDT | 8 | LTMPVEGDY | 9 | VK36 | QSLLDSDGETY | 52 | QVS | | WQGTFFPRT | 54 |
| 18B4F11 | VH37 | GYTFTRYW | 10 | IHPSDSDT | 8 | LTMPVEGDY | 9 | VK37 | QSLLDSDGETY | 52 | QVS | | WQGTFFPRT | 54 |
| 18B4H10 | VH38 | GYTFTRYW | 10 | IHPSDSDT | 8 | LTMPVEGDY | 9 | VK38 | QSLLDSDGETY | 52 | QVS | | WQGTFFPRT | 54 |
| 19D1B6 | VH39 | GYPFTRYW | 7 | IHPSDSDT | 8 | LTMPVEGDY | 9 | VK39 | QSLLYSSNQKNY | 66 | WAS | | QQYYSYPPA | 67 |
| 21H7C8 | VH40 | GYTFTRYW | 10 | IHPSDSDT | 8 | LTMPVEGDY | 9 | VK40 | QSLLDSDGETY | 52 | QVS | | WQGTFFPRT | 54 |
| 21H7B10 | VH41 | GYPFTRYW | 7 | IHPSDSDT | 8 | LTMPVEGDY | 9 | VK41 | QSLLDSDGETY | 52 | QVS | | WQGTFFPRT | 54 |
| 22H5A4 | VH42 | GYTFTRYW | 10 | IHPSDSDT | 8 | LTMPVEGDY | 9 | VK42 | QSLLDSDGETY | 52 | QVS | | WQGTFFPRT | 54 |
| 22H5D1 | VH43 | GYPFTRYW | 7 | IHPSDSDT | 8 | LTMPVEGDY | 9 | VK43 | QSLLDSDGETY | 52 | QVS | | WQGTFFPRT | 54 |
| 23F1A2 | VH44 | GYTFTRYW | 10 | IHPSDSDT | 8 | LTMPVEGDY | 9 | VK44 | QSLLDSDGETY | 52 | QVS | | WQGTFFPRT | 54 |
| 23F1D8 | VH45 | GYTFTRYW | 10 | IHPSDSDT | 8 | LTMPVEGDY | 9 | VK45 | QSLLDSDGETY | 52 | QVS | | WQGTFFPRT | 54 |
| 30H3B3 | VH46 | GFNIKNTY | 11 | IDPANGYT | 14 | AAFSSYVGYFDV | 15 | VK46 | QSLLETDGRTY | 58 | LVS | | WQGTHFPRT | 51 |

TABLE 1-continued

Exemplary anti-linker antibodies and their CDR sequences

| Clone Name | Sample name | HCDR1 | SEQ ID NO | HCDR2 | SEQ ID NO | HCDR3 | SEQ ID NO | Sample name | LCDR1 | SEQ ID NO | LCDR2 | SEQ ID NO | LCDR3 | SEQ ID NO |
|---|---|---|---|---|---|---|---|---|---|---|---|---|---|---|
| 30H3C3 | VH47 | GFNIKNTY | 11 | IDPANGYT | 14 | AAFSSYVGYFDV | 15 | VK47 | QSLLETDGRTY | 58 | LVS | | WQGTHFPRT | 51 |
| 30H3C8 | VH48 | GFNIKNTY | 11 | IDPANGYT | 14 | AAFSSYVGYFDV | 15 | VK48 | QSLLETDGRTY | 58 | LVS | | WQGTHFPRT | 51 |
| 7C2G8 | VH49 | GYTFTDYY | 16 | INPNHGGS | 17 | ARIGIYHGDYGEFDY | 18 | VK49 | KSLLHSNGNTY | 61 | RMS | | MQHLKYPFT | 63 |
| 8H9E7 | VH50 | GYTFTSYW | 19 | IHPSDSDT | 8 | ASFITTVGDV | 20 | VK50 | QSLLDSDGKTY | 49 | LVS | | WQGTHFPRT | 51 |

TABLE 2

Nucleotide and amino acid sequence of heavy chain variable domain (VH) and light chain variable domain (VL) of exemplary anti-linker antibodies

| Clone Name | Sample name | Nucleotide sequence (SEQ ID NO) | Amino acid sequence (SEQ ID NO) | Sample name | Nucleotide sequence (SEQ ID NO) | Amino acid sequence (SEQ ID NO) |
|---|---|---|---|---|---|---|
| 13D5F7 | VH1 | 42 | 41 | VK1 | 69 | 68 |
| 16B1A7 | VH2 | 34 | 33 | VK2 | 71 | 70 |
| 16B1C7 | VH3 | 36 | 35 | VK3 | 71 | 70 |
| 16B1D4 | VH4 | 34 | 33 | VK4 | 71 | 70 |
| 16B1E3 | VH5 | 34 | 33 | VK5 | 71 | 70 |
| 17G3D6 | VH6 | 28 | 27 | VK7 | 75 | 74 |
| 17F3H6 | VH7 | 30 | 29 | VK6 | 73 | 72 |
| 17G3E9 | VH8 | 30 | 29 | VK8 | 75 | 74 |
| 17G3B2 | VH9 | 32 | 31 | VK9 | 75 | 74 |
| 18B4B4 | VH10 | 38 | 37 | VK10 | 77 | 76 |
| 18B4F3 | VH11 | 38 | 37 | VK11 | 79 | 78 |
| 18B4G2 | VH12 | 38 | 37 | VK12 | 77 | 76 |
| 18B4F5 | VH13 | 38 | 37 | VK13 | 77 | 76 |
| 19D1E9 | VH14 | 22 | 21 | VK14 | 81 | 80 |
| 21H7C10 | VH15 | 38 | 37 | VK15 | 77 | 76 |
| 21H7C6 | VH16 | 38 | 37 | VK16 | 83 | 82 |
| 21H7H10 | VH17 | 38 | 37 | VK17 | 85 | 84 |
| 22H5B12 | VH18 | 30 | 29 | VK18 | 73 | 72 |
| 22H5G10 | VH19 | 30 | 29 | VK19 | 73 | 72 |
| 22H5B7 | VH20 | 30 | 29 | VK20 | 73 | 72 |
| 22H5C1 | VH21 | 30 | 29 | VK21 | 73 | 72 |
| 22H5F12 | VH22 | 30 | 29 | VK22 | 73 | 72 |
| 23F1A3 | VH23 | 38 | 37 | VK23 | 77 | 76 |
| 23F1E1 | VH24 | 38 | 37 | VK24 | 79 | 78 |
| 23F1E7 | VH25 | 38 | 37 | VK25 | 77 | 76 |
| 30H3A3 | VH26 | 44 | 43 | VK26 | 87 | 86 |
| 30H3C4 | VH27 | 44 | 43 | VK27 | 87 | 86 |
| 7C2H8 | VH28 | 46 | 45 | VK28 | 89 | 88 |
| 8H9F11 | VH29 | 48 | 47 | VK29 | 91 | 90 |
| 16B1F4 | VH30 | 34 | 33 | VK30 | 71 | 70 |
| 13D5C10 | VH31 | 42 | 41 | VK31 | 93 | 92 |
| 16B1F10 | VH32 | 34 | 33 | VK32 | 95 | 94 |
| 16B1C1 | VH33 | 34 | 33 | VK33 | 71 | 70 |
| 17G3D11 | VH34 | 24 | 23 | VK34 | 75 | 74 |
| 17G3F6 | VH35 | 24 | 23 | VK35 | 75 | 74 |
| 18B4B10 | VH36 | 38 | 37 | VK36 | 77 | 76 |
| 18B4F11 | VH37 | 40 | 39 | VK37 | 77 | 76 |
| 18B4H10 | VH38 | 38 | 37 | VK38 | 77 | 76 |
| 19D1B6 | VH39 | 30 | 29 | VK39 | 97 | 96 |
| 21H7C8 | VH40 | 38 | 37 | VK40 | 79 | 78 |
| 21H7B10 | VH41 | 30 | 29 | VK41 | 77 | 76 |
| 22H5A4 | VH42 | 38 | 37 | VK42 | 73 | 72 |
| 22H5D1 | VH43 | 30 | 29 | VK43 | 73 | 72 |
| 23F1A2 | VH44 | 38 | 37 | VK44 | 77 | 76 |
| 23F1D8 | VH45 | 38 | 37 | VK45 | 77 | 76 |
| 30H3B3 | VH46 | 44 | 43 | VK46 | 87 | 86 |
| 30H3C3 | VH47 | 44 | 43 | VK47 | 87 | 86 |
| 30H3C8 | VH48 | 44 | 43 | VK48 | 87 | 86 |
| 7C2G8 | VH49 | 46 | 45 | VK49 | 89 | 88 |
| 8H9E7 | VH50 | 48 | 47 | VK50 | 91 | 90 |

In some embodiments, the isolated antibody, or antigen-binding fragment thereof, comprises a heavy chain CDR1, a heavy chain CDR2, and a heavy chain CDR3 of a heavy chain variable region (VH) comprising an amino acid sequence of SEQ ID NO: 21, 23, 27, 29, 31, 33, 35, 37, 39, 41, 43, 45, or 47, or a sequence having at least 80%, 85%, 90%, preferably 95% or more, such as 95%, 96%, 97%, 98%, or 99% identity thereto.

In some embodiments, the isolated antibody, or antigen-binding fragment thereof, comprises a light chain CDR1, a light chain CDR2, and a light chain CDR3 of a light chain variable region (VL) comprising an amino acid sequence of SEQ ID NO: 68, 70, 72, 74, 76, 78, 80, 82, 84, 86, 88, 90, 92, 94, or 96, or a sequence having at least 80%, 85%, 90%, preferably 95% or more, such as 95%, 96%, 97%, 98%, or 99% identity thereto.

In some embodiments, the isolated antibody, or antigen-binding fragment thereof, comprises a heavy chain CDR1, a heavy chain CDR2, and a heavy chain CDR3 of a heavy chain variable region (VH) comprising an amino acid sequence of SEQ ID NO: 21, 23, 27, 29, 31, 33, 35, 37, 39, 41, 43, 45, or 47, or a sequence having at least 80%, 85%, 90%, preferably 95% or more, such as 95%, 96%, 97%, 98%, or 99% identity thereto; and a light chain CDR1, a light chain CDR2, and a light chain CDR3 of a light chain variable region (VL) comprising an amino acid sequence of SEQ ID NO: 68, 70, 72, 74, 76, 78, 80, 82, 84, 86, 88, 90, 92, 94, or 96, or a sequence having at least 80%, 85%, 90%, preferably 95% or more, such as 95%, 96%, 97%, 98%, or 99% identity thereto.

In some embodiments, the isolated antibody, or antigen-binding fragment thereof, comprises a heavy chain CDR1, a heavy chain CDR2, and a heavy chain CDR3 of a heavy chain variable region (VH) comprising an amino acid sequence of SEQ ID NO: 21, 23, 27, 29, 31, 33, 35, 37, 39, 41, 43, 45, or 47; and a light chain CDR1, a light chain CDR2, and a light chain CDR3 of a light chain variable region (VL) comprising an amino acid sequence of SEQ ID NO: 68, 70, 72, 74, 76, 78, 80, 82, 84, 86, 88, 90, 92, 94, or 96.

In some embodiments, the anti-linker antibody or antigen-binding fragment comprises
- a heavy chain CDR1 comprising the amino acid sequence of SEQ ID NO: 1, a heavy chain CDR2 comprising the amino acid sequence of SEQ ID NO: 2, and a heavy chain CDR3 comprising the amino acid sequence of SEQ ID NO: 3;
- a heavy chain CDR1 comprising the amino acid sequence of SEQ ID NO: 4, a heavy chain CDR2 comprising the amino acid sequence of SEQ ID NO: 5, and a heavy chain CDR3 comprising the amino acid sequence of SEQ ID NO: 3;
- a heavy chain CDR1 comprising the amino acid sequence of SEQ ID NO: 7, a heavy chain CDR2 comprising the amino acid sequence of SEQ ID NO: 8, and a heavy chain CDR3 comprising the amino acid sequence of SEQ ID NO: 9;
- a heavy chain CDR1 comprising the amino acid sequence of SEQ ID NO: 10, a heavy chain CDR2 comprising the amino acid sequence of SEQ ID NO: 8, and a heavy chain CDR3 comprising the amino acid sequence of SEQ ID NO: 9;
- a heavy chain CDR1 comprising the amino acid sequence of SEQ ID NO: 11, a heavy chain CDR2 comprising the amino acid sequence of SEQ ID NO: 12, and a heavy chain CDR3 comprising the amino acid sequence of SEQ ID NO: 13;
- a heavy chain CDR1 comprising the amino acid sequence of SEQ ID NO: 11, a heavy chain CDR2 comprising the amino acid sequence of SEQ ID NO: 14, and a heavy chain CDR3 comprising the amino acid sequence of SEQ ID NO: 15;
- a heavy chain CDR1 comprising the amino acid sequence of SEQ ID NO: 16, a heavy chain CDR2 comprising the amino acid sequence of SEQ ID NO: 17, and a heavy chain CDR3 comprising the amino acid sequence of SEQ ID NO: 18; or
- a heavy chain CDR1 comprising the amino acid sequence of SEQ ID NO: 19, a heavy chain CDR2 comprising the amino acid sequence of SEQ ID NO: 8, and a heavy chain CDR3 comprising the amino acid sequence of SEQ ID NO: 20.

In some embodiments, the anti-linker antibody or antigen-binding fragment comprises a heavy chain CDR1 selected from the group consisting of SEQ ID NOs: 1, 4, 7, 10, 11, 16, and 19, and conservative modifications thereof, wherein the anti-linker antibody or antigen-binding fragment binds the linker peptide comprising the amino acid sequence of GGSEGKSSGSGSESKSTGGS (SEQ ID NO: 98).

In some embodiments, the anti-linker antibody or antigen-binding fragment comprises a heavy chain CDR2 selected from the group consisting of SEQ ID NOs: 2, 5, 8, 12, 14, and 17, and conservative modifications thereof, wherein the anti-linker antibody or antigen-binding fragment binds the linker peptide comprising the amino acid sequence of GGSEGKSSGSGSESKSTGGS (SEQ ID NO: 98).

In some embodiments, the anti-linker antibody or antigen-binding fragment comprises a heavy chain CDR3 selected from the group consisting of SEQ ID NOs: 3, 9, 13, 15, 18, and 20, and conservative modifications thereof, wherein the anti-linker antibody or antigen-binding fragment binds the linker peptide comprising the amino acid sequence of GGSEGKSSGSGSESKSTGGS (SEQ ID NO: 98).

In some embodiments, the anti-linker antibody or antigen-binding fragment comprises
- a light chain CDR1 comprising the amino acid sequence of SEQ ID NO: 49, a light chain CDR2 comprising the amino acid sequence of SEQ ID NO: 50, and a light chain CDR3 comprising the amino acid sequence of SEQ ID NO: 51;
- a light chain CDR1 comprising the amino acid sequence of SEQ ID NO: 52, a light chain CDR2 comprising the amino acid sequence of SEQ ID NO: 50, and a light chain CDR3 comprising the amino acid sequence of SEQ ID NO: 54;
- a light chain CDR1 comprising the amino acid sequence of SEQ ID NO: 52, a light chain CDR2 comprising the amino acid sequence of SEQ ID NO: 53, and a light chain CDR3 comprising the amino acid sequence of SEQ ID NO: 54;
- a light chain CDR1 comprising the amino acid sequence of SEQ ID NO: 49, a light chain CDR2 comprising the amino acid sequence of SEQ ID NO: 50, and a light chain CDR3 comprising the amino acid sequence of SEQ ID NO: 57;
- a light chain CDR1 comprising the amino acid sequence of SEQ ID NO: 55, a light chain CDR2 comprising the amino acid sequence of SEQ ID NO: 56, and a light chain CDR3 comprising the amino acid sequence of SEQ ID NO: 60;
- a light chain CDR1 comprising the amino acid sequence of SEQ ID NO: 58, a light chain CDR2 comprising the amino acid sequence of SEQ ID NO: 50, and a light chain CDR3 comprising the amino acid sequence of SEQ ID NO: 51;
- a light chain CDR1 comprising the amino acid sequence of SEQ ID NO: 61, a light chain CDR2 comprising the amino acid sequence of SEQ ID NO: 59, and a light chain CDR3 comprising the amino acid sequence of SEQ ID NO: 63;
- a light chain CDR1 comprising the amino acid sequence of SEQ ID NO: 64, a light chain CDR2 comprising the amino acid sequence of SEQ ID NO: 56, and a light chain CDR3 comprising the amino acid sequence of SEQ ID NO: 65; or
- a light chain CDR1 comprising the amino acid sequence of SEQ ID NO: 66, a light chain CDR2 comprising the amino acid sequence of SEQ ID NO: 62, and a light chain CDR3 comprising the amino acid sequence of SEQ ID NO: 67.

In some embodiments, the anti-linker antibody or antigen-binding fragment comprises a light chain CDR1 selected from the group consisting of SEQ ID NOs: 49, 52, 55, 58, 61, 64 and 66, and conservative modifications thereof, wherein the anti-linker antibody or antigen-binding fragment binds the linker peptide comprising the amino acid sequence of GGSEGKSSGSGSESKSTGGS (SEQ ID NO: 98).

In some embodiments, the anti-linker antibody or antigen-binding fragment comprises a light chain CDR2 selected from the group consisting of SEQ ID NOs: 50, 53, 56, 59, and 62, and conservative modifications thereof, wherein the anti-linker antibody or antigen-binding fragment binds the linker peptide comprising the amino acid sequence of GGSEGKSSGSGSESKSTGGS (SEQ ID NO: 98).

In some embodiments, the anti-linker antibody or antigen-binding fragment comprises a light chain CDR3 selected from the group consisting of SEQ ID NOs: 51, 54, 57, 60, 63, 65, and 67, and conservative modifications thereof, wherein the anti-linker antibody or antigen-binding fragment binds the linker peptide comprising the amino acid sequence of GGSEGKSSGSGSESKSTGGS (SEQ ID NO: 98).

In some embodiments, the anti-linker antibody or antigen-binding fragment comprises the heavy chain CDR1, the heavy chain CDR2, the heavy chain CDR3, the light chain CDR1, the light chain CDR2 and the light chain CDR3 comprising the amino acid sequence of
- a) SEQ ID NOs: 1, 2, 3, 49, 50, and 57, respectively;
- b) SEQ ID NOs: 4, 5, 3, 49, 50, and 57, respectively;
- c) SEQ ID NOs: 7, 8, 9, 52, 53, and 54, respectively;
- d) SEQ ID NOs: 7, 8, 9, 49, 50, and 57, respectively;
- e) SEQ ID NOs: 7, 8, 9, 66, 62, and 67, respectively;
- f) SEQ ID NOs: 10, 8, 9, 52, 50, and 54, respectively;
- g) SEQ ID NOs: 10, 8, 9, 52, 53, and 54, respectively;
- h) SEQ ID NOs: 10, 8, 9, 64, 56, and 65, respectively;
- i) SEQ ID NOs: 10, 8, 9, 55, 56, and 60, respectively;
- j) SEQ ID NOs: 11, 12, 13, 49, 50, and 51, respectively;
- k) SEQ ID NOs: 11, 14, 15, 58, 50, and 51, respectively;
- l) SEQ ID NOs: 16, 17, 18, 61, 59, and 63, respectively; or
- m) SEQ ID NOs: 19, 8, 20, 49, 50, and 51, respectively.

In some embodiments, the anti-linker antibody or antigen-binding fragment comprises
a heavy chain variable region (VH) comprising an amino acid sequence of SEQ ID NO: 21, 23, 25, 27, 29, 31, 33, 35, 37, 39, 41, 43, 45, or 47, or a sequence having at least 80%, 85%, 90%, preferably 95% or more, such as 95%, 96%, 97%, 98%, or 99% identity thereto; and/or
a light chain variable region (VL) comprising an amino acid sequence of SEQ ID NO: 68, 70, 72, 74, 76, 78, 80, 82, 84, 86, 88, 90, 92, 94, or 96, or a sequence having at least 80%, 85%, 90%, preferably 95% or more, such as 95%, 96%, 97%, 98%, or 99% identity thereto.

In some embodiments, the anti-linker antibody or antigen-binding fragment comprises
a heavy chain variable region (VH) comprising an amino acid sequence of SEQ ID NO: 21, 23, 25, 27, 29, 31, 33, 35, 37, 39, 41, 43, 45, or 47; and/or
a light chain variable region (VL) comprising an amino acid sequence of SEQ ID NO: 68, 70, 72, 74, 76, 78, 80, 82, 84, 86, 88, 90, 92, 94, or 96.

In some embodiments, the anti-linker antibody or antigen-binding fragment comprises
a heavy chain variable region (VH) comprising an amino acid sequence encoded by a nucleotide sequence of SEQ ID NO: 22, 24, 26, 28, 30, 32, 34, 36, 38, 40, 42, 44, 46, or 48, or a sequence having at least 80%, 85%, 90%, preferably 95% or more, such as 95%, 96%, 97%, 98%, or 99% identity thereto; and/or
a light chain variable region (VL) comprising an amino acid sequence encoded by a nucleotide sequence of SEQ ID NO: 69, 71, 73, 75, 77, 79, 81, 83, 85, 87, 89, 91, 93, 95, or 97, or a sequence having at least 80%, 85%, 90%, preferably 95% or more, such as 95%, 96%, 97%, 98%, or 99% identity thereto.

In some embodiments, the anti-linker antibody or antigen-binding fragment comprises
a heavy chain variable region (VH) comprising an amino acid sequence encoded by a nucleotide sequence of SEQ ID NO: 22, 24, 26, 28, 30, 32, 34, 36, 38, 40, 42, 44, 46, or 48; and/or
a light chain variable region (VL) comprising an amino acid sequence encoded by a nucleotide sequence of SEQ ID NO: 69, 71, 73, 75, 77, 79, 81, 83, 85, 87, 89, 91, 93, 95, or 97.

In some embodiments, the anti-linker antibody or antigen-binding fragment comprises
a heavy chain variable region comprising an amino acid sequence of SEQ ID NO: 21, or a sequence having at least 80%, 85%, 90%, preferably 95% or more, such as 95%, 96%, 97%, 98%, or 99% identity thereto, and a light chain variable region comprising an amino acid sequence of SEQ ID NO: 80, or a sequence having at least 80%, 85%, 90%, preferably 95% or more, such as 95%, 96%, 97%, 98%, or 99% identity thereto;
a heavy chain variable region comprising an amino acid sequence of SEQ ID NO: 23, or a sequence having at least 80%, 85%, 90%, preferably 95% or more, such as 95%, 96%, 97%, 98%, or 99% identity thereto, and a light chain variable region comprising an amino acid sequence of SEQ ID NO: 74, or a sequence having at least 80%, 85%, 90%, preferably 95% or more, such as 95%, 96%, 97%, 98%, or 99% identity thereto;
a heavy chain variable region comprising an amino acid sequence of SEQ ID NO: 25, or a sequence having at least 80%, 85%, 90%, preferably 95% or more, such as 95%, 96%, 97%, 98%, or 99% identity thereto, and a light chain variable region comprising an amino acid sequence of SEQ ID NO: 74, or a sequence having at least 80%, 85%, 90%, preferably 95% or more, such as 95%, 96%, 97%, 98%, or 99% identity thereto;
a heavy chain variable region comprising an amino acid sequence of SEQ ID NO: 27, or a sequence having at least 80%, 85%, 90%, preferably 95% or more, such as 95%, 96%, 97%, 98%, or 99% identity thereto, and a light chain variable region comprising an amino acid sequence of SEQ ID NO: 72, or a sequence having at least 80%, 85%, 90%, preferably 95% or more, such as 95%, 96%, 97%, 98%, or 99% identity thereto;
a heavy chain variable region comprising an amino acid sequence of SEQ ID NO: 29, or a sequence having at least 80%, 85%, 90%, preferably 95% or more, such as 95%, 96%, 97%, 98%, or 99% identity thereto, and a light chain variable region comprising an amino acid sequence of SEQ ID NO: 74, or a sequence having at least 80%, 85%, 90%, preferably 95% or more, such as 95%, 96%, 97%, 98%, or 99% identity thereto;
a heavy chain variable region comprising an amino acid sequence of SEQ ID NO: 29, or a sequence having at least 80%, 85%, 90%, preferably 95% or more, such as 95%, 96%, 97%, 98%, or 99% identity thereto, and a light chain variable region comprising an amino acid sequence of SEQ ID NO: 96, or a sequence having at least 80%, 85%, 90%, preferably 95% or more, such as 95%, 96%, 97%, 98%, or 99% identity thereto;
a heavy chain variable region comprising an amino acid sequence of SEQ ID NO: 29, or a sequence having at least 80%, 85%, 90%, preferably 95% or more, such as 95%, 96%, 97%, 98%, or 99% identity thereto, and a light chain variable region comprising an amino acid sequence of SEQ ID NO: 76, or a sequence having at least 80%, 85%, 90%, preferably 95% or more, such as 95%, 96%, 97%, 98%, or 99% identity thereto;
a heavy chain variable region comprising an amino acid sequence of SEQ ID NO: 29, or a sequence having at least 80%, 85%, 90%, preferably 95% or more, such as 95%, 96%, 97%, 98%, or 99% identity thereto, and a light chain variable region comprising an amino acid sequence of SEQ ID NO: 72, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 31, or a sequence having at least 80%, 85%, 90%, preferably 95% or more, such as 95%, 96%, 97%, 98%, or 99% identity thereto, and a light chain variable region comprising an amino acid sequence of SEQ ID NO: 74, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 33, or a sequence having at least 80%, 85%, 90%, preferably 95% or more, such as 95%, 96%, 97%, 98%, or 99% identity thereto, and a light chain variable region comprising an amino acid sequence of SEQ ID NO: 70, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 33, or a sequence having at least 80%, 85%, 90%, preferably 95% or more, such as 95%, 96%, 97%, 98%, or 99% identity thereto, and a light chain variable region comprising an amino acid sequence of SEQ ID NO: 94, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 35, or a sequence having at least 80%, 85%, 90%, preferably 95% or more, such as 95%, 96%, 97%, 98%, or 99% identity thereto, and a light chain variable region comprising an amino acid sequence of SEQ ID NO: 70, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 37, or a sequence having at least 80%, 85%, 90%, preferably 95% or more, such as 95%, 96%, 97%, 98%, or 99% identity thereto, and a light chain variable region comprising an amino acid sequence of SEQ ID NO: 76, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 37, or a sequence having at least 80%, 85%, 90%, preferably 95% or more, such as 95%, 96%, 97%, 98%, or 99% identity thereto, and a light chain variable region comprising an amino acid sequence of SEQ ID NO: 78, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 37, or a sequence having at least 80%, 85%, 90%, preferably 95% or more, such as 95%, 96%, 97%, 98%, or 99% identity thereto, and a light chain variable region comprising an amino acid sequence of SEQ ID NO: 82, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 37, or a sequence having at least 80%, 85%, 90%, preferably 95% or more, such as 95%, 96%, 97%, 98%, or 99% identity thereto, and a light chain variable region comprising an amino acid sequence of SEQ ID NO: 84, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 37, or a sequence having at least 80%, 85%, 90%, preferably 95% or more, such as 95%, 96%, 97%, 98%, or 99% identity thereto, and a light chain variable region comprising an amino acid sequence of SEQ ID NO: 72, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 39, or a sequence having at least 80%, 85%, 90%, preferably 95% or more, such as 95%, 96%, 97%, 98%, or 99% identity thereto, and a light chain variable region comprising an amino acid sequence of SEQ ID NO: 76, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 41, or a sequence having at least 80%, 85%, 90%, preferably 95% or more, such as 95%, 96%, 97%, 98%, or 99% identity thereto, and a light chain variable region comprising an amino acid sequence of SEQ ID NO: 92, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 41, or a sequence having at least 80%, 85%, 90%, preferably 95% or more, such as 95%, 96%, 97%, 98%, or 99% identity thereto, and a light chain variable region comprising an amino acid sequence of SEQ ID NO: 68, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 43, or a sequence having at least 80%, 85%, 90%, preferably 95% or more, such as 95%, 96%, 97%, 98%, or 99% identity thereto, and a light chain variable region comprising an amino acid sequence of SEQ ID NO: 86, or a sequence having at least 80%, 85%, 90%, preferably 95% or more, such as 95%, 96%, 97%, 98%, or 99% identity thereto;

a heavy chain variable region comprising an amino acid sequence of SEQ ID NO: 45, or a sequence having at least 80%, 85%, 90%, preferably 95% or more, such as 95%, 96%, 97%, 98%, or 99% identity thereto, and a light chain variable region comprising an amino acid sequence of SEQ ID NO: 88, or a sequence having at least 80%, 85%, 90%, preferably 95% or more, such as 95%, 96%, 97%, 98%, or 99% identity thereto; or a heavy chain variable region comprising an amino acid sequence of SEQ ID NO: 47, or a sequence having at least 80%, 85%, 90%, preferably 95% or more, such as 95%, 96%, 97%, 98%, or 99% identity thereto, and a light chain variable region comprising an amino acid sequence of SEQ ID NO: 90, or a sequence having at least 80%, 85%, 90%, preferably 95% or more, such as 95%, 96%, 97%, 98%, or 99% identity thereto.

In some embodiments, the anti-linker antibody or antigen-binding fragment comprises a heavy chain variable region comprising an amino acid sequence of SEQ ID NO: 21, and a light chain variable region comprising an amino acid sequence of SEQ ID NO: 80;

a heavy chain variable region comprising an amino acid sequence of SEQ ID NO: 23, and a light chain variable region comprising an amino acid sequence of SEQ ID NO: 74;

a heavy chain variable region comprising an amino acid sequence of SEQ ID NO: 25, and a light chain variable region comprising an amino acid sequence of SEQ ID NO: 74;

a heavy chain variable region comprising an amino acid sequence of SEQ ID NO: 27, and a light chain variable region comprising an amino acid sequence of SEQ ID NO: 72;

a heavy chain variable region comprising an amino acid sequence of SEQ ID NO: 29, and a light chain variable region comprising an amino acid sequence of SEQ ID NO: 74;

a heavy chain variable region comprising an amino acid sequence of SEQ ID NO: 29, and a light chain variable region comprising an amino acid sequence of SEQ ID NO: 96;

a heavy chain variable region comprising an amino acid sequence of SEQ ID NO: 29, and a light chain variable region comprising an amino acid sequence of SEQ ID NO: 76;

a heavy chain variable region comprising an amino acid sequence of SEQ ID NO: 29, and a light chain variable region comprising an amino acid sequence of SEQ ID NO: 72;

a heavy chain variable region comprising an amino acid sequence of SEQ ID NO: 31, and a light chain variable region comprising an amino acid sequence of SEQ ID NO: 74;

a heavy chain variable region comprising an amino acid sequence of SEQ ID NO: 33, and a light chain variable region comprising an amino acid sequence of SEQ ID NO: 70;

a heavy chain variable region comprising an amino acid sequence of SEQ ID NO: 33, and a light chain variable region comprising an amino acid sequence of SEQ ID NO: 94;

a heavy chain variable region comprising an amino acid sequence of SEQ ID NO: 35, and a light chain variable region comprising an amino acid sequence of SEQ ID NO: 70;

a heavy chain variable region comprising an amino acid sequence of SEQ ID NO: 37, and a light chain variable region comprising an amino acid sequence of SEQ ID NO: 76;

a heavy chain variable region comprising an amino acid sequence of SEQ ID NO: 37, and a light chain variable region comprising an amino acid sequence of SEQ ID NO: 78;

a heavy chain variable region comprising an amino acid sequence of SEQ ID NO: 37, and a light chain variable region comprising an amino acid sequence of SEQ ID NO: 82;

a heavy chain variable region comprising an amino acid sequence of SEQ ID NO: 37, and a light chain variable region comprising an amino acid sequence of SEQ ID NO: 84;

a heavy chain variable region comprising an amino acid sequence of SEQ ID NO: 37, and a light chain variable region comprising an amino acid sequence of SEQ ID NO: 72;

a heavy chain variable region comprising an amino acid sequence of SEQ ID NO: 39, and a light chain variable region comprising an amino acid sequence of SEQ ID NO: 76;

a heavy chain variable region comprising an amino acid sequence of SEQ ID NO: 41, and a light chain variable region comprising an amino acid sequence of SEQ ID NO: 92;

a heavy chain variable region comprising an amino acid sequence of SEQ ID NO: 41, and a light chain variable region comprising an amino acid sequence of SEQ ID NO: 68;

a heavy chain variable region comprising an amino acid sequence of SEQ ID NO: 43, and a light chain variable region comprising an amino acid sequence of SEQ ID NO: 86;

a heavy chain variable region comprising an amino acid sequence of SEQ ID NO: 45, and a light chain variable region comprising an amino acid sequence of SEQ ID NO: 88; or a heavy chain variable region comprising an amino acid sequence of SEQ ID NO: 47, and a light chain variable region comprising an amino acid sequence of SEQ ID NO: 90.

In some embodiments, the anti-linker antibody or antigen-binding fragment comprises a heavy chain CDR1, a heavy chain CDR2 and a heavy chain CDR3 of a heavy chain variable region comprising an amino acid sequence of SEQ ID NO: 21, and a light chain CDR1, a light chain CDR2 and a light chain CDR3 of a light chain variable region comprising an amino acid sequence of SEQ ID NO: 80;

a heavy chain CDR1, a heavy chain CDR2 and a heavy chain CDR3 of a heavy chain variable region comprising an amino acid sequence of SEQ ID NO: 23, and a light chain CDR1, a light chain CDR2 and a light chain CDR3 of a light chain variable region comprising an amino acid sequence of SEQ ID NO: 74;

a heavy chain CDR1, a heavy chain CDR2 and a heavy chain CDR3 of a heavy chain variable region comprising an amino acid sequence of SEQ ID NO: 25, and a light chain CDR1, a light chain CDR2 and a light chain CDR3 of a light chain variable region comprising an amino acid sequence of SEQ ID NO: 74;

a heavy chain CDR1, a heavy chain CDR2 and a heavy chain CDR3 of a heavy chain variable region comprising an amino acid sequence of SEQ ID NO: 27, and a light chain CDR1, a light chain CDR2 and a light chain CDR3 of a light chain variable region comprising an amino acid sequence of SEQ ID NO: 72;

a heavy chain CDR1, a heavy chain CDR2 and a heavy chain CDR3 of a heavy chain variable region comprising an amino acid sequence of SEQ ID NO: 29, and a light chain CDR1, a light chain CDR2 and a light chain CDR3 of a light chain variable region comprising an amino acid sequence of SEQ ID NO: 74;

a heavy chain CDR1, a heavy chain CDR2 and a heavy chain CDR3 of a heavy chain variable region comprising an amino acid sequence of SEQ ID NO: 29, and a light chain CDR1, a light chain CDR2 and a light chain CDR3 of a light chain variable region comprising an amino acid sequence of SEQ ID NO: 96;

a heavy chain CDR1, a heavy chain CDR2 and a heavy chain CDR3 of a heavy chain variable region comprising an amino acid sequence of SEQ ID NO: 29, and a light chain CDR1, a light chain CDR2 and a light chain CDR3 of a light chain variable region comprising an amino acid sequence of SEQ ID NO: 76;

a heavy chain CDR1, a heavy chain CDR2 and a heavy chain CDR3 of a heavy chain variable region comprising an amino acid sequence of SEQ ID NO: 29, and a light chain CDR1, a light chain CDR2 and a light chain CDR3 of a light chain variable region comprising an amino acid sequence of SEQ ID NO: 72;

a heavy chain CDR1, a heavy chain CDR2 and a heavy chain CDR3 of a heavy chain variable region comprising an amino acid sequence of SEQ ID NO: 31, and a light chain CDR1, a light chain CDR2 and a light chain CDR3 of a light chain variable region comprising an amino acid sequence of SEQ ID NO: 74;

a heavy chain CDR1, a heavy chain CDR2 and a heavy chain CDR3 of a heavy chain variable region comprising an amino acid sequence of SEQ ID NO: 33, and a light chain CDR1, a light chain CDR2 and a light chain CDR3 of a light chain variable region comprising an amino acid sequence of SEQ ID NO: 70;

a heavy chain CDR1, a heavy chain CDR2 and a heavy chain CDR3 of a heavy chain variable region comprising an amino acid sequence of SEQ ID NO: 33, and a light chain CDR1, a light chain CDR2 and a light chain CDR3 of a light chain variable region comprising an amino acid sequence of SEQ ID NO: 94;

a heavy chain CDR1, a heavy chain CDR2 and a heavy chain CDR3 of a heavy chain variable region comprising an amino acid sequence of SEQ ID NO: 35, and a light chain CDR1, a light chain CDR2 and a light chain CDR3 of a light chain variable region comprising an amino acid sequence of SEQ ID NO: 70;

a heavy chain CDR1, a heavy chain CDR2 and a heavy chain CDR3 of a heavy chain variable region comprising an amino acid sequence of SEQ ID NO: 37, and a light chain CDR1, a light chain CDR2 and a light chain CDR3 of a light chain variable region comprising an amino acid sequence of SEQ ID NO: 76;

a heavy chain CDR1, a heavy chain CDR2 and a heavy chain CDR3 of a heavy chain variable region comprising an amino acid sequence of SEQ ID NO: 37, and a light chain CDR1, a light chain CDR2 and a light chain CDR3 of a light chain variable region comprising an amino acid sequence of SEQ ID NO: 78;

a heavy chain CDR1, a heavy chain CDR2 and a heavy chain CDR3 of a heavy chain variable region comprising an amino acid sequence of SEQ ID NO: 37, and a light chain CDR1, a light chain CDR2 and a light chain CDR3 of a light chain variable region comprising an amino acid sequence of SEQ ID NO: 82;

a heavy chain CDR1, a heavy chain CDR2 and a heavy chain CDR3 of a heavy chain variable region comprising an amino acid sequence of SEQ ID NO: 37, and a light chain CDR1, a light chain CDR2 and a light chain CDR3 of a light chain variable region comprising an amino acid sequence of SEQ ID NO: 84;

a heavy chain CDR1, a heavy chain CDR2 and a heavy chain CDR3 of a heavy chain variable region comprising an amino acid sequence of SEQ ID NO: 37, and a light chain CDR1, a light chain CDR2 and a light chain CDR3 of a light chain variable region comprising an amino acid sequence of SEQ ID NO: 72;

a heavy chain CDR1, a heavy chain CDR2 and a heavy chain CDR3 of a heavy chain variable region comprising an amino acid sequence of SEQ ID NO: 39, and a light chain CDR1, a light chain CDR2 and a light chain CDR3 of a light chain variable region comprising an amino acid sequence of SEQ ID NO: 76;

a heavy chain CDR1, a heavy chain CDR2 and a heavy chain CDR3 of a heavy chain variable region comprising an amino acid sequence of SEQ ID NO: 41, and a light chain CDR1, a light chain CDR2 and a light chain CDR3 of a light chain variable region comprising an amino acid sequence of SEQ ID NO: 92;

a heavy chain CDR1, a heavy chain CDR2 and a heavy chain CDR3 of a heavy chain variable region comprising an amino acid sequence of SEQ ID NO: 41, and a light chain CDR1, a light chain CDR2 and a light chain CDR3 of a light chain variable region comprising an amino acid sequence of SEQ ID NO: 68;

a heavy chain CDR1, a heavy chain CDR2 and a heavy chain CDR3 of a heavy chain variable region comprising an amino acid sequence of SEQ ID NO: 43, and a light chain CDR1, a light chain CDR2 and a light chain CDR3 of a light chain variable region comprising an amino acid sequence of SEQ ID NO: 86;

a heavy chain CDR1, a heavy chain CDR2 and a heavy chain CDR3 of a heavy chain variable region comprising an amino acid sequence of SEQ ID NO: 45, and a light chain CDR1, a light chain CDR2 and a light chain CDR3 of a light chain variable region comprising an amino acid sequence of SEQ ID NO: 88; or a heavy chain CDR1, a heavy chain CDR2 and a heavy chain CDR3 of a heavy chain variable region comprising an amino acid sequence of SEQ ID NO: 47, and a light chain CDR1, a light chain CDR2 and a light chain CDR3 of a light chain variable region comprising an amino acid sequence of SEQ ID NO: 90.

In some embodiments, the anti-linker antibody or antigen-binding fragment comprises a heavy chain variable region comprising an amino acid sequence encoded by the nucleotide sequence of SEQ ID NO: 22, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 81, or a sequence having at least 80%, 85%, 90%, preferably 95% or more, such as 95%, 96%, 97%, 98%, or 99% identity thereto;

a heavy chain variable region comprising an amino acid sequence encoded by the nucleotide sequence of SEQ ID NO: 24, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 75, or a sequence having at least 80%, 85%, 90%, preferably 95% or more, such as 95%, 96%, 97%, 98%, or 99% identity thereto;

a heavy chain variable region comprising an amino acid sequence encoded by the nucleotide sequence of SEQ ID NO: 26, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 75, or a sequence having at least 80%, 85%, 90%, preferably 95% or more, such as 95%, 96%, 97%, 98%, or 99% identity thereto;

a heavy chain variable region comprising an amino acid sequence encoded by the nucleotide sequence of SEQ ID NO: 28, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 73, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 30, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 75, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 30, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 97, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 30, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 77, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 30, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 73, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 32, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 75, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 34, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 71, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 34, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 95, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 36, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 71, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 38, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 77, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 38, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 79, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 38, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 83, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 38, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 85, or a sequence having at least 80%, 85%, 90%, preferably 95% or more, such as 95%, 96%, 97%, 98%, or 99% identity thereto;
a heavy chain variable region comprising an amino acid sequence encoded by the nucleotide sequence of SEQ ID NO: 38, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 73, or a sequence having at least 80%, 85%, 90%, preferably 95% or more, such as 95%, 96%, 97%, 98%, or 99% identity thereto;

a heavy chain variable region comprising an amino acid sequence encoded by the nucleotide sequence of SEQ ID NO: 40, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 77, or a sequence having at least 80%, 85%, 90%, preferably 95% or more, such as 95%, 96%, 97%, 98%, or 99% identity thereto;

a heavy chain variable region comprising an amino acid sequence encoded by the nucleotide sequence of SEQ ID NO: 42, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 93, or a sequence having at least 80%, 85%, 90%, preferably 95% or more, such as 95%, 96%, 97%, 98%, or 99% identity thereto;

a heavy chain variable region comprising an amino acid sequence encoded by the nucleotide sequence of SEQ ID NO: 42, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 69, or a sequence having at least 80%, 85%, 90%, preferably 95% or more, such as 95%, 96%, 97%, 98%, or 99% identity thereto;

a heavy chain variable region comprising an amino acid sequence encoded by the nucleotide sequence of SEQ ID NO: 44, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 87, or a sequence having at least 80%, 85%, 90%, preferably 95% or more, such as 95%, 96%, 97%, 98%, or 99% identity thereto;

a heavy chain variable region comprising an amino acid sequence encoded by the nucleotide sequence of SEQ ID NO: 46, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 89, or a sequence having at least 80%, 85%, 90%, preferably 95% or more, such as 95%, 96%, 97%, 98%, or 99% identity thereto; or a heavy chain variable region comprising an amino acid sequence encoded by the nucleotide sequence of SEQ ID NO: 48, or a sequence having at least 80%, 85%, 90%, preferably 95% or more, such as 95%, 96%, 97%, 98%, or 99% identity thereto, and a light chain variable region comprising an amino acid sequence encoded by the nucleotide sequence of SEQ ID NO: 91, or a sequence having at least 80%, 85%, 90%, preferably 95% or more, such as 95%, 96%, 97%, 98%, or 99% identity thereto.

In some embodiments, the anti-linker antibody or antigen-binding fragment comprises a heavy chain variable region comprising an amino acid sequence encoded by the nucleotide sequence of SEQ ID NO: 22, and a light chain variable region comprising an amino acid sequence encoded by the nucleotide sequence of SEQ ID NO: 81;

a heavy chain variable region comprising an amino acid sequence encoded by the nucleotide sequence of SEQ ID NO: 24, and a light chain variable region comprising an amino acid sequence encoded by the nucleotide sequence of SEQ ID NO: 75;

a heavy chain variable region comprising an amino acid sequence encoded by the nucleotide sequence of SEQ ID NO: 26, and a light chain variable region comprising an amino acid sequence encoded by the nucleotide sequence of SEQ ID NO: 75;

a heavy chain variable region comprising an amino acid sequence encoded by the nucleotide sequence of SEQ ID NO: 28, and a light chain variable region comprising an amino acid sequence encoded by the nucleotide sequence of SEQ ID NO: 73;

a heavy chain variable region comprising an amino acid sequence encoded by the nucleotide sequence of SEQ ID NO: 30, and a light chain variable region comprising an amino acid sequence encoded by the nucleotide sequence of SEQ ID NO: 75;

a heavy chain variable region comprising an amino acid sequence encoded by the nucleotide sequence of SEQ ID NO: 30, and a light chain variable region comprising an amino acid sequence encoded by the nucleotide sequence of SEQ ID NO: 97;

a heavy chain variable region comprising an amino acid sequence encoded by the nucleotide sequence of SEQ ID NO: 30, and a light chain variable region comprising an amino acid sequence encoded by the nucleotide sequence of SEQ ID NO: 77;

a heavy chain variable region comprising an amino acid sequence encoded by the nucleotide sequence of SEQ ID NO: 30, and a light chain variable region comprising an amino acid sequence encoded by the nucleotide sequence of SEQ ID NO: 73;

a heavy chain variable region comprising an amino acid sequence encoded by the nucleotide sequence of SEQ ID NO: 32, and a light chain variable region comprising an amino acid sequence encoded by the nucleotide sequence of SEQ ID NO: 75;

a heavy chain variable region comprising an amino acid sequence encoded by the nucleotide sequence of SEQ ID NO: 34, and a light chain variable region comprising an amino acid sequence encoded by the nucleotide sequence of SEQ ID NO: 71;

a heavy chain variable region comprising an amino acid sequence encoded by the nucleotide sequence of SEQ ID NO: 34, and a light chain variable region comprising an amino acid sequence encoded by the nucleotide sequence of SEQ ID NO: 95;

a heavy chain variable region comprising an amino acid sequence encoded by the nucleotide sequence of SEQ ID NO: 36, and a light chain variable region comprising an amino acid sequence encoded by the nucleotide sequence of SEQ ID NO: 71;

a heavy chain variable region comprising an amino acid sequence encoded by the nucleotide sequence of SEQ ID NO: 38, and a light chain variable region comprising an amino acid sequence encoded by the nucleotide sequence of SEQ ID NO: 77;

a heavy chain variable region comprising an amino acid sequence encoded by the nucleotide sequence of SEQ ID NO: 38, and a light chain variable region comprising an amino acid sequence encoded by the nucleotide sequence of SEQ ID NO: 79;

a heavy chain variable region comprising an amino acid sequence encoded by the nucleotide sequence of SEQ ID NO: 38, and a light chain variable region comprising an amino acid sequence encoded by the nucleotide sequence of SEQ ID NO: 83;

a heavy chain variable region comprising an amino acid sequence encoded by the nucleotide sequence of SEQ ID NO: 38, and a light chain variable region comprising an amino acid sequence encoded by the nucleotide sequence of SEQ ID NO: 85;

a heavy chain variable region comprising an amino acid sequence encoded by the nucleotide sequence of SEQ ID NO: 38, and a light chain variable region comprising an amino acid sequence encoded by the nucleotide sequence of SEQ ID NO: 73;

a heavy chain variable region comprising an amino acid sequence encoded by the nucleotide sequence of SEQ ID NO: 40, and a light chain variable region comprising an amino acid sequence encoded by the nucleotide sequence of SEQ ID NO: 77;

a heavy chain variable region comprising an amino acid sequence encoded by the nucleotide sequence of SEQ ID NO: 42, and a light chain variable region comprising an amino acid sequence encoded by the nucleotide sequence of SEQ ID NO: 93;

a heavy chain variable region comprising an amino acid sequence encoded by the nucleotide sequence of SEQ ID NO: 42, and a light chain variable region comprising an amino acid sequence encoded by the nucleotide sequence of SEQ ID NO: 69;

a heavy chain variable region comprising an amino acid sequence encoded by the nucleotide sequence of SEQ ID NO: 44, and a light chain variable region comprising an amino acid sequence encoded by the nucleotide sequence of SEQ ID NO: 87;

a heavy chain variable region comprising an amino acid sequence encoded by the nucleotide sequence of SEQ ID NO: 46, and a light chain variable region comprising an amino acid sequence encoded by the nucleotide sequence of SEQ ID NO: 89; or a heavy chain variable region comprising an amino acid sequence encoded by the nucleotide sequence of SEQ ID NO: 48, and a light chain variable region comprising an amino acid sequence encoded by the nucleotide sequence of SEQ ID NO: 91.

In various embodiments, the anti-linker antibody or antigen-binding fragment does not bind to the amino acid sequence GGGGSGGGGSGGGGSGGGS (SEQ ID NO: 99).

In various embodiments, the anti-linker antibody or antigen-binding fragment does not have non-specific binding to Immunoglobulin G (IgG). In some embodiments, the anti-linker antibody or antigen-binding fragment does not bind to the constant region of Immunoglobulin G (IgG).

The specific antibodies defined by CDR and/or variable domain sequence discussed in the above paragraphs may include additional modifications.

The linker-specific antibodies or antigen-binding fragments described herein include variants having single or multiple amino acid substitutions, deletions, or additions that retain the biological properties (e.g., binding affinity or immune effector activity) of the described linker-specific antibodies or antigen-binding fragments. In the context of the present disclosure the following notations are, unless otherwise indicated, used to describe a mutation; i) substitution of an amino acid in a given position is written as e.g. S228P which means a substitution of a Serine in position 228 with a Proline; and ii) for specific variants the specific three or one letter codes are used, including the codes Xaa and X to indicate any amino acid residue. Thus, the substitution of Serine for Arginine in position 228 is designated as: S228P, or the substitution of any amino acid residue for Serine in position 228 is designated as S228P. In case of deletion of Serine in position 228 it is indicated by S228*. The skilled person may produce variants having single or multiple amino acid substitutions, deletions, or additions.

These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

Amino acid substitutions may be conservative, by which it is meant the substituted amino acid has similar chemical properties to the original amino acid. A skilled person would understand which amino acids share similar chemical properties. For example, the following groups of amino acids share similar chemical properties such as size, charge and polarity: Group 1—Ala, Ser, Thr, Pro, Gly; Group 2—Asp, Asn, Glu, Gln; Group 3—His, Arg, Lys; Group 4—Met, Leu, Ile, Val, Cys; Group 5—Phe, Thy, Trp.

The linker-specific antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 or IgG4 isotype. In some embodiments the antibody isotype is IgA1 or IgA2. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

The antibody or antigen-binding fragment can have any level of affinity or avidity for the linker peptide comprising the amino acid sequence of GGSEGKSSGSGSESKSTGGS (SEQ ID NO: 98). In some embodiments, the antibody or antigen-binding fragment may bind the linker peptide of SEQ ID NO: 98 with a range of affinities ($K_D$). In various embodiments, the antibody or antigen-binding fragment binds to the linker peptide of SEQ ID NO: 98 with high affinity, for example, with a $K_D$ equal to or less than about $10^{-7}$ M, such as but not limited to, 1-9.9 (or any range or value therein, such as 1, 2, 3, 4, 5, 6, 7, 8, or 9)$\times 10^{-8}$ M, $10^{-9}$ M, $10^{-10}$ M, $10^{-11}$ M, $10^{-12}$ M, $10^{-13}$ M, $10^{-14}$ M, $10^{-15}$ M or any range or value therein, as determined by surface plasmon resonance or the Kinexa method, as practiced by those of skill in the art. One example affinity is equal to or less than 1×10⁻⁸ M. Another example affinity is equal to or less than 1×10⁻⁹ M.

Methods of testing antibodies for the ability to bind to the target peptide or any portion thereof are known in the art and include any antibody-antigen binding assay, such as, for example, radioimmunoassay (RIA), Western blot, enzyme-linked immunosorbent assay (ELISA), immunoprecipitation, and competitive inhibition assays.

Also disclosed are isolated polynucleotides that encode the antibodies or antigen-binding fragments that specifically bind to the linker peptide comprising the amino acid sequence of GGSEGKSSGSGSESKSTGGS (SEQ ID NO: 98). The isolated polynucleotides capable of encoding the variable domain segments provided herein may be included on the same, or different, vectors to produce antibodies or antigen-binding fragments. Exemplary polynucleotide sequences that may encode the VH or VL of an anti-linker antibody described herein, or an antigen-binding fragment thereof, are shown in Table 2.

In some embodiments, an isolated polynucleotide encoding an anti-linker antibody or antigen-binding fragment comprises
- a VH-encoding nucleotide sequence of SEQ ID NO: 22, 24, 26, 28, 30, 32, 34, 36, 38, 40, 42, 44, 46, or 48, or a sequence having at least 80%, 85%, 90%, preferably 95% or more, such as 95%, 96%, 97%, 98%, or 99% identity thereto; and/or
- a VL-encoding nucleotide sequence of SEQ ID NO: 69, 71, 73, 75, 77, 79, 81, 83, 85, 87, 89, 91, 93, 95, or 97, or a sequence having at least 80%, 85%, 90%, preferably 95% or more, such as 95%, 96%, 97%, 98%, or 99% identity thereto.

In some embodiments, an isolated polynucleotide encoding an anti-linker antibody or antigen-binding fragment comprises
- a VH-encoding nucleotide sequence of SEQ ID NO: 22, or a sequence having at least 80%, 85%, 90%, preferably 95% or more, such as 95%, 96%, 97%, 98%, or 99% identity thereto, and a VL-encoding nucleotide sequence of SEQ ID NO: 81, or a sequence having at least 80%, 85%, 90%, preferably 95% or more, such as 95%, 96%, 97%, 98%, or 99% identity thereto;
- a VH-encoding nucleotide sequence of SEQ ID NO: 24, or a sequence having at least 80%, 85%, 90%, preferably 95% or more, such as 95%, 96%, 97%, 98%, or 99% identity thereto, and a VL-encoding nucleotide sequence of SEQ ID NO: 75, or a sequence having at least 80%, 85%, 90%, preferably 95% or more, such as 95%, 96%, 97%, 98%, or 99% identity thereto;
- a VH-encoding nucleotide sequence of SEQ ID NO: 26, or a sequence having at least 80%, 85%, 90%, preferably 95% or more, such as 95%, 96%, 97%, 98%, or 99% identity thereto, and a VL-encoding nucleotide sequence of SEQ ID NO: 75, or a sequence having at least 80%, 85%, 90%, preferably 95% or more, such as 95%, 96%, 97%, 98%, or 99% identity thereto;
- a VH-encoding nucleotide sequence of SEQ ID NO: 28, or a sequence having at least 80%, 85%, 90%, preferably 95% or more, such as 95%, 96%, 97%, 98%, or 99% identity thereto, and a VL-encoding nucleotide sequence of SEQ ID NO: 73, or a sequence having at least 80%, 85%, 90%, preferably 95% or more, such as 95%, 96%, 97%, 98%, or 99% identity thereto;
- a VH-encoding nucleotide sequence of SEQ ID NO: 30, or a sequence having at least 80%, 85%, 90%, preferably 95% or more, such as 95%, 96%, 97%, 98%, or 99% identity thereto, and a VL-encoding nucleotide sequence of SEQ ID NO: 75, or a sequence having at least 80%, 85%, 90%, preferably 95% or more, such as 95%, 96%, 97%, 98%, or 99% identity thereto;
- a VH-encoding nucleotide sequence of SEQ ID NO: 30, or a sequence having at least 80%, 85%, 90%, preferably 95% or more, such as 95%, 96%, 97%, 98%, or 99% identity thereto, and a VL-encoding nucleotide sequence of SEQ ID NO: 97, or a sequence having at least 80%, 85%, 90%, preferably 95% or more, such as 95%, 96%, 97%, 98%, or 99% identity thereto;
- a VH-encoding nucleotide sequence of SEQ ID NO: 30, or a sequence having at least 80%, 85%, 90%, preferably 95% or more, such as 95%, 96%, 97%, 98%, or 99% identity thereto, and a VL-encoding nucleotide sequence of SEQ ID NO: 77, or a sequence having at least 80%, 85%, 90%, preferably 95% or more, such as 95%, 96%, 97%, 98%, or 99% identity thereto;
- a VH-encoding nucleotide sequence of SEQ ID NO: 30, or a sequence having at least 80%, 85%, 90%, preferably 95% or more, such as 95%, 96%, 97%, 98%, or 99% identity thereto, and a VL-encoding nucleotide sequence of SEQ ID NO: 73, or a sequence having at least 80%, 85%, 90%, preferably 95% or more, such as 95%, 96%, 97%, 98%, or 99% identity thereto;
- a VH-encoding nucleotide sequence of SEQ ID NO: 32, or a sequence having at least 80%, 85%, 90%, preferably 95% or more, such as 95%, 96%, 97%, 98%, or 99% identity thereto, and a VL-encoding nucleotide sequence of SEQ ID NO: 75, or a sequence having at least 80%, 85%, 90%, preferably 95% or more, such as 95%, 96%, 97%, 98%, or 99% identity thereto;
- a VH-encoding nucleotide sequence of SEQ ID NO: 34, or a sequence having at least 80%, 85%, 90%, preferably 95% or more, such as 95%, 96%, 97%, 98%, or 99% identity thereto, and a VL-encoding nucleotide sequence of SEQ ID NO: 71, or a sequence having at least 80%, 85%, 90%, preferably 95% or more, such as 95%, 96%, 97%, 98%, or 99% identity thereto;
- a VH-encoding nucleotide sequence of SEQ ID NO: 34, or a sequence having at least 80%, 85%, 90%, preferably 95% or more, such as 95%, 96%, 97%, 98%, or 99% identity thereto, and a VL-encoding nucleotide sequence of SEQ ID NO: 95, or a sequence having at least 80%, 85%, 90%, preferably 95% or more, such as 95%, 96%, 97%, 98%, or 99% identity thereto;
- a VH-encoding nucleotide sequence of SEQ ID NO: 36, or a sequence having at least 80%, 85%, 90%, preferably 95% or more, such as 95%, 96%, 97%, 98%, or 99% identity thereto, and a VL-encoding nucleotide sequence of SEQ ID NO: 71, or a sequence having at least 80%, 85%, 90%, preferably 95% or more, such as 95%, 96%, 97%, 98%, or 99% identity thereto;
- a VH-encoding nucleotide sequence of SEQ ID NO: 38, or a sequence having at least 80%, 85%, 90%, preferably 95% or more, such as 95%, 96%, 97%, 98%, or 99% identity thereto, and a VL-encoding nucleotide sequence of SEQ ID NO: 77, or a sequence having at least 80%, 85%, 90%, preferably 95% or more, such as 95%, 96%, 97%, 98%, or 99% identity thereto;
- a VH-encoding nucleotide sequence of SEQ ID NO: 38, or a sequence having at least 80%, 85%, 90%, preferably 95% or more, such as 95%, 96%, 97%, 98%, or 99% identity thereto, and a VL-encoding nucleotide sequence of SEQ ID NO: 79, or a sequence having at least 80%, 85%, 90%, preferably 95% or more, such as 95%, 96%, 97%, 98%, or 99% identity thereto;

a VH-encoding nucleotide sequence of SEQ ID NO: 38, or a sequence having at least 80%, 85%, 90%, preferably 95% or more, such as 95%, 96%, 97%, 98%, or 99% identity, and a VL-encoding nucleotide sequence of SEQ ID NO: 83, or a sequence having at least 80%, 85%, 90%, preferably 95% or more, such as 95%, 96%, 97%, 98%, or 99% identity thereto;

a VH-encoding nucleotide sequence of SEQ ID NO: 38, or a sequence having at least 80%, 85%, 90%, preferably 95% or more, such as 95%, 96%, 97%, 98%, or 99% identity thereto, and a VL-encoding nucleotide sequence of SEQ ID NO: 85, or a sequence having at least 80%, 85%, 90%, preferably 95% or more, such as 95%, 96%, 97%, 98%, or 99% identity thereto;

a VH-encoding nucleotide sequence of SEQ ID NO: 38, or a sequence having at least 80%, 85%, 90%, preferably 95% or more, such as 95%, 96%, 97%, 98%, or 99% identity thereto, and a VL-encoding nucleotide sequence of SEQ ID NO: 73, or a sequence having at least 80%, 85%, 90%, preferably 95% or more, such as 95%, 96%, 97%, 98%, or 99% identity thereto;

a VH-encoding nucleotide sequence of SEQ ID NO: 40, or a sequence having at least 80%, 85%, 90%, preferably 95% or more, such as 95%, 96%, 97%, 98%, or 99% identity thereto, and a VL-encoding nucleotide sequence of SEQ ID NO: 77, or a sequence having at least 80%, 85%, 90%, preferably 95% or more, such as 95%, 96%, 97%, 98%, or 99% identity thereto;

a VH-encoding nucleotide sequence of SEQ ID NO: 42, or a sequence having at least 80%, 85%, 90%, preferably 95% or more, such as 95%, 96%, 97%, 98%, or 99% identity thereto, and a VL-encoding nucleotide sequence of SEQ ID NO: 93, or a sequence having at least 80%, 85%, 90%, preferably 95% or more, such as 95%, 96%, 97%, 98%, or 99% identity thereto;

a VH-encoding nucleotide sequence of SEQ ID NO: 42, or a sequence having at least 80%, 85%, 90%, preferably 95% or more, such as 95%, 96%, 97%, 98%, or 99% identity thereto, and a VL-encoding nucleotide sequence of SEQ ID NO: 69, or a sequence having at least 80%, 85%, 90%, preferably 95% or more, such as 95%, 96%, 97%, 98%, or 99% identity thereto;

a VH-encoding nucleotide sequence of SEQ ID NO: 44, or a sequence having at least 80%, 85%, 90%, preferably 95% or more, such as 95%, 96%, 97%, 98%, or 99% identity thereto, and a VL-encoding nucleotide sequence of SEQ ID NO: 87, or a sequence having at least 80%, 85%, 90%, preferably 95% or more, such as 95%, 96%, 97%, 98%, or 99% identity thereto;

a VH-encoding nucleotide sequence of SEQ ID NO: 46, or a sequence having at least 80%, 85%, 90%, preferably 95% or more, such as 95%, 96%, 97%, 98%, or 99% identity thereto, and a VL-encoding nucleotide sequence of SEQ ID NO: 89, or a sequence having at least 80%, 85%, 90%, preferably 95% or more, such as 95%, 96%, 97%, 98%, or 99% identity thereto; or a VH-encoding nucleotide sequence of SEQ ID NO: 48, or a sequence having at least 80%, 85%, 90%, preferably 95% or more, such as 95%, 96%, 97%, 98%, or 99% identity thereto, and a VL-encoding nucleotide sequence of SEQ ID NO: 91, or a sequence having at least 80%, 85%, 90%, preferably 95% or more, such as 95%, 96%, 97%, 98%, or 99% identity thereto.

In some embodiments, an isolated polynucleotide encoding an anti-linker antibody or antigen-binding fragment comprises a VH-encoding nucleotide sequence of SEQ ID NO: 22, 24, 26, 28, 30, 32, 34, 36, 38, 40, 42, 44, 46, or 48, or a sequence having at least 80%, 85%, 90%, preferably 95% or more, such as 95%, 96%, 97%, 98%, or 99% identity thereto; and/or a VL-encoding nucleotide sequence of SEQ ID NO: 69, 71, 73, 75, 77, 79, 81, 83, 85, 87, 89, 91, 93, 95, or 97, or a sequence having at least 80%, 85%, 90%, preferably 95% or more, such as 95%, 96%, 97%, 98%, or 99% identity thereto.

In some embodiments, an isolated polynucleotide encoding an anti-linker antibody or antigen-binding fragment comprises a VH-encoding nucleotide sequence of SEQ ID NO: 22, and a VL-encoding nucleotide sequence of SEQ ID NO: 81;

a VH-encoding nucleotide sequence of SEQ ID NO: 24, and a VL-encoding nucleotide sequence of SEQ ID NO: 75;

a VH-encoding nucleotide sequence of SEQ ID NO: 26, and a VL-encoding nucleotide sequence of SEQ ID NO: 75;

a VH-encoding nucleotide sequence of SEQ ID NO: 28, and a VL-encoding nucleotide sequence of SEQ ID NO: 73;

a VH-encoding nucleotide sequence of SEQ ID NO: 30, and a VL-encoding nucleotide sequence of SEQ ID NO: 75;

a VH-encoding nucleotide sequence of SEQ ID NO: 30, and a VL-encoding nucleotide sequence of SEQ ID NO: 97;

a VH-encoding nucleotide sequence of SEQ ID NO: 30, and a VL-encoding nucleotide sequence of SEQ ID NO: 77;

a VH-encoding nucleotide sequence of SEQ ID NO: 30, and a VL-encoding nucleotide sequence of SEQ ID NO: 73;

a VH-encoding nucleotide sequence of SEQ ID NO: 32, and a VL-encoding nucleotide sequence of SEQ ID NO: 75;

a VH-encoding nucleotide sequence of SEQ ID NO: 34, and a VL-encoding nucleotide sequence of SEQ ID NO: 71;

a VH-encoding nucleotide sequence of SEQ ID NO: 34, and a VL-encoding nucleotide sequence of SEQ ID NO: 95;

a VH-encoding nucleotide sequence of SEQ ID NO: 36, and a VL-encoding nucleotide sequence of SEQ ID NO: 71;

a VH-encoding nucleotide sequence of SEQ ID NO: 38, and a VL-encoding nucleotide sequence of SEQ ID NO: 77;

a VH-encoding nucleotide sequence of SEQ ID NO: 38, and a VL-encoding nucleotide sequence of SEQ ID NO: 79;

a VH-encoding nucleotide sequence of SEQ ID NO: 38, and a VL-encoding nucleotide sequence of SEQ ID NO: 83;

a VH-encoding nucleotide sequence of SEQ ID NO: 38, and a VL-encoding nucleotide sequence of SEQ ID NO: 85;

a VH-encoding nucleotide sequence of SEQ ID NO: 38, and a VL-encoding nucleotide sequence of SEQ ID NO: 73;

a VH-encoding nucleotide sequence of SEQ ID NO: 40, and a VL-encoding nucleotide sequence of SEQ ID NO: 77;

a VH-encoding nucleotide sequence of SEQ ID NO: 42, and a VL-encoding nucleotide sequence of SEQ ID NO: 93;

a VH-encoding nucleotide sequence of SEQ ID NO: 42, and a VL-encoding nucleotide sequence of SEQ ID NO: 69;

a VH-encoding nucleotide sequence of SEQ ID NO: 44, and a VL-encoding nucleotide sequence of SEQ ID NO: 87;

a VH-encoding nucleotide sequence of SEQ ID NO: 46, and a VL-encoding nucleotide sequence of SEQ ID NO: 89; or a VH-encoding nucleotide sequence of SEQ ID NO: 48, and a VL-encoding nucleotide sequence of SEQ ID NO: 91.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 Mol. Cell. Biol. 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the linker-specific antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene, a puromycin resistance gene, a blasticidin resistance gene), glutamate synthase genes, HSV-TK, HSV-TK derivatives for ganciclovir selection, or bacterial purine nucleoside phosphorylase gene for 6-methylpurine selection (Gadi et al., 7 Gene Ther. 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate linker-specific antibody or antigen-binding fragment-producing cells. Thus, another aspect features host cells transformed with vectors comprising a nucleic acid sequence encoding an antibody or antigen-binding fragment thereof that specifically binds the linker peptide of SEQ ID NO: 98, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 *Pharmac. Ther.* 69-92 (1985)). Calcium phosphate precipitation and polyethylene glycol (PEG)-induced fusion of bacterial protoplasts with mammalian cells may also be used to transform cells.

Cells suitable for use in the expression of the linker-specific antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. Additional suitable cells may include insect cells (such as Sf7 cells), yeast cells, plant cells, or bacteria cells (such as *E. coli*). In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Suitable methods of making antibodies are known in the art. For instance, standard hybridoma methods are described in, e.g., Kohler and Milstein, *Eur. J. Immunol.*, 5, 511-519 (1976), Harlow and Lane (eds.), *Antibodies: A Laboratory Manual, CSH Press* (1988), and C. A. Janeway et al. (eds.), *Immunobiology*, 5th Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 127581 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display can also be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen (i.e., linker peptide of SEQ ID NO: 98), and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are known in the art and are described in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235, 959-973 (1994).

Antibodies, as utilized herein, can be multiple or single chain, or intact immunoglobulins, and may be derived from natural sources or from recombinant sources. Antibodies can be tetramers of immunoglobulin molecules.

In some embodiments, the antibody is a bispecific antibody. The VL and/or the VH regions of existing antibodies or the VL and VH regions identified as described herein may be engineered into bispecific full-length antibodies. Such bispecific antibodies may be made by modulating the CH3 interactions in antibody Fc to form bispecific antibodies using technologies such as those described in U.S. Pat. No. 7,695,936; Int. Pat. Publ. No. WO04/111233; U.S. Pat. Publ. No. 2010/0015133; U.S. Pat. Publ. No. 2007/0287170; Int. Pat. Publ. No. WO2008/119353; U.S. Pat. Publ. No. 2009/0182127; U.S. Pat. Publ. No. 2010/0286374; U.S. Pat. Publ. No. 2011/0123532; Int. Pat. Publ. No. WO2011/131746; Int. Pat. Publ. No. WO2011/143545; or U.S. Pat. Publ. No. 2012/0149876. For example, bispecific antibodies of the present disclosure may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody and the second monospecific bivalent antibody are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Example reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

The antigen-binding regions of the bispecific antibody can take any form that allows specific recognition of the target, for example the binding region may be or may include a heavy chain variable domain, an Fv (combination of a heavy chain variable domain and a light chain variable domain), a binding domain based on a fibronectin type III domain (such as from fibronectin, or based on a consensus of the type III domains from fibronectin, or from tenascin or based on a consensus of the type III domains from tenascin, such as the Centyrin molecules from Janssen Biotech, Inc., see e.g. WO2010/051274 and WO2010/093627). Accordingly, bispecific molecules comprising two different antigen-binding regions which bind the linker peptide and another antigen, are provided.

Different formats of bispecific antibodies have been described and were recently reviewed by Chames and Baty (2009) Curr Opin Drug Disc Dev 12: 276.

In some embodiments, the bispecific antibody of the present disclosure is a diabody, a cross-body, or a bispecific antibody obtained via a controlled Fab arm exchange as those described in the present invention.

In some embodiments, the bispecific antibodies include IgG-like molecules with complementary CH3 domains to force heterodimerization; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody)(EMD Serono), the Biclonic (Merus) and the DuoBody (Genmab A/S).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES (Biogen Idec) and TvAb (Roche).

In some embodiments, Fc fusion molecules include to ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv).sub.2-Fab (National Research Center for Antibody Medicine-China).

In some embodiments, Fab fusion bispecific antibodies include F(ab)2 (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based and domain antibodies include but are not limited to Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, Receptor-Logics), Human Serum Albumin ScFv Fusion (Merrimack) and COMBODY (Epigen Biotech), dual targeting nanobodies (Ablynx), dual targeting heavy chain only domain antibodies.

Full length bispecific antibodies of the present disclosure may be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each bind a distinct epitope.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Intl. Publ. No. WO 2006/028936) may be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S L368A Y407V.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by the following substitutions (expressed as modified position in the first CH3 domain of the first heavy chain/modified position in the second CH3 domain of the second heavy chain): L351Y_F405AY407V/T394W, T366IK392M T394W/F405A Y407V, T366L_K392M T394W/F405A Y407V, L351Y_Y407A/T366A_K409F, L351Y_Y407A/T366V K409F Y407A/T366A_K409F, or T350V_L351Y_F405A Y407V/ T350V_T366L_K392L_T394W as described in U.S. Pat. Publ. No. US2012/0149876 or U.S. Pat. Publ. No. US2013/0195849.

In some embodiments, the anti-linker antibody, or antigen binding fragments thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, scintillates, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases, the detectable label emits a signal as a result of being stimulated by an external field. Suitable dyes include any commercially available dyes such as, for example, 5(6)-carboxyfluorescein, IRDye 680RD maleimide or IRDye 800CW, ruthenium polypyridyl dyes, and the like. Suitable fluorophores are fluorescein isothiocyanate (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

Methods of Using Linker-Specific Antibodies

Provided herein are linker-specific antibodies or antigen-binding fragments thereof for use in biological detection and measurement. In particular, these antibodies or antigen-binding fragments may be useful in detecting a polypeptide comprising a linker peptide comprising the amino acid sequence of GGSEGKSSGSGSESKSTGGS (SEQ ID NO: 98) in a sample. Accordingly, the present disclosure provides a method of detecting a polypeptide comprising a linker peptide comprising the amino acid sequence of GGSEGKSSGSGSESKSTGGS (SEQ ID NO: 98) in a sample, which may include (i) contacting the sample with an isolated antibody or antigen-binding fragment described herein, and (ii) detecting the binding of the polypeptide to said isolated antibody or antigen-binding fragment. The antibodies for use in these methods include those described herein above, for example a linker-specific antibody or antigen-binding fragment with the features set out in Tables 1 or 2, for example the CDRs or variable domain sequences, and in the further discussion of these antibodies.

Also provided herein is a method of measuring the amount of a polypeptide comprising a linker peptide comprising the amino acid sequence of GGSEGKSSGSGSESKSTGGS (SEQ ID NO: 98) in a sample. In some embodiments, the method includes (i) contacting the sample with the isolated antibody or antigen-binding fragment described herein, and (ii) quantitating the binding of the polypeptide to said isolated antibody or antigen-binding fragment. Such method may further comprises comparing the binding measured in step (ii) to a control value. In some embodiments, the control value is a predetermined value (e.g., standard curve). The antibodies for use in these methods include those described herein above, for example a linker-specific antibody or antigen-binding fragment with the features set out in Tables 1 or 2, for example the CDRs or variable domain sequences, and in the further discussion of these antibodies.

In some embodiments, the sample may be a liquid composition comprising a polypeptide comprising a linker peptide comprising the amino acid sequence of GGSEGKSSGSGSESKSTGGS (SEQ ID NO: 98). In some embodiments, the polypeptide is an antibody, antigen-binding fragment, or a chimeric antigen receptor (CAR). The antibody or antigen-binding fragment may be, for example, a human antibody, a monoclonal antibody, a single chain antibody, a Fab, a Fab', a F(ab')2, a Fv, or a scFv. In a particular embodiment, the polypeptide to be analyzed is an scFv. In some embodiments, the polypeptide to be analyzed is a multi-specific antibody or antigen-binding fragment. In a particular embodiment, the polypeptide to be analyzed is a bispecific antibody or antigen-binding fragment. In a particular embodiment, the polypeptide to be analyzed is a chimeric antigen receptor (CAR). The CAR may be presented on an immune cell, such as a T cell or a NK cell.

In some embodiments, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like.

In some embodiments the sample may be contacted with more than one of the linker-specific antibodies or antigen-binding fragments described herein. For example, a sample may be contacted with a first linker-specific antibody, or antigen-binding fragment thereof, and then contacted with a second linker-specific antibody, or antigen-binding fragment thereof, wherein the first antibody or antigen-binding fragment and the second antibody or antigen-binding fragment are not the same antibody or antigen-binding fragment. In some embodiments, the first antibody, or antigen-binding fragment thereof, may be affixed to a surface, such as a multiwell plate, chip, or similar substrate prior to contacting the sample. In other embodiments the first antibody, or antigen-binding fragment thereof, may not be affixed, or attached, to anything at all prior to contacting the sample.

In some aspects, affinity matrices comprising the isolated antibody or antigen-binding fragment described herein are also provided. The described linker-specific antibodies and antigen-binding fragments may be immobilized by attachment to a suitable solid support. Examples of solid supports include, but are not limited to, a bead, a membrane, sepharose, a magnetic bead, a plate, a tube, a column. The described linker-specific antibodies and antigen-binding fragments may be attached to an ELISA plate, a magnetic bead, or a surface plasmon resonance biosensor chip. Methods of attaching antibodies and antigen-binding fragments to a solid support are known to the skilled person, and include, for example, using an affinity binding pair, e.g. biotin and streptavidin, or antibodies and antigens, or using covalent linkages.

The described linker-specific antibodies and antigen-binding fragments may be detectably labeled. In some embodiments labeled antibodies and antigen-binding fragments may facilitate the detection of the linker peptide of interest (e.g., SEQ ID NO: 98) via the methods described herein. Many such labels are readily known to those skilled in the art. For example, suitable labels include, but should not be considered limited to, radiolabels, fluorescent labels, epitope tags, biotin, chromophore labels, ECL labels, or enzymes. More specifically, the described labels include ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like.

The described linker-specific antibodies and antigen-binding fragments may be used in a variety of assays to detect the linker peptide of interest (e.g., SEQ ID NO: 98) in a sample. Some suitable assays include, but should not be considered limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Kits

Provided herein are kits for detecting a linker peptide of interest (e.g., SEQ ID NO: 98) in a biological sample. These kits may include one or more of the linker-specific antibodies described herein, or an antigen-binding fragment thereof, or a polynucleotide or vector encoding same, and instructions for use of the kit.

The provided linker-specific antibody, or antigen-binding fragment, may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for measuring the amount of a polypeptide comprising a linker peptide of SEQ ID NO: 98 can further include, for example, buffers or other reagents for use in an assay for quantitating the binding of the polypeptide to said isolated antibody or antigen-binding fragment. The instructions can be, for example, printed instructions for performing the assay and/or instructions for evaluating the amount of the polypeptide.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample.

Methods of Generating Antibodies Against an Immunorecessive Epitope

Methods of generating an antibody that specifically binds to an immunorecessive epitope are provided herein. Such methods may include one or more of the following steps:
a) immunizing an adult animal with one or more (e.g., 1, 2, 3, 4, 5, 6 or more) tolerogens,
b) administering to the adult animal an agent that selectively kills rapidly proliferating lymphocytes,
c) immunizing the adult animal with one or more (e.g., 1, 2, 3, 4, 5, 6 or more) immunogens, each of said immunogens comprising the immunorecessive epitope conjugated to one of the tolerogens used in step (a),
d) obtaining B lymphocytes from the adult animal after step (c),
e) screening hybridomas or an antibody library generated from the B lymphocytes obtained in step (d) for a candidate antibody which specifically binds to the immunorecessive epitope; and
f) isolating the antibody identified in step (e) as specifically binding to the immunorecessive epitope.

In some embodiments, step (c) comprises, after the initial immunization, administering to the adult animal one or more booster doses of said immunogen or of an immunogen comprising the immunorecessive epitope conjugated to a different tolerogen used in step (a). The booster doses may be administered at an amount sufficient to raise the antibody titer to the immunogens and/or increase the immigration of plasma cells secreting antibodies to immunogens into the spleen of the animal. In some embodiments, after the initial immunization, 1, 2, 3, 4, 5, 6, or more booster doses are administered. In some embodiments, after the initial immunization, 3 booster doses are administered. In some embodiments, after the initial immunization, 4 booster doses are administered. In some embodiments, the booster doses may be administered at about 1 week, about 2 weeks, about 3 weeks, about 4 weeks, 1 month, about 5 weeks, about 6 weeks, about 7 weeks, about 8 weeks, 2 months, about 9 weeks, about 10 weeks, about 11 weeks, about 12 weeks, or 3 months after the initial immunization. In an exemplary embodiment, the initial immunization is performed with a dose of an immunogen comprising the immunorecessive epitope conjugated to one of the tolerogens, which is followed by three boosters each comprising the same immunorecessive epitope conjugated to each of the tolerogens used in step (a) and a pre-fusion booster comprising a mixture of the same immunorecessive epitope conjugated to each of the tolerogens used in step (a).

An agent that selectively kills rapidly proliferating lymphocytes can be administered after the animal is immunized with tolerogens. The agent for use in the methods of the present disclosure can be one that inhibits growth of rapidly proliferating immune cells including clones of B lymphocytes and T lymphocytes. Thus, the B lymphocytes which are producing antibodies to the tolerogens and therefore are rapidly dividing, are depleted from the system. Appropriate agents which are capable of selectively killing rapidly replicating/dividing cells include any cytostatic or cytotoxic compound or drug, for example, drugs used in chemotherapy which have as their mode of action the prevention of cell growth or the killing of rapidly dividing cells. Exemplary compounds suitable for use in methods of the present disclosure include those of the classes alkylating agents, antimetabolites, anthracyclines, topoisomerase inhibitors, cytotoxic antibiotics, and natural products. Examples of such compounds include, but are not limited to, cisplatin, carboplatin, oxaliplatin, cyclosporine A, mycophenolate, mofetil, azathioprine, tacrolimus, leflunomide, mycophenolic acid, melphalan, chlorambucil, methotrexate, fluorouracil, vincristine, busulfan, mechlorethamine, chlorambucil, ifosfamide, cyclophosphamide, *vinca* alkaloids and taxanes such as paclitaxel (Taxol) and docetaxel, type I topoisomerase inhibitors such as camptothecins, e.g. irinotecan and topotecan, and type II topoisomerase inhibitors such as amsacrine, etoposide, etoposide phosphate, and teniposide. In one embodiment, cyclophosphamide is used as the agent in the methods of the present disclosure.

In some embodiments, the agent that selectively kills rapidly proliferating lymphocytes may be administered more than once, e.g., twice, three times, four times, or more. In some embodiments, the agent that selectively kills rapidly proliferating lymphocytes may be administered three times. In some embodiments, the multiple doses of the agent that selectively kills rapidly proliferating lymphocytes may be administered in 8 hours, 12 hours, 16 hours, 24 hours, 30 hours, 36 hours, 42 hours, or 48 hours intervals. In some embodiments, the agent that selectively kills rapidly proliferating lymphocytes may be administered at 10 min, 30 min, 1 hour, 8 hours, 12 hours, 16 hours, 24 hours, 30 hours, 36 hours, 42 hours, 48 hours, 60 hours, 72 hours, 4 days, 5 days, 6 days, 1 week, or 10 days after tolerogen induction. The dose of the agent is selected such that it is high enough to be able to exert its cytotoxic effect on B cells but is not so high as to cause unacceptable toxicity or side effects to the animal. In an exemplary embodiment described herein, cyclophosphamide is administered at 100 mg/kg body weight of the animal and administered at 3 different time points—10 mins, 24 hours and 48 hours after tolerogen induction. This dose and administration schedule was found to give clean tolerogen-free, healthy animal models for study. The does may be adjusted as long as such doses are high enough to be able to exert its cytotoxic effect on B cells but not so high to cause unacceptable toxicity or side effects to the animal. For example, doses such as about 70 mg/kg, about 80 mg/kg, about 90 mg/kg, about 110 mg/kg, about 120 mg/kg, or about 150 mg/kg body weight of the animal may be used.

Once the lymphocytes reactive to the tolerogens have been depleted, the animal is then immunized with one or more immunogens (step (c) of the method), each of which comprises the immunorecessive epitope conjugated to one of the tolerogens used in step (a). Although not wishing to be bound by theory, it is believed that in this step, the only B cells which are stimulated to replicate (or at least a significant proportion of the B cells which are stimulated to replicate) will be those that recognize the difference between the tolerogens and the immunogens (i.e., the immunorecessive epitope). In this way B cells producing antibodies which discriminate between the tolerogens and the immunogens are produced and antibodies which can bind to the immunogens but not the tolerogens can be generated.

The immunorecessive epitope for use in the method of the present application can comprise or consist of any molecules which can be recognized as foreign by the immune system of the animal used and which will result in an immune response being initiated and the production of antibodies. This difference between the tolerogens and immunogens can be very small, for example can be a few amino acids in length, as it is believed that the sensitivity of the method means that antibodies can be generated which will discriminate between tolerogens and immunogens with only minor differences in the structure.

In some embodiments, the immunorecessive epitope is a short peptide of less than about 50 amino acids in length. In some embodiments, the immunorecessive epitope is a short peptide of about 6-40 amino acids, about 8-35 amino acids, about 10-20 amino acids, about 10-30 amino acids, about 15-25 amino acids, or about 20 amino acids. In some embodiments, the immunorecessive epitope is a short peptide of 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids, or 25 amino acids in length. In one embodiment, the immunorecessive epitope is a short peptide of about 14 amino acids in length. In one embodiment, the immunorecessive epitope is a short peptide of about 20 amino acids in length. In one specific embodiment, the immunorecessive epitope is the linker peptide of SEQ ID NO: 98, or a fragment thereof.

In some embodiments, tolerogens used in the method of the present disclosure comprise a carrier protein. Examples of carrier proteins suitable for use in the methods of the present disclosure include, but are not limited to, ovalbumin (OVA), keyhole limpet haemocyanin (KLH), blue carrier protein (BCP), thyroglobulin (THY), a soybean trypsin inhibitor (STI), and multiple attachment peptide (MAP), albumin, serum albumin, bovine serum albumin (BSA), c-reactive protein, conalbumin, lactalbumin, ion carrier protein, acyl carrier protein, signal transduction adapter protein, androgen binding protein, calcium binding protein, calmodulin binding protein, ceruloplasmin, cholesterol Ester transfer protein, f box protein, fatty acid binding protein, follistatin, follistatin related protein, GTP binding protein, insulin-like growth factor binding protein, iron binding protein, latent TGFbeta binding protein, light-harvesting protein complex, lymph Sphere antigen, membrane transport protein, neurophysin, periplasmic binding protein, phosphate binding protein, phosphatidylethanolamine binding protein, phospholipid transport protein, retinol binding protein, RNA binding protein, s-phase kinase related protein, sex hormone binding globulin, Thyroxine binding protein, transcobalamin, transcortin, transferrin binding protein, and/or vitamin D binding protein.

As described above, splenocytes are obtained from an immunized animal and are fused with myeloma cells or transformed cells capable of replicating indefinitely in culture to yield a hybridoma. Methods of producing hybridomas are well known in the art and include for example, those procedures described in Kohler and Milstein (1975) and Pytowski (1988), the disclosures of which are incorporated by reference herein in its entirety. Individual hybridoma cells are cloned and the clones are tested for production of antibodies. For example, hybridoma supernatants may be screened for antigen-specific antibody reactivities. Once a hybridoma cell line producing antibodies that react with antigens is identified, the cells may be frozen and stored ensuring long-term supply. Such cell lines may be subsequently thawed when more antibody is required, ensuring long-term supply.

The animal to be used in the methods of the present disclosure can be any animal which is capable of mounting an immune response to the antigen of interest. Preferred animals are thus non-human animals or mammals. Any livestock, domestic or laboratory animal can be used. Specific examples include rodents (e.g. rats, mice, guinea pigs, hamsters), ferrets, rabbits, llamas, sheep, pigs, cows, dogs, cats and non-human primates. In some embodiments, the animal is a mouse.

EXAMPLES

The following examples are provided to further describe some of the embodiments disclosed herein. The examples are intended to illustrate, not to limit, the disclosed embodiments.

Example 1. Tolerization and Immunization

In the present Example, a tolerization technique to destroy carrier specific lymphocytes and bias the immune system towards responding to the less immunogenic linker peptide was developed. The strategy of tolerization was based on the idea that antigen-responsive proliferating lymphocytes can be preferentially destroyed using chemical alkylating agents such as, but not limited to, cyclophosphamide. Therefore, cyclophosphamide injection following carrier protein tolerization in a timely manner helped to develop a mouse model that was capable of mounting linker-specific immune response upon immunization with linker-carrier conjugates. This adult tolerization approach with carefully designed dose and time regime for administration of cyclophosphamide, as disclosed herein, was easy to operate, had reduced timelines, and provided a system that was devoid of tolerogen specific response.

During immunization and booster dosing, different carrier proteins, ovalbumin (OVA), keyhole limpet haemocyanin (KLH), and blue carrier protein (BCP) conjugated to MSCD331 peptide were alternated to specifically direct the immune response of the pre-tolerized animals towards the peptide. Sera from these animals were assessed intermittently for anti-MSCD331 titer, and the best responding animals were selected for generation of hybrids and monoclones.

Experimental animals for the tolerization and immunization experiments were C57/BL6 female mice obtained at 5 weeks of age. To induce tolerance against different carrier proteins at the adult stage, 25 µg each of KLH, OVA and BCP (Janssen) were mixed in sterile Dulbecco's phosphate buffered saline (DPBS) (GIBCO, 14190-144-500ML), and injected intraperitoneally (i.p.) into 15 C57/BL6 mice. Ten minutes post-tolerization, cyclophosphamide (100 mg/kg body weight) was injected intraperitoneally (i.p.) on day 0. On day 1 and 2, cyclophosphamide was again administered to the mice following a similar method. Following three rounds of cyclophosphamide injection, mice were rested until day 6. On day 7, sera were collected and tested for tolerogen-specific (e.g., OVA, KLH, BCP) responses using enzyme linked immunosorbent assay (ELISA).

For immunization of the tolerized animals, all 15 animals were found to have low or no carrier specific response, and hence were taken forward for immunization. Mice were grouped into 3 cages (Cohort 1-3), each cage containing 5 mice. Primary immunization was performed on day 9 post-tolerization using 80 µg/animal of MSCD331-KLH. This was followed by bi-weekly boosters with intermittent titer checks. A total of three boosters was administered: the first booster was with MSCD331-OVA; the second booster was with MSCD331-BCP; and, the third booster was with MSCD331-OVA. Primary immunization was performed using Freund's complete adjuvant (FCA) (Sigma; F5881-10 mL) followed by the three boosters in Freund's incomplete adjuvant (FIA). (Sigma; F5506-10 mL). Animals in cages 1 and 2 were immunized through a subcutaneous (s.c.) route, while those in cage 3 were immunized via an intraperitoneal (i.p.) route. For the pre-fusion booster, a mixture of MSCD331-KLH, MSCD331-OVA and MSCD331-BCP was prepared in DPBS (Sigma; 14190144) and administered i.p. at 100 µg per animal. Description of an exemplary immunization schedule is provided in Table 3.

TABLE 3

| Immunization schedule | |
|---|---|
| Day | Antigen administration/Titer check |
| Not applicable | Pre immune bleed 1-20 µl of serum; Titer Check using ELISA |
| Not applicable | ELISA for pre-immune sera check |
| Day 0 | 25 µg of KLH, OVA and BCP carrier proteins |
| Day 0-10 mins | Cyclophosphamide 100 mg/kg body weight of mice |

TABLE 3-continued

| Immunization schedule | |
|---|---|
| Day | Antigen administration/Titer check |
| Day 1 | Cyclophosphamide 100 mg/kg body weight of mice |
| Day 2 | Cyclophosphamide 100 mg/kg body weight of mice |
| Day 7 | Pre immune bleed 2-20 µl of serum; Titer Check using ELISA |
| Day 8 | ELISA for tolerization check |
| Day 9 | Primary immunization-80 µg of MSCD331-KLH; Cage 1 and 2 with 5 subcutaneous sites (40 µl per site) and cage 3- Intraperitoneal route with FCA |
| Day 30 | 1st Booster- 80 µg of MSCD331-OVA with IFA adjuvant |
| Day 37 | 1st Bleed- ELISA for titer check using Biotinylated-MSCD331 |
| Day 47 | 2nd Booster- 80 µg of MSCD331-BCP with FIA |
| Day 54 | 2nd Bleed- ELISA for titer check using Biotinylated-MSCD331 |
| Day 61 | 3rd Booster- 80 µg of MSCD331-OVA with FIA adjuvant |
| Day 68 | 3rd Bleed- FACS and ELISA for titer check |
| Day 76 | Pre fusion booster- 100 µg of MSCD331-KLH, OVA and BCP in PBS; Intraperitoneal site (200 µl) |
| Day 79 | Fusion with Sp2/0 IL6 cells |

Figure 2A:
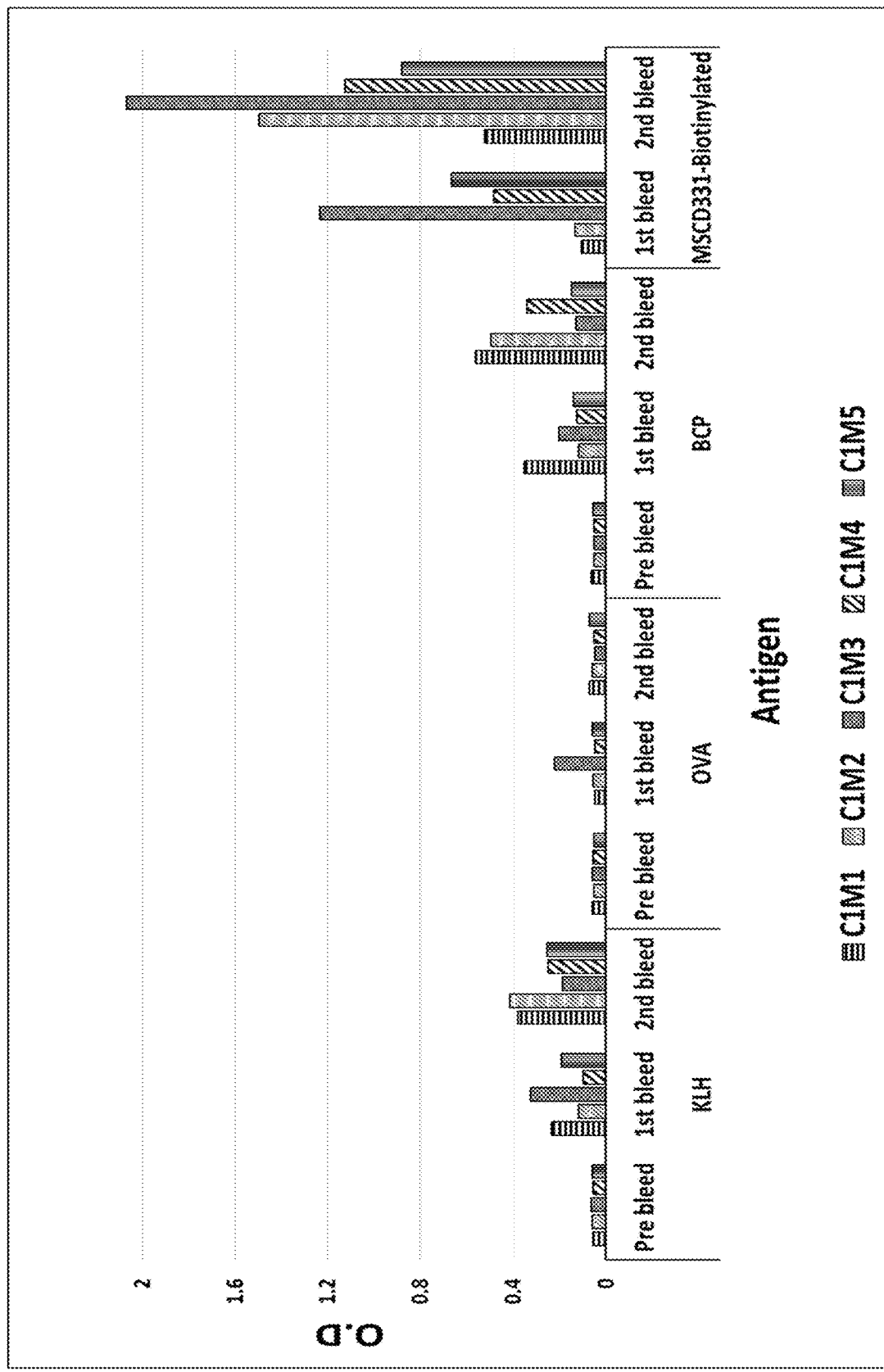
FIGS. 2A-2C demonstrate sera from tolerized animals showing low reactivity to tolerogens (e.g., KLH, OVA, BCP), but high reactivity to immunogen (MSCD331) after the second booster. For generation of these data, pre-bleed, first bleed, and second bleed sera from animals were diluted 1:1000 in assay diluent and estimated for KLH, OVA, BCP and MSCD331-specific responses by enzyme-linked immunosorbent assay (ELISA).
Figure 2B:
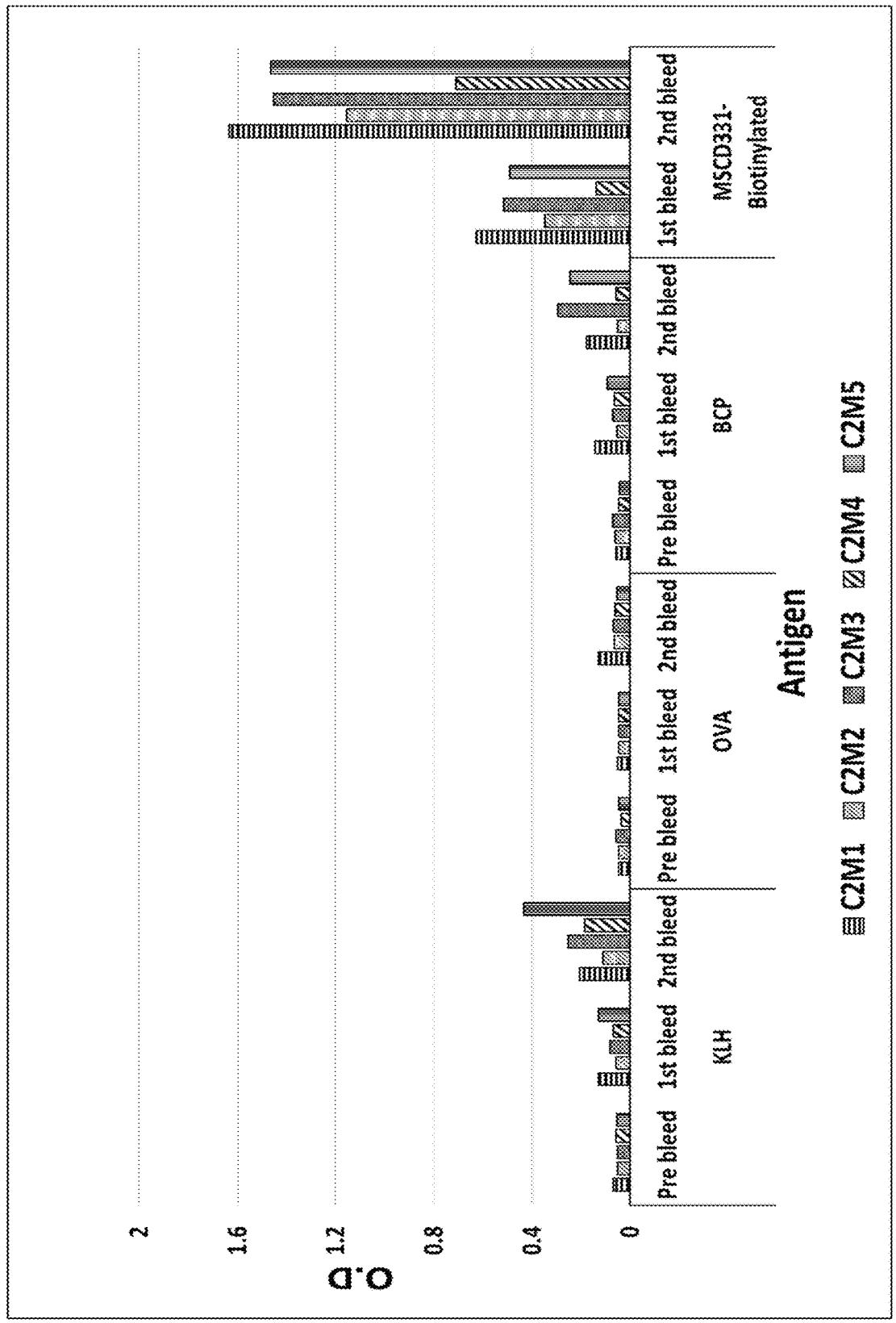
Figure 2C:
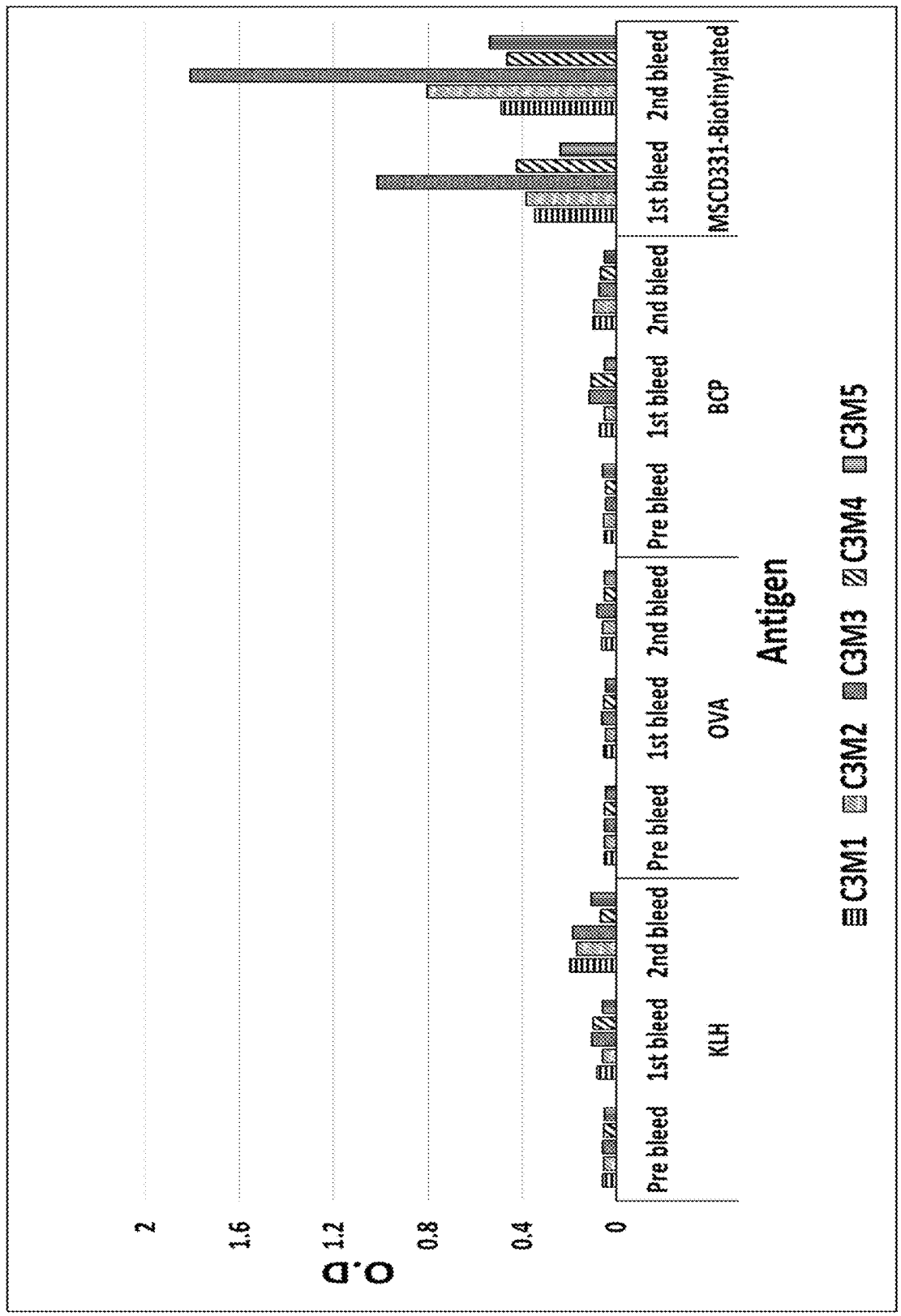

For the ELISA for the determining tolerization and immunization, 96-well microtiter plates (Nunc, 456537) were coated with 1 µg/ml of KLH, OVA, BCP and MSCD331-biotin diluted in DPBS and incubated overnight at 4° C. Plates were then washed with PBS and blocked using 500 non-fat dry milk (Chem cruz, SC-2325) for 1 hour at room temperature. Sera were added to the blocked plates diluted in DPBS and incubated for 2 hours at 37° C. Plates were washed with PBS containing 0.050% of Tween-20 (SIGMA, P2287-500 ml) and bound IgG was detected using Goat anti-Mouse IgG horseradish peroxidase (HRP) (R&D Systems, HAF007) prepared in 1% bovine serum albumin (BSA) (Hi-media, MB083-100 gm). After 1 hour, plates were washed and developed using 3,3',5,5'-Tetramethylbenzidine (TMB) substrate (SIGMA, T4444-100 ml). The reaction was stopped using 2N $H_2SO_4$ and the absorbance (optical density, O.D.) was measured at 450 nm. FIG. 1 demonstrates sera from animals on day 7 post tolerization showing no binding to tolerogens. For generation of these data, sera from tolerized animals were diluted 1:100 in assay diluent and plated onto KLH, OVA and BCP coated plates to determine presence of any tolerogen specific titer. The sera titers were compared to secondary alone control. FIGS. 2A-C demonstrate sera from tolerized animals showing low reactivity to tolerogens (KLH, OVA, BCP), but high reactivity to immunogen (MSCD331) after the second booster. For generation of these data, pre-bleed, first bleed, and second bleed sera from animals were diluted 1:1000 in assay diluent, and estimated for KLH, OVA, BCP and MSCD331-specific responses ELISA. FIG. 2A displays ELISA data obtained from the first animal cohort (Cohort 1); FIG. 2B displays ELISA data obtained from the second animal cohort (Cohort 2); and, FIG. 2C displays ELISA data obtained from the third animal cohort (Cohort 3).

Figure 3A:
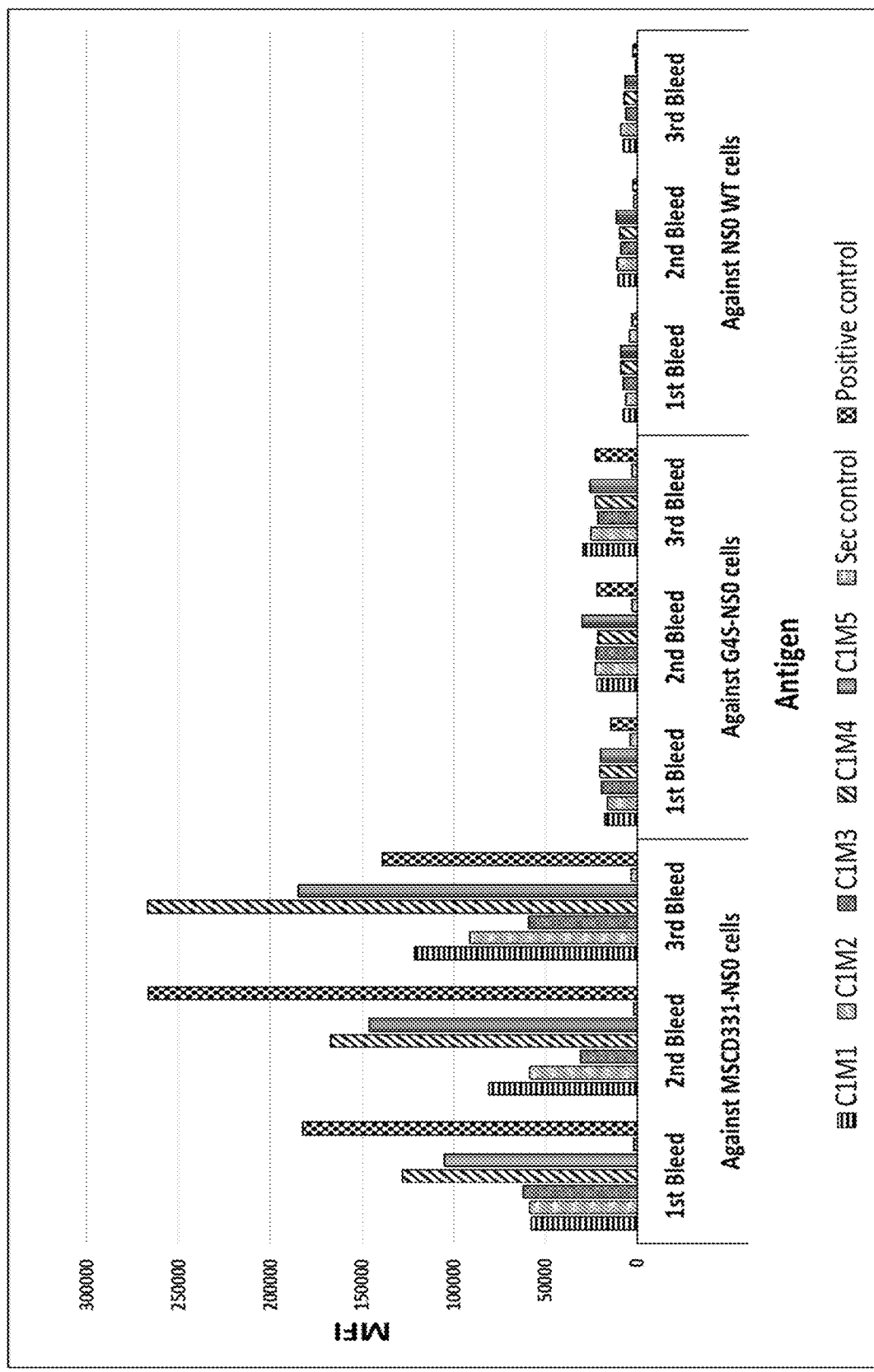
FIGS. 3A-3C demonstrate sera from tolerized animals showing MSCD331 specific response following immunization. For generation of these data, sera from first bleed, second bleed, and third bleed of tolerized animals were diluted 1:100 in FACS buffer and checked for binding to NS0 wild type (WT) cells and NS0 cells over-expressing chimeric antigen receptor (CAR)-bearing MSCD331 or (G4S)4 linker (SEQ ID NO: 99) using flow cytometry. Secondary (sec) antibody and positive compound binding on the cell lines are also shown. Signal was measured as mean fluorescence intensity (MFI).
Figure 3B:
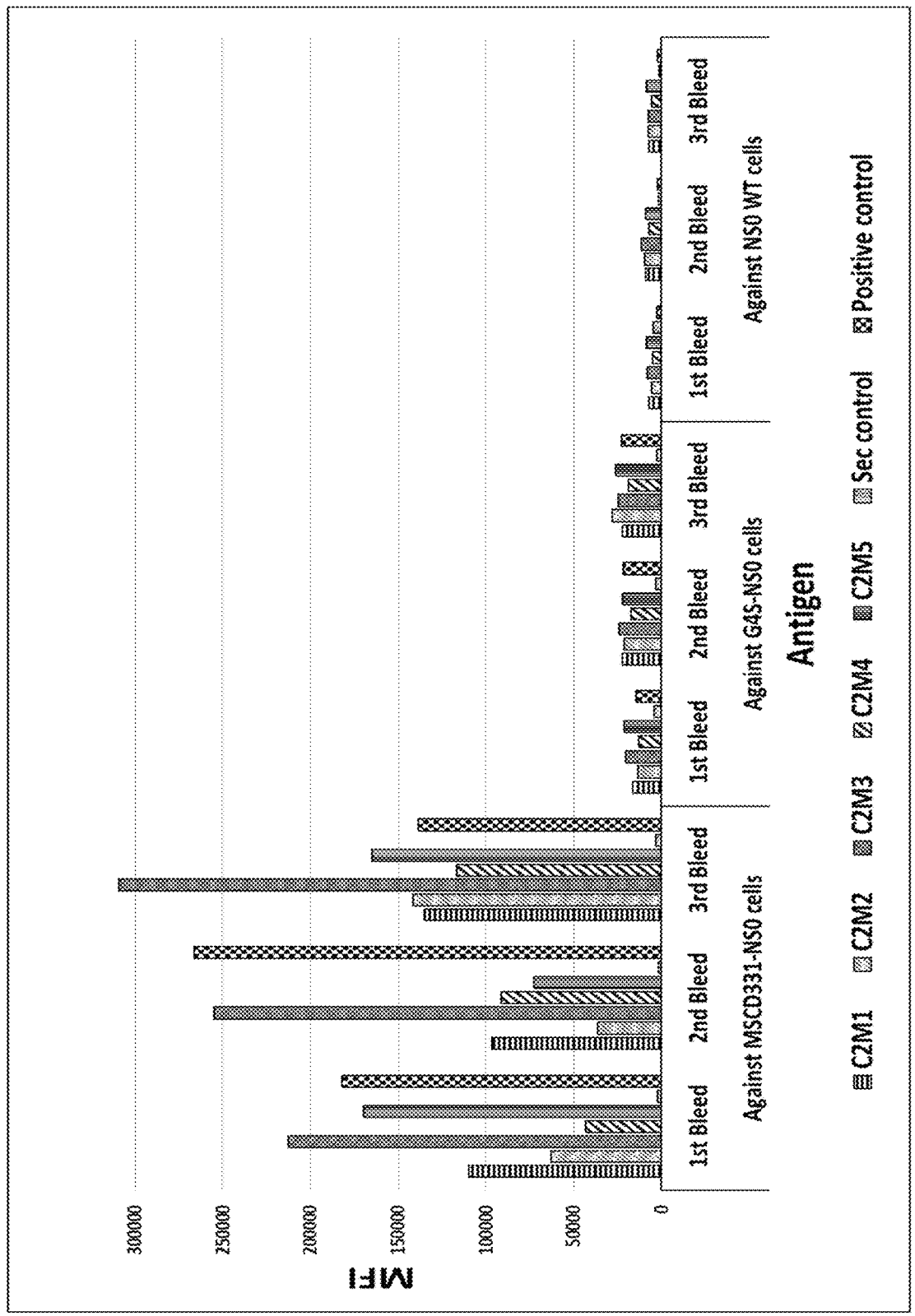
Figure 3C:
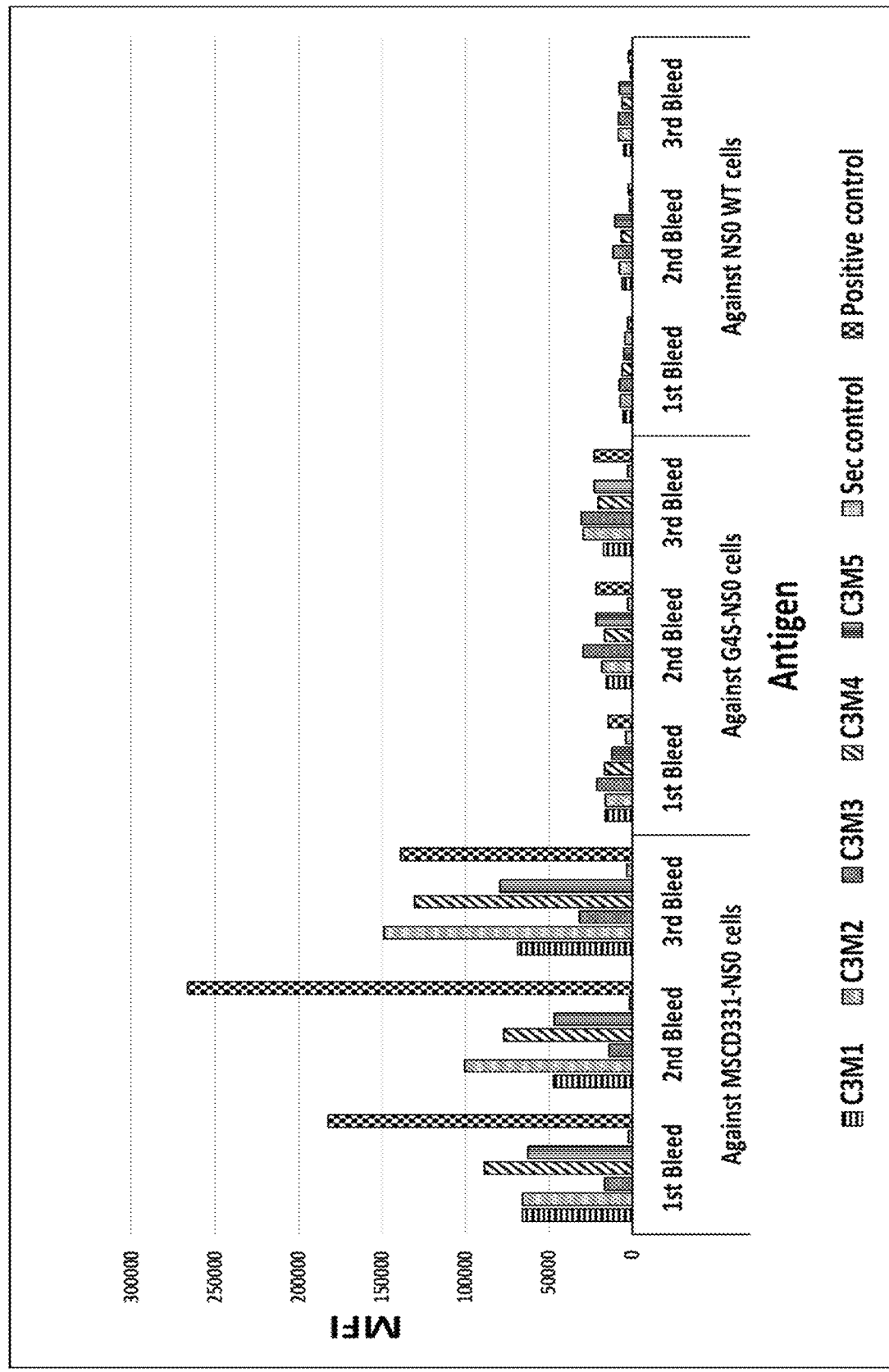

Flow cytometry was used to confirm anti-MSD331 specific titer. Briefly, NS0 cell lines over-expressing CAR with a MSCD331 linker were used for screening sera from immunized animals. Wild type (WT) NS0 cells and NS0 cells over-expressing CAR with (G4S)4 linker (SEQ ID NO: 99) were used as counter-screening tools. A compound, CD9b137-LH conjugated to Alexa fluor 647 was used to confirm expression of CAR on the NS0 lines. Cells were incubated with sera diluted 1:100 in FACS buffer (DPBS containing 2% FBS [fetal bovine serum]) followed by addition of Goat anti-Mouse IgG conjugated to phycoerythrin (PE) (Southern Biotech; 1030-09). Cells were washed and acquired on Acea Novocyte cytometer. FIGS. 3A-3C demonstrate sera from tolerized animals showing MSCD331-specific response following immunization. For generation of these data, sera from first bleed, second bleed, and third bleed of tolerized animals were diluted 1:100 in FACS buffer, and assessed for binding to NS0 wild type (WT) cells and NS0 cells over-expressing CAR bearing MSCD331 or (G4S)4 linker (SEQ ID NO: 99) via flow cytometry. FIG. 3A displays flow cytometry data obtained from first animal cohort (Cohort 1); FIG. 3B displays flow cytometry data obtained from the second animal cohort (Cohort 2); and, FIG. 3C, displays flow cytometry data obtained from the third animal cohort (Cohort 3).

Figure 4:
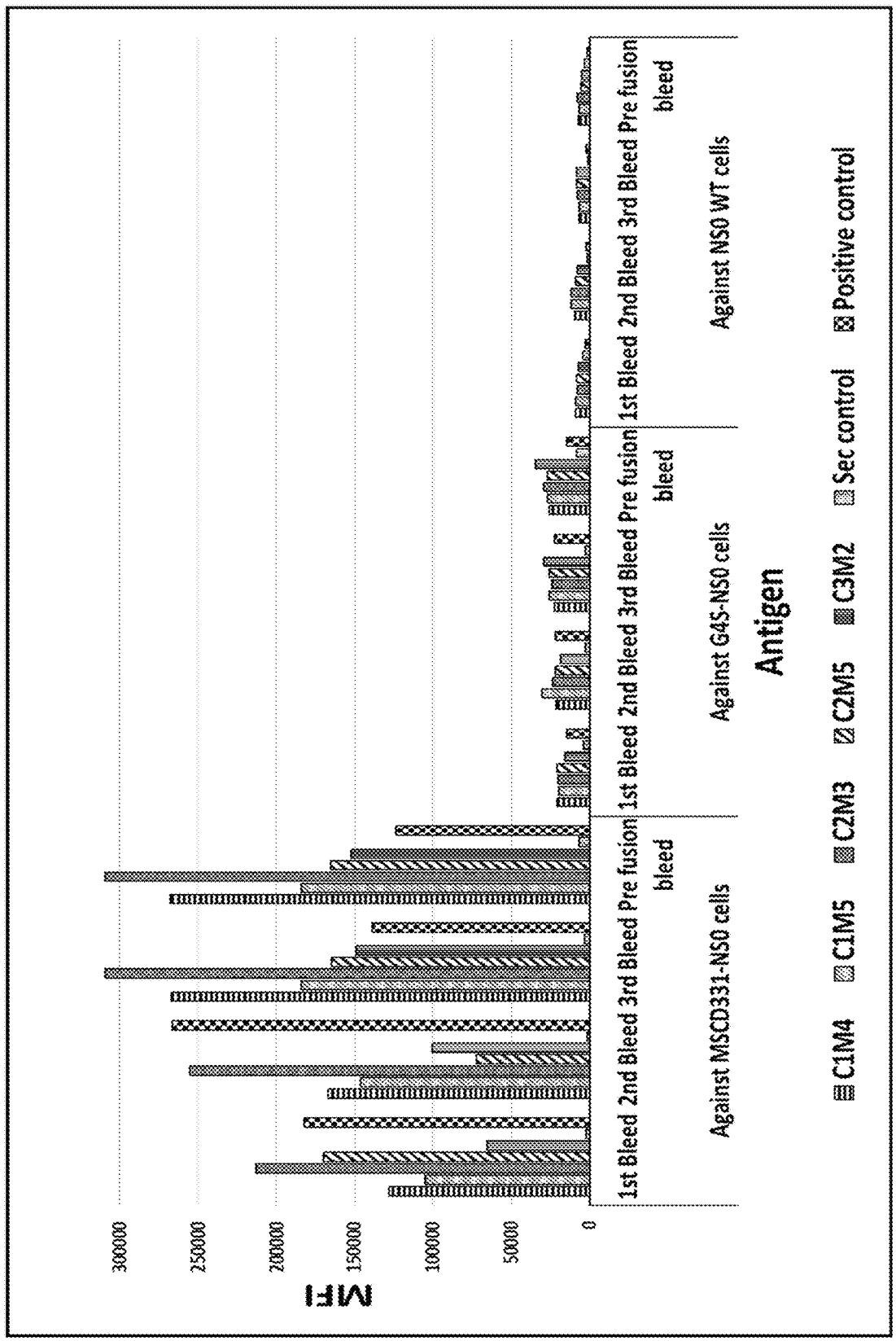
FIG. 4 shows flow cytometry data compiled for 5 selected animals. For generation of these data, animals C1M4 (Cohort 1, Mouse 4) and C1M5 (Cohort 1, Mouse 5) from the first animal cohort (Cohort 1), C2M3 (Cohort 2, Mouse 3) and C2M5 (Cohort 2, Mouse 5) from the second animal cohort (Cohort 2), and C3M2 (Cohort 3, Mouse 2) from the third animal cohort (Cohort 3) were the best responders, with titers constant between third bleed and prefusion bleed, and hence, these animals were used for subsequent monoclone generation. Signal was measured as mean fluorescence intensity (MFI). Figure discloses "G4S" as SEQ ID NO: 100.

Flow cytometry data were lastly compiled for 5 selected animals, as shown in FIG. 4. For generation of these data, animals C1M4 (Cohort 1, Mouse 4) and C1M5 (Cohort 1, Mouse 5) from the first animal cohort (Cohort 1), C2M3 (Cohort 2, Mouse 3) and C2M5 (Cohort 2, Mouse 5) from the second animal cohort (Cohort 2), and C3M2 (Cohort 3, Mouse 2) from the third animal cohort (Cohort 3) were the best responders, with titers constant between third bleed and prefusion bleed, and hence, these animals were used for subsequent monoclone generation.

Example 2. Screening to Identify MSCD331 Specific Monoclones

The present Example involved generation of diverse monoclonal antibodies against the MSCD331 linker with subsequent determination of their epitope-recognizing ability using different screening reagents. These reagents included scFv-Fc fusion proteins, bispecific antibodies bearing scFv in both arms/one arm, CAR-expressing cell lines, as well as purified CAR-ECD (extra-cellular domain) proteins. For determining the specificity of these monoclones, scFv having the same VH and VL chain, but bearing a different linker, (G4S)4 (GGGGSGGGGSGGGGSGGGGS; SEQ ID NO: 99), was used. MSCD331 and (G4S)4 linkers (SEQ ID NOs: 98 and 99) have the same length, but differ in their amino acid sequence. Hence, (G4S)4 (SEQ ID NO: 99) bearing scFv and CAR molecules served as important counter-screening tools in the identification of highly-specific anti-MSCD331 monoclones. For determining universality of epitope recognition for these monoclones, various CARs having different VH and VL chains but bearing the same MSCD331 linker were used.

The antigens used for screening to identify MSCD331 specific monoclones were scFv-Fc fusion protein with MSCD331 linker, bispecific antibodies having scFv on single arm—VG53 (Vδ2*Null), VG56 (Vδ2*CD33), VG65 (Vγ9*Null) and VG68 (Vγ9*CD33) or on both arms—VG51 (Vγ9*Null) and VG52 (Vγ9*CD123) and his-tagged CAR-ECD proteins, CD9B441-HL-ScFv-HSA-His (A003W10) and GP5B83-HL-ScFv-HSA-His (GC5W47) both having the MSCD331 linker were used for screening. A non-specific his-tagged protein, CD70 (CD70-His), and scFv-Fc fusion protein having the (G4S)4 linker (SEQ ID NO: 99) were used for counter-screening. The cell lines used for flow-cytometry based-screening as described below were NS0 and sup-T1 cell lines over-expressing CAR (CD9B137-LH) bearing either MSCD331 or (G4S)4 linkers (SEQ ID NOs: 98 or 99).

For generation of anti-MSCD331 specific monoclones, animals tolerized with different carrier proteins, e.g., KLH, BCP and OVA, and subsequently immunized with MSCD331 coupled to these carrier proteins were assessed for anti-MSCD331 specific titer in sera. Splenocytes from the best responder animals that showed high anti-MSCD331 titer (as in Example 1) were harvested and fused with SP2/0 myeloma cells. Once generated, hybrids were expanded in 24-well and 6-well tissue culture plates to assess stability, and at each step of expansion, were screened by flow cytometry using NS0 cells expressing the CD79b specific CAR, CD9B137-LH, bearing the MSCD331 linker. At the 6-well plate stage, hybrids were also counter-screened using NS0 cells expressing the CD9B137-LH CAR having a different linker, (G4S)4 (SEQ ID NO: 99). Hybrids that showed specific binding to the MSCD331-CAR bearing NS0 cells were subjected to limiting dilution to generate monoclones. The monoclones were likewise screened at different stages of expansion and the final set of monoclones were analyzed against a wide variety of reagents to confirm their specificity to MSCD331, and their universality in recognizing MSCD331, in the context of different bispecifics and CAR molecules.

Figure 7A:
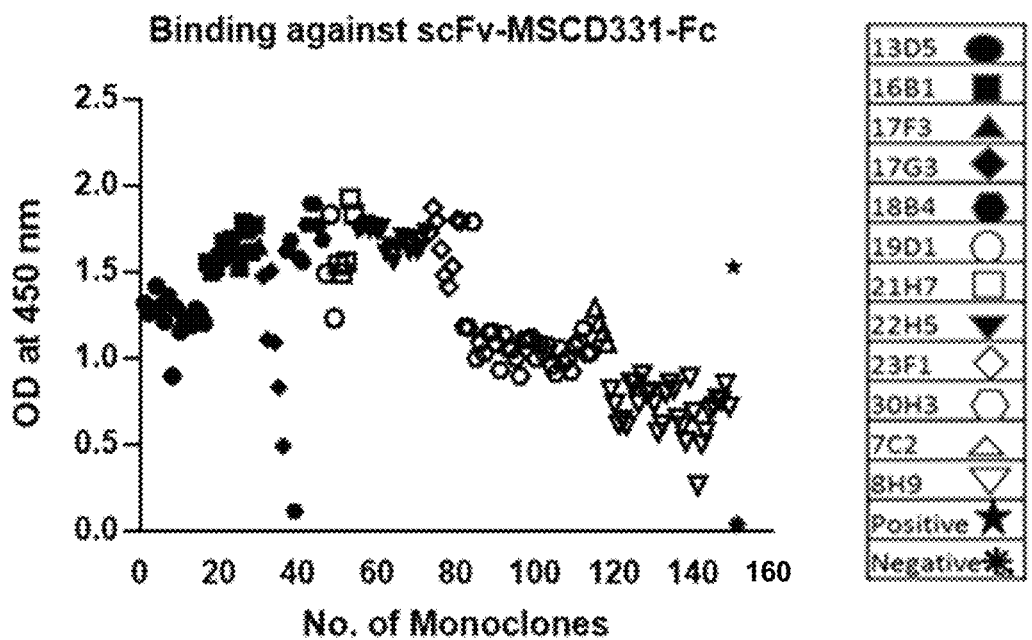
FIGS. 7A-7B demonstrate monoclones specifically binding to MSCD331, but not to (G4S)4 linker (SEQ ID NO: 99) in an ELISA-based assay. To generate these data, supernatants from monoclone cultures were screened on scFv-Fc fusion proteins with either MSCD331 (FIG. 7A) or (G4S)4 linker (SEQ ID NO: 99) (FIG. 7B). Monoclones derived from different hybrid parents are indicated by different shapes, as summarized in the reference table. Binding of MSCD331 specific sera (positive) and secondary antibody alone (negative) controls have been indicated. The absorbance (optical density, O.D.) was measured at 450 nm. Figure discloses "G4S" as SEQ ID NO: 100.
Figure 7B:
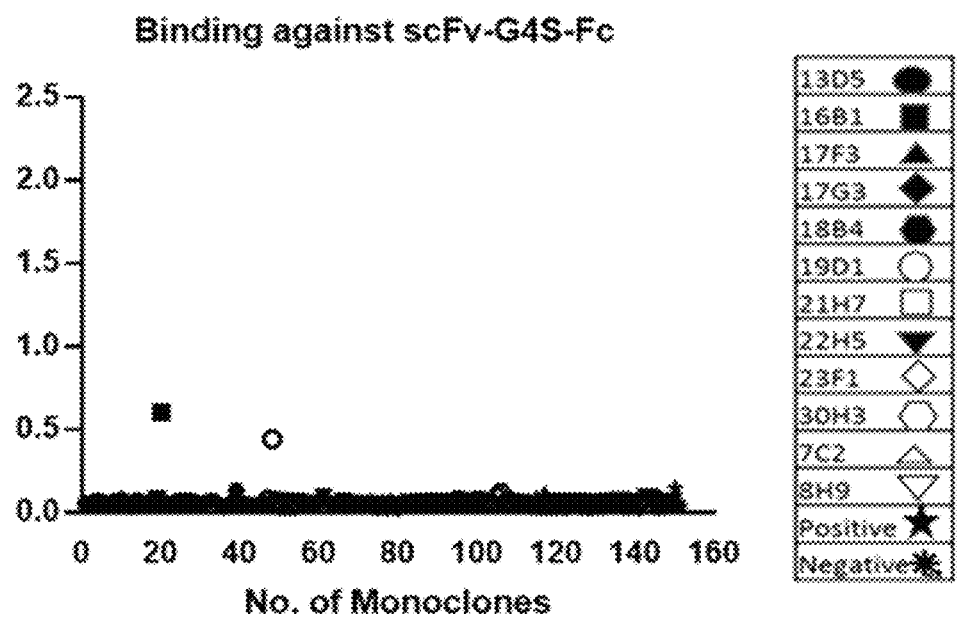
Figure 8A:
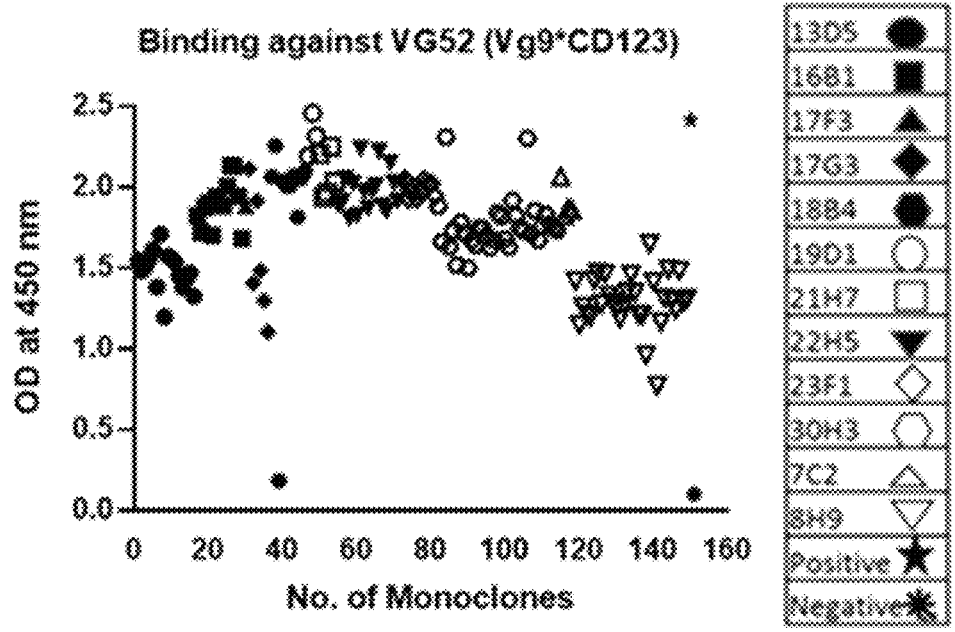
FIGS. 8A-8F demonstrate monoclone recognition of MSCD331 in different bispecific antibodies. Monoclone recognition of MSCD331 is shown in the following exemplar bispecific antibodies: VG52 (Vγ9*CD123), as shown in FIG. 8A; VG51 (Vγ9*Null), as shown in FIG. 8B; VG53 (Vδ2*Null), as shown in FIG. 8C; VG65 (Vγ9*Null), as shown in FIG. 8D; VG56 (Vδ2*CD33), as shown in FIG. 8E; and, VG68 (Vγ9*CD33), as shown in FIG. 8F. Notably, these bispecific antibodies had MSCD331 linker bearing scFv with different target specificities either in both arms (as in FIG. 8A-8B) or in one arm (as in FIGS. 8C-8F). For these experiments, supernatants from monoclone cultures were screened on bispecific antibody coated plates using an ELISA-based approach. Monoclones derived from different hybrid parents are indicated by different shapes, as summarized in the reference table. Binding of the MSCD331 specific sera (positive) and secondary antibody alone (negative) controls to the cell lines are also shown. The absorbance (optical density, O.D.) was measured at 450 nm.
Figure 8B:
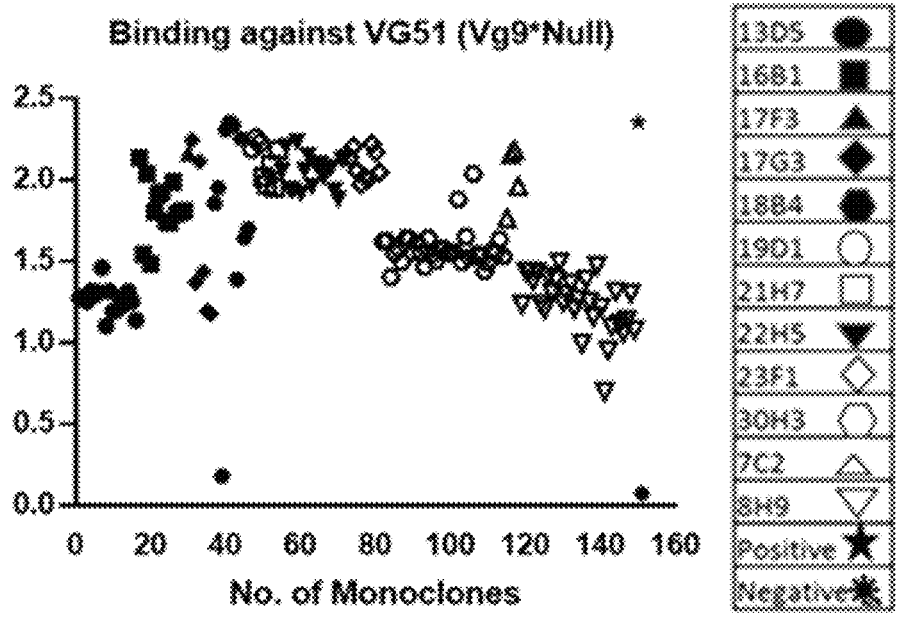
Figure 8C:
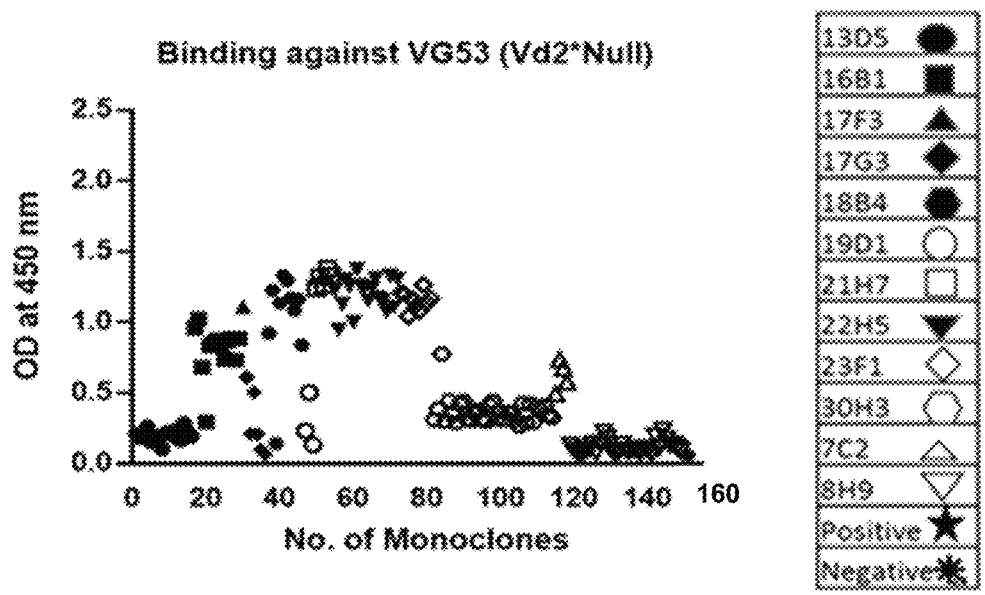
Figure 8D:
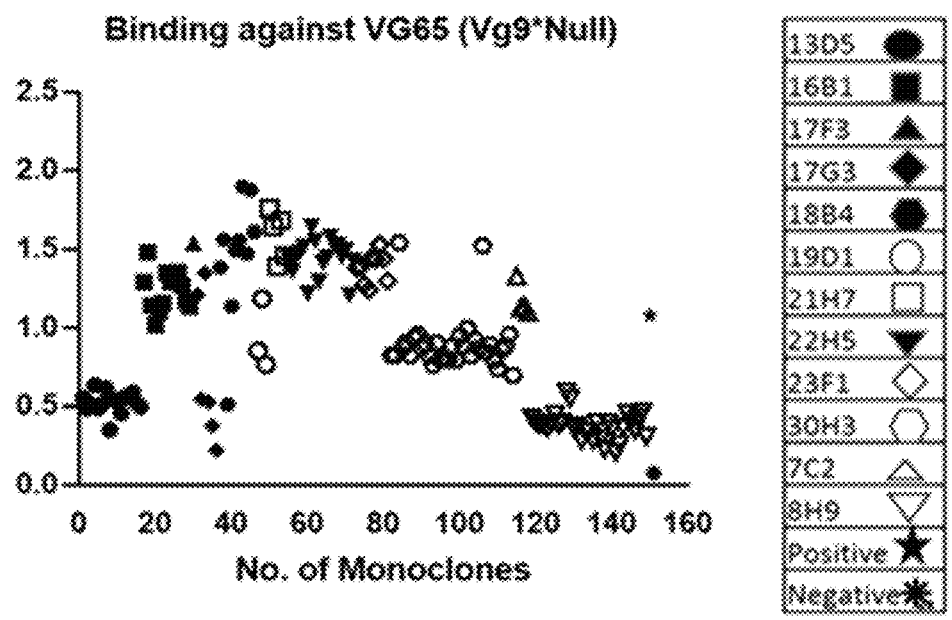
Figure 8E:
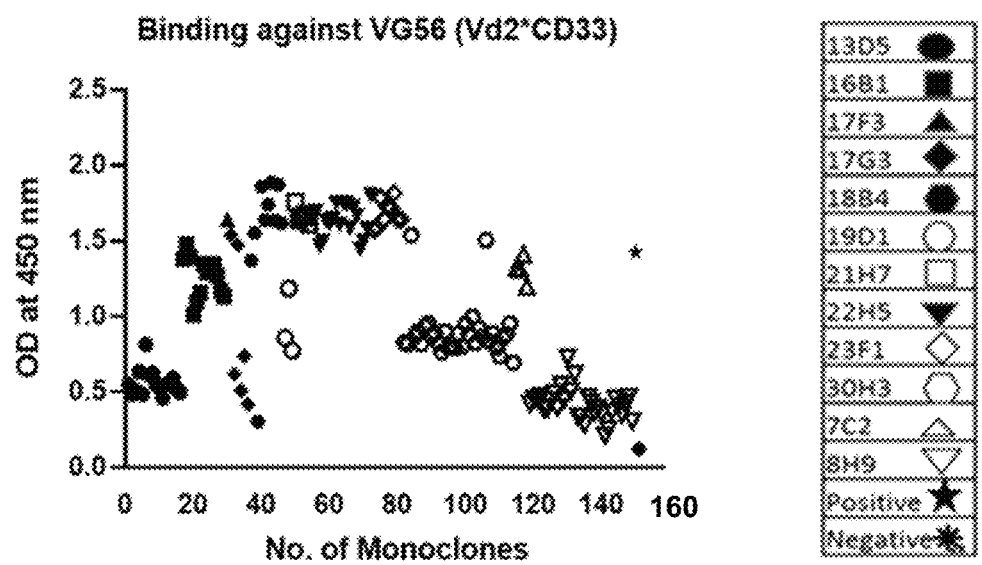
Figure 8F:
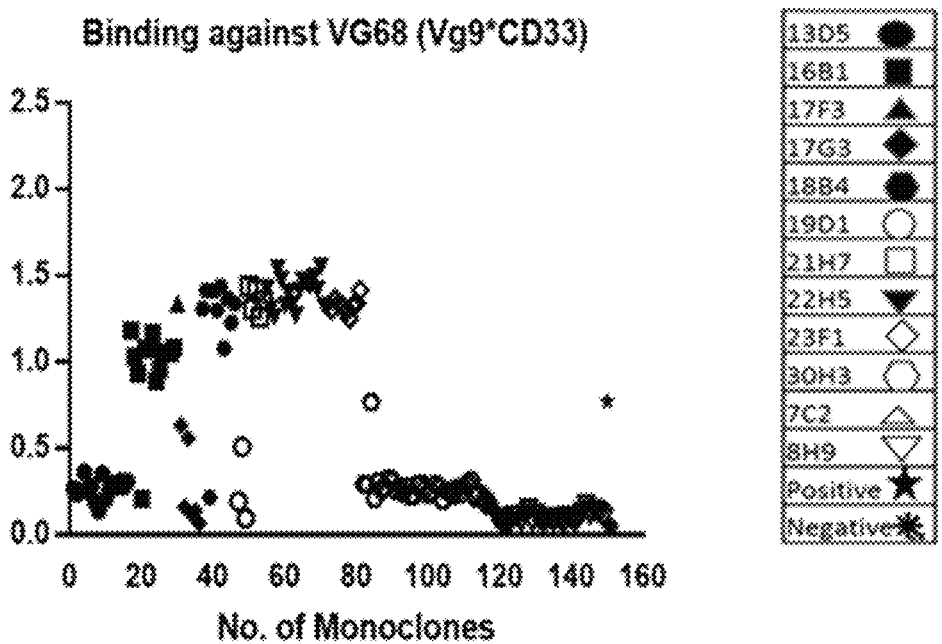
Figure 9A:
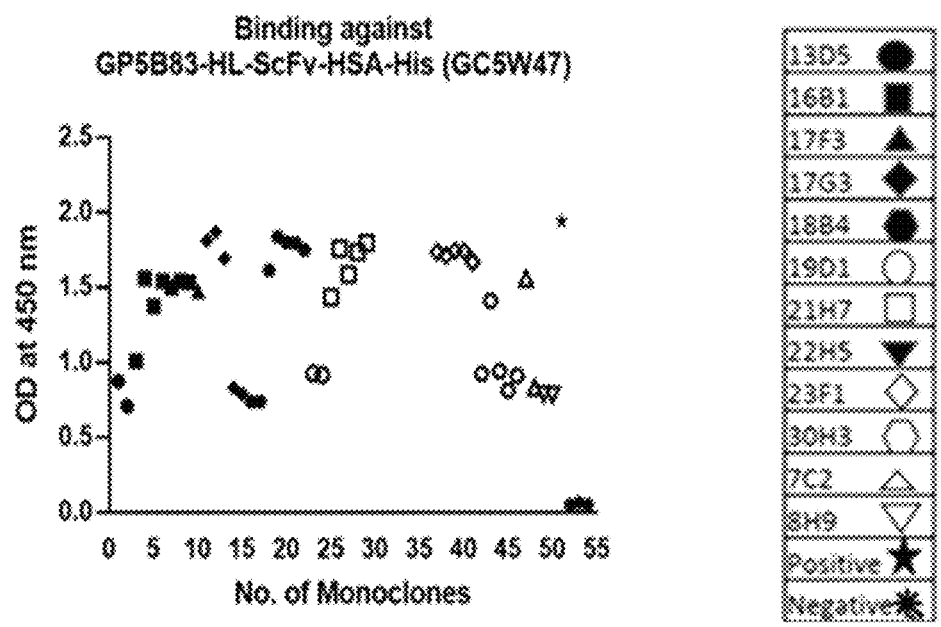
FIGS. 9A-9C demonstrate monoclone recognition of MSCD331 in different CAR-extra-cellular domain (ECD) constructs. For generation of these data, supernatants from 50 short-listed monoclone cultures were screened on his-tagged CAR-ECD proteins having different domain specificities, but expressing the same MSCD331 linker.
Figure 9B:
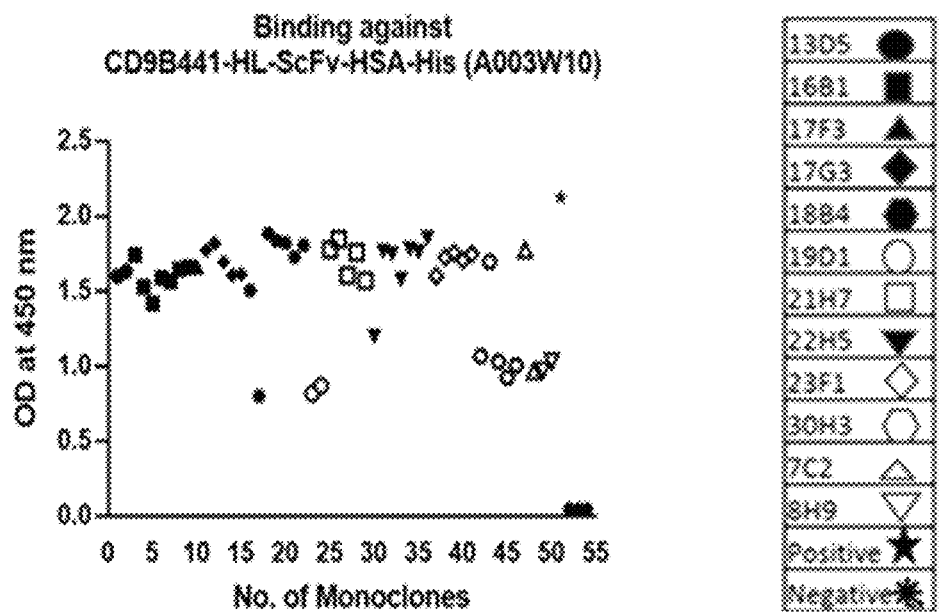
Figure 9C:
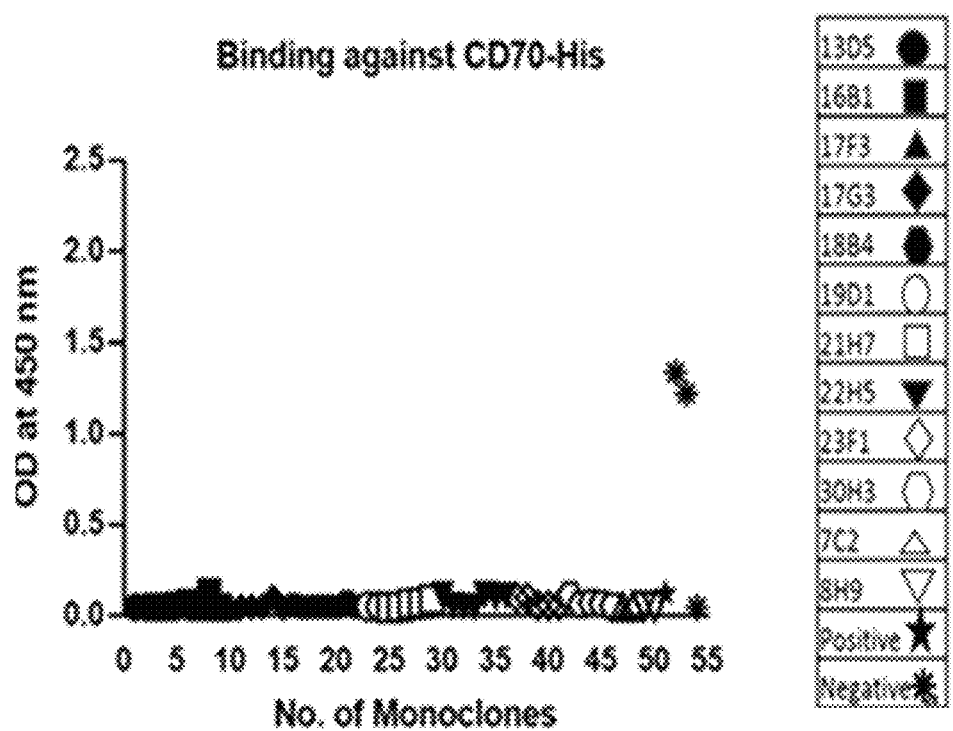

For screening of the monoclones by indirect ELISA, monoclones were screened by ELISA on plates coated with scFv-Fc fusion proteins, bispecific antibodies and CAR-ECD proteins. The antigens were coated at a concentration of 1 μg/ml in DPBS on to Nunc maxisorp plates (Nunc) and incubated overnight at 4° C. Plates were washed and blocked with 5% non-fat dry milk diluted in PBS and incubated for 1 hour at room temperature. Supernatants were incubated for 2 hours at 37° C. followed by addition of Goat anti-Mouse IgG HRP diluted in 1% BSA for 1 hour at room temperature. Plates were developed using TMB substrate and reaction stopped by adding 2N $H_2SO_4$. The absorbance (optical density, O.D.) was measured at 450 nm using a Spectrophotometer. FIGS. 7A-7B demonstrate monoclones specifically binding to MSCD331 but not to (G4S)4 linker (SEQ ID NO: 99) in an ELISA-based assay. To generate these data, supernatants from monoclone cultures were screened on scFv-Fc fusion proteins with either MSCD331 (FIG. 7A) or (G4S)4 linker (SEQ ID NO: 99) (FIG. 7B). FIGS. 8A-8F shows monoclone recognition of MSCD331 across different bispecific antibodies including VG52 (Vγ9*CD123), as shown in FIG. 8A; VG51 (Vγ9*Null), as shown in FIG. 8B; VG53 (Vδ2*Null), as shown in FIG. 8C; VG65 (Vγ9*Null), as shown in FIG. 8D; VG56 (Vδ2*CD33), as shown in FIG. 8E; and, VG68 (Vγ9*CD33), as shown in FIG. 8F. Notably, these bi-specific antibodies had MSCD331 linker bearing scFv (with different target specificities) either in both arms (FIGS. 8A-8B) or in one arm (FIGS. 8C-8F). It was further demonstrated in the present Example that monoclones were capable of recognizing MSCD331 in different CAR-ECD constructs, as shown in FIGS. 9A-9C. For generation of these data, supernatants from 50 short-listed monoclone cultures were screened on his-tagged CAR-ECD proteins having different domain specificities, but expressing the same MSCD331 linker. FIG. 9A and FIG. 9B show such data acquired via ELISA-based methods for binding against GP5B83-HL-scFv-HSA-His (GC5W47) and CD9B441-HL-ScFv-His (A003W10), respectively. An unrelated his tagged antigen, CD70 (CD70-His), was used for counter-screening, as shown in FIG. 9C.

Figure 5:
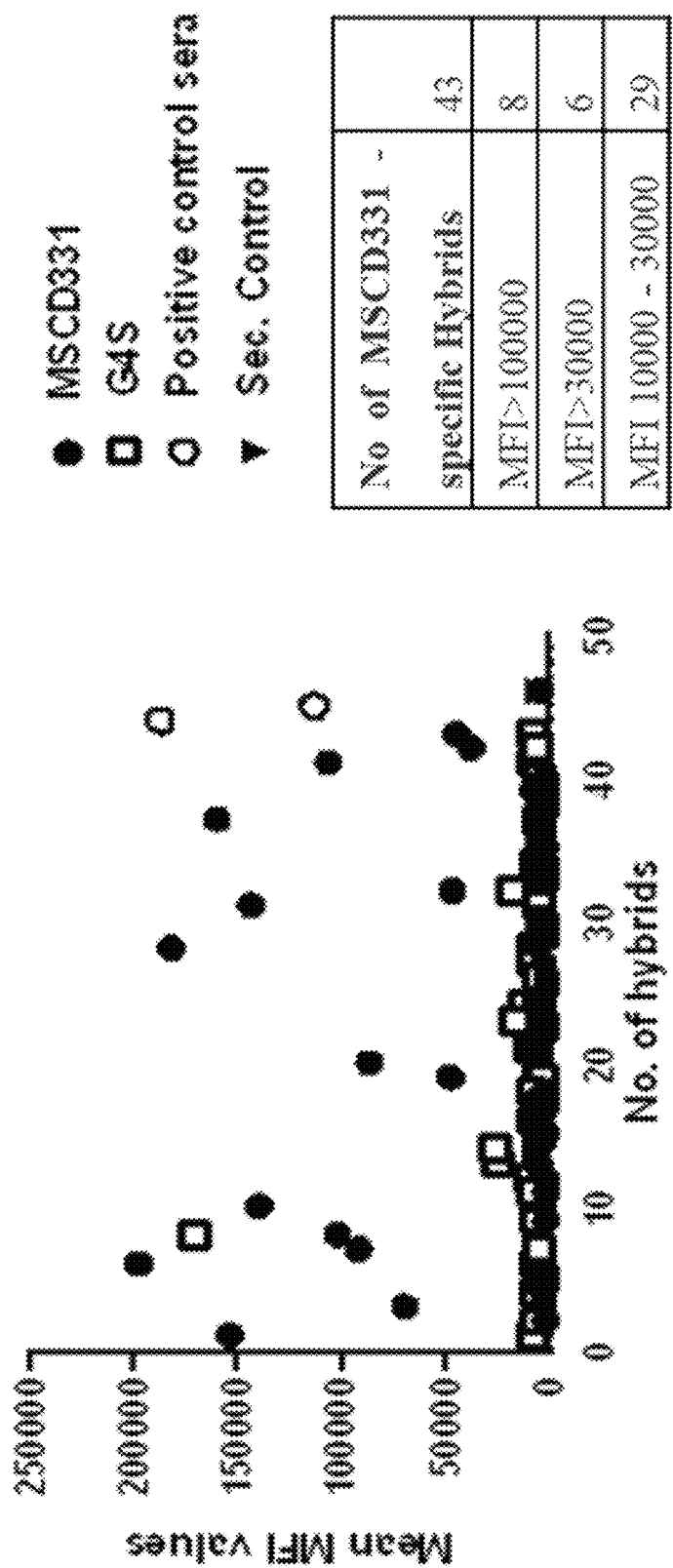
FIG. 5 demonstrates identification of hybrids that show MSCD331-specific binding using MSCD331- and (G4S)4 linker-bearing CD9B137-LH CAR ("(G4S)4 linker" disclosed as SEQ ID NO: 99) on the NS0 cell line. Supernatants from hybrid cultures were screened on NS0 cells expressing the CD9B137-LH CAR bearing either MSCD331 or (G4S)4 linker (SEQ ID NO: 99). Out of a total of 43 hybrids screened at the 6-well stage, 14 hybrids showed high-to-moderate MSCD331-specific binding. Specifically, as summarized in the table (inset), 8 MSCD331 hybrids possessed a mean fluorescence intensity (MFI) level of over 100,000 MFI (high MSCD331-specific binding), and 6 MSCD331 hybrids possessed a mean fluorescence intensity (MFI) level of over 30,000 MFI (moderate MSCD331-specific binding). Binding of MSCD331 specific sera (i.e., positive control sera) and secondary antibody alone control on the cell lines were also performed. Figure discloses "G4S" as SEQ ID NO: 100.
Figure 6A:
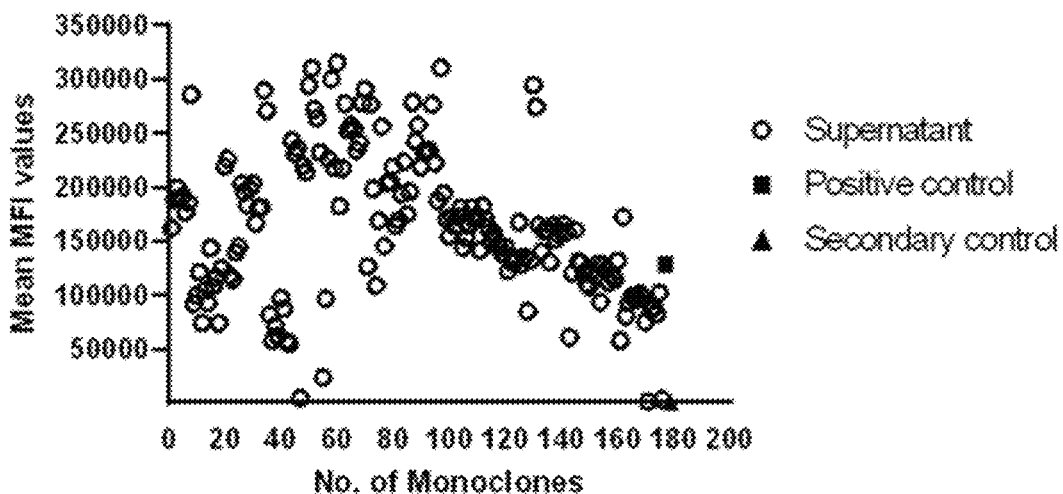
FIGS. 6A-6D demonstrate specificity and universality of binding of monoclones to MSCD331 assessed using CAR over-expressing NS0 and sup-T1 cell lines. Supernatants from monoclone cultures were screened on NS0 cells expressing the CD9B137-LH CAR bearing either MSCD331 (FIG. 6B) or (G4S)4 (FIG. 6D) linker (SEQ ID NO: 99), and on sup-T1 cells expressing human germline VH and VL chains bearing either MSCD331 (FIG. 6A) or (G4S)4 (FIG. 6C) linker (SEQ ID NO: 99). Binding of the MSCD331 specific sera (positive control) and secondary antibody alone (secondary control) to the cell lines are also indicated. Signal was measured as mean fluorescence intensity (MFI). Figure discloses "G4S" as SEQ ID NO: 100.
Figure 6B:
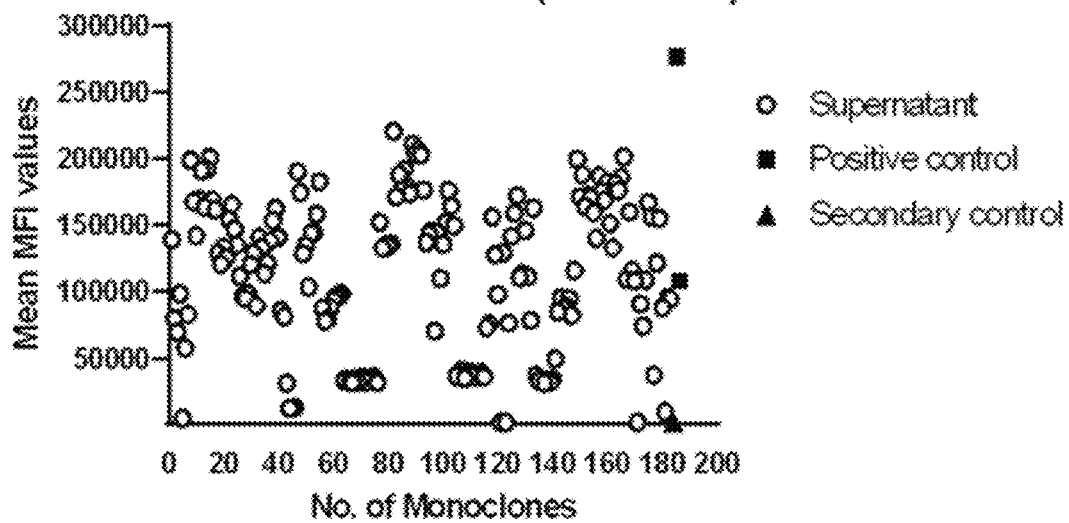
Figure 6C:
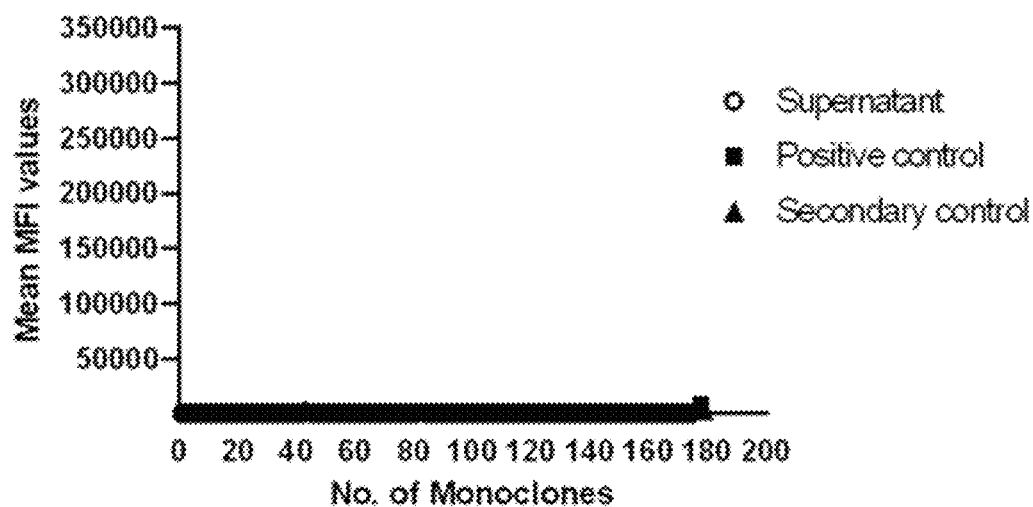
Figure 6D:
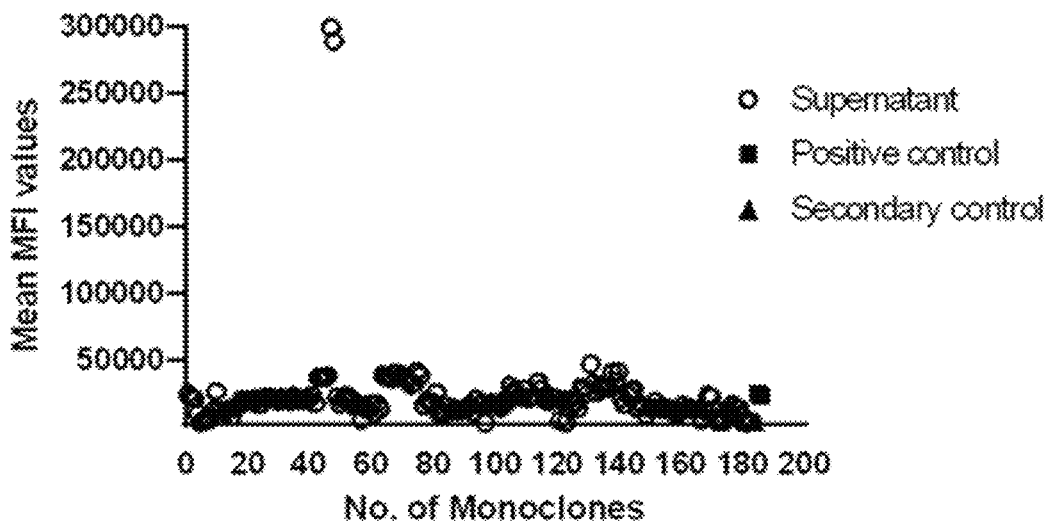

For binding of hybrid and monoclone supernatants to CAR expressing NS0 and sup-T1 cells, CAR expressing NS0 and sup-T1 cells were seeded into FACS plates (Grenier, 96 well U bottom plates) at a density of 0.1 million cells per well. Supernatants collected from the monoclones were incubated with the cell lines for 45 min at 4° C. Cells were washed with FACS buffer (PBS containing 2% FBS) and stained with Goat anti-Mouse IgG-PE (Southern Biotech) for 30 minutes at 4° C. The plates were washed and taken for acquisition on Acea Novocyte flow cytometer. FIG. 5 demonstrates identification of hybrids that show MSCD331-specific binding using MSCD331- and (G4S)4 linker-bearing CD9B137-LH CAR ("(G4S)4 linker" disclosed as SEQ ID NO: 99) on the NS0 cell line. Supernatants from hybrid cultures were screened on NS0 cells expressing the CD9B137-LH CAR bearing either MSCD331 or (G4S)4 linker (SEQ ID NO: 99). Out of a total of 43 hybrids screened at the 6-well stage, 14 hybrids showed high-to-moderate MSCD331-specific binding. Specifically, 8 MSCD331 hybrids possessed a mean fluorescence intensity (MFI) level of over 100,000 MFI (high MSCD331-specific binding), and 6 MSCD331 hybrids possessed a mean fluorescence intensity (MFI) level of over 30,000 MFI (moderate MSCD331-specific binding). Binding of MSCD331 specific sera (i.e., positive control sera) and secondary antibody alone control on the cell lines were also performed.

Monoclones exhibited specificity and universality of binding to MSCD331 assessed by using CAR over-expressing NS0 and sup-T1 cell lines, as shown in FIG. 6. Exemplar data were collected for supernatants from monoclone cultures screened on NS0 cells expressing the CD9B137-LH CAR bearing either MSCD331 (FIG. 6B) or (G4S)4 (FIG. 6D) linker (SEQ ID NO: 99), and on sup-T1 cells expressing human germline VH and VL bearing either MSCD331 (FIG. 6A) or (G4S)4 (FIG. 6C) linker (SEQ ID NO: 99).

Figure 10:
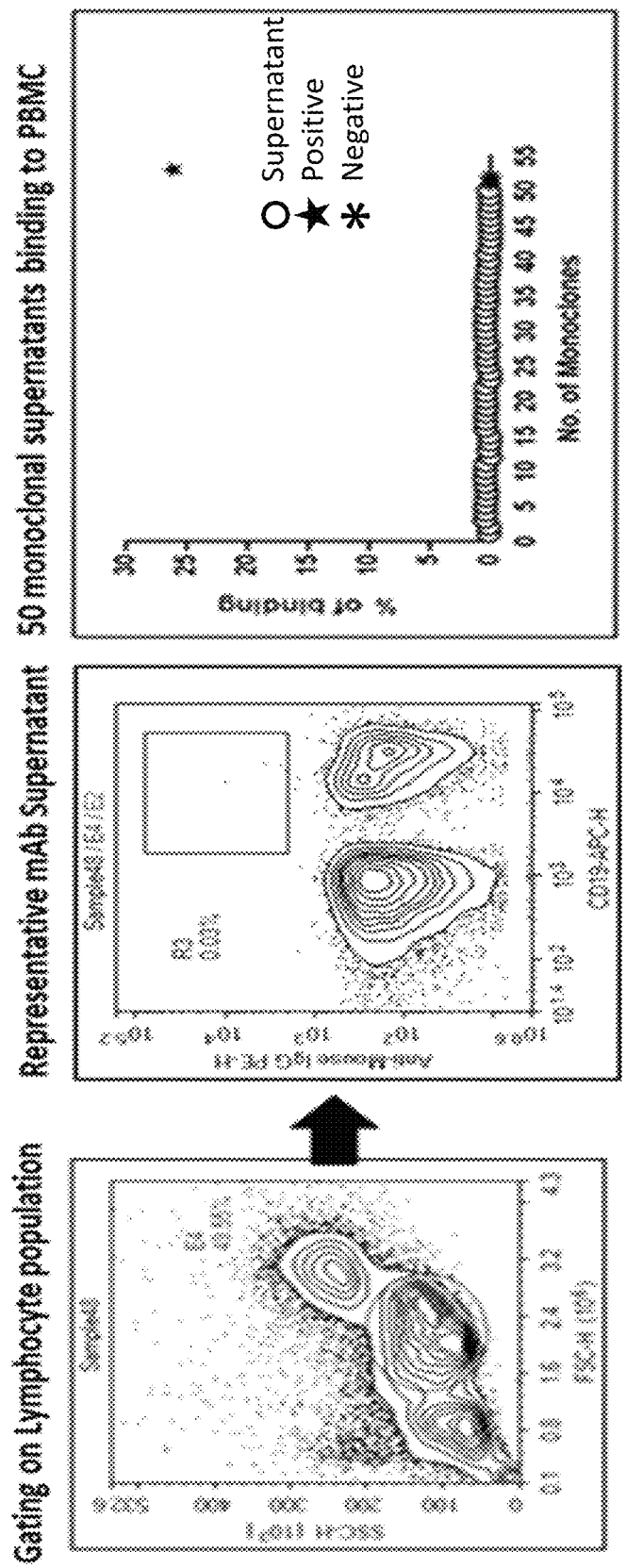
FIG. 10 demonstrates monoclones did not show non-specific binding. Supernatants from 50 short-listed monoclone cultures were incubated on human peripheral blood mononuclear cells (PBMCs) followed by anti-mouse IgG (phycoerythrin) PE. Scatter gated lymphocytes were checked for CD19-APC and anti-mouse IgG-PE double positive population to identify monoclonal antibody (mAb) binding to B cells. Binding of positive control and secondary antibody (negative) control on PBMCs are also shown.

To check for non-specific binding of the antibodies (monoclonal supernatants) to B-cell IgG, human PBMCs (peripheral blood mononuclear cells) were seeded at 0.75 million cells/100 µl in a U-bottom 96-well plate. Supernatants from 50 short-listed monoclones were incubated with the PBMCs for 45 min at 4° C., washed and stained with Goat anti-mouse IgG-PE and anti-human CD19-APC (Biolegend) for 30 minutes on ice. Data acquisition was performed using a Acea Novocyte flow cytometer. Flow cytometry results demonstrating monoclones do not show non-specific IgG binding are displayed in FIG. 10.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

```
                        SEQUENCE LISTING

Sequence total quantity: 100
SEQ ID NO: 1           moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 1
GITFRNYW                                                                    8

SEQ ID NO: 2           moltype = AA  length = 10
FEATURE                Location/Qualifiers
source                 1..10
                       mol_type = protein
                       organism = synthetic construct
                       note = Description of Artificial Sequence: Synthetic peptide
SEQUENCE: 2
IRLKSDYYAT                                                                 10

SEQ ID NO: 3           moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 3
TGFDWDDY                                                                    8

SEQ ID NO: 4           moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 4
GITFSNYW                                                                    8

SEQ ID NO: 5           moltype = AA  length = 10
FEATURE                Location/Qualifiers
source                 1..10
                       mol_type = protein
                       organism = synthetic construct
```

-continued

```
SEQUENCE: 5                note = Description of Artificial Sequence: Synthetic peptide
IRMRSDNYAT                                                              10

SEQ ID NO: 6               moltype =    length =
SEQUENCE: 6
000

SEQ ID NO: 7               moltype = AA   length = 8
FEATURE                    Location/Qualifiers
source                     1..8
                           mol_type = protein
                           organism = synthetic construct
                           note = Description of Artificial Sequence: Synthetic peptide
SEQUENCE: 7
GYPFTRYW                                                                8

SEQ ID NO: 8               moltype = AA   length = 8
FEATURE                    Location/Qualifiers
source                     1..8
                           mol_type = protein
                           organism = synthetic construct
                           note = Description of Artificial Sequence: Synthetic peptide
SEQUENCE: 8
IHPSDSDT                                                                8

SEQ ID NO: 9               moltype = AA   length = 9
FEATURE                    Location/Qualifiers
source                     1..9
                           mol_type = protein
                           organism = synthetic construct
                           note = Description of Artificial Sequence: Synthetic peptide
SEQUENCE: 9
LTMPVEGDY                                                               9

SEQ ID NO: 10              moltype = AA   length = 8
FEATURE                    Location/Qualifiers
source                     1..8
                           mol_type = protein
                           organism = synthetic construct
                           note = Description of Artificial Sequence: Synthetic peptide
SEQUENCE: 10
GYTFTRYW                                                                8

SEQ ID NO: 11              moltype = AA   length = 8
FEATURE                    Location/Qualifiers
source                     1..8
                           mol_type = protein
                           organism = synthetic construct
                           note = Description of Artificial Sequence: Synthetic peptide
SEQUENCE: 11
GFNIKNTY                                                                8

SEQ ID NO: 12              moltype = AA   length = 8
FEATURE                    Location/Qualifiers
source                     1..8
                           mol_type = protein
                           organism = synthetic construct
                           note = Description of Artificial Sequence: Synthetic peptide
SEQUENCE: 12
IDPTNGNT                                                                8

SEQ ID NO: 13              moltype = AA   length = 12
FEATURE                    Location/Qualifiers
source                     1..12
                           mol_type = protein
                           organism = synthetic construct
                           note = Description of Artificial Sequence: Synthetic peptide
SEQUENCE: 13
AGLGSNYFYS DV                                                           12

SEQ ID NO: 14              moltype = AA   length = 8
FEATURE                    Location/Qualifiers
source                     1..8
                           mol_type = protein
                           organism = synthetic construct
                           note = Description of Artificial Sequence: Synthetic peptide
SEQUENCE: 14
IDPANGYT                                                                8
```

```
SEQ ID NO: 15            moltype = AA  length = 12
FEATURE                  Location/Qualifiers
source                   1..12
                         mol_type = protein
                         organism = synthetic construct
                         note = Description of Artificial Sequence: Synthetic peptide
SEQUENCE: 15
AAFSSYVGYF DV                                                          12

SEQ ID NO: 16            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 16
GYTFTDYY                                                                8

SEQ ID NO: 17            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 17
INPNHGGS                                                                8

SEQ ID NO: 18            moltype = AA  length = 15
FEATURE                  Location/Qualifiers
source                   1..15
                         mol_type = protein
                         organism = synthetic construct
                         note = Description of Artificial Sequence: Synthetic peptide
SEQUENCE: 18
ARIGIYHGDY GEFDY                                                       15

SEQ ID NO: 19            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 19
GYTFTSYW                                                                8

SEQ ID NO: 20            moltype = AA  length = 10
FEATURE                  Location/Qualifiers
source                   1..10
                         mol_type = protein
                         organism = synthetic construct
                         note = Description of Artificial Sequence: Synthetic peptide
SEQUENCE: 20
ASFITTVGDV                                                             10

SEQ ID NO: 21            moltype = AA  length = 117
FEATURE                  Location/Qualifiers
source                   1..117
                         mol_type = protein
                         organism = synthetic construct
                         note = Description of Artificial Sequence: Synthetic
                          polypeptide
SEQUENCE: 21
EVQLQESGGG LVQPGRSMKL SCVAAGITFR NYWMNWVRQS PERGLEWVGQ IRLKSDYYAT       60
HYAESVKGRF TISRDDSKRS VYLQMNNLRA EDTGIYYCTG FDWDDYWGQG TTLTVSS         117

SEQ ID NO: 22            moltype = DNA  length = 352
FEATURE                  Location/Qualifiers
source                   1..352
                         mol_type = other DNA
                         organism = synthetic construct
                         note = Description of Artificial Sequence: Synthetic
                          polynucleotide
SEQUENCE: 22
gaggtgcagc tgcaggagtc tggaggaggc ttggtgcaac ctggaagatc catgaaactc       60
tcctgtgttg ccgctggaat cactttcagg aactattgga tgaactgggt ccgccagtct      120
ccagagaggg ggcttgagtg ggttggtcaa attagattga atctgattat ttatgcaaca      180
cattatgcgg agtctgtgaa agggaggttc accatctcaa gagatgattc caaacgtagt      240
gtctacctgc aaatgaataa tttaagggct gaagacactg gaatttatta ctgcacaggc      300
```

```
tttgactggg acgactactg gggccaaggc accactctca cagtctcctc ag        352
```

SEQ ID NO: 23          moltype = AA   length = 117
FEATURE                Location/Qualifiers
source                 1..117
                       mol_type = protein
                       organism = synthetic construct
                       note = Description of Artificial Sequence: Synthetic
                         polypeptide
SEQUENCE: 23
```
EVQLQESGGG LVQPGGSMKL SCVASGITFS NYWMNWVRQS PEKGLEWVAQ IRMRSDNYAT  60
HYAESVKGRF TISRDDSKSS VYLQMNNLRA EDTGIYYCTG FDWDDYWGQG TTLTVSS    117
```

SEQ ID NO: 24          moltype = DNA   length = 352
FEATURE                Location/Qualifiers
source                 1..352
                       mol_type = other DNA
                       organism = synthetic construct
                       note = Description of Artificial Sequence: Synthetic
                         polynucleotide
SEQUENCE: 24
```
gaggtgcagc tgcaggagtc tgggggaggc ttggtgcaac ctggaggatc catgaaactc  60
tcctgtgttg cctctggaat cacttttcag aactactgga tgaactgggt ccgccagtct 120
ccagagaagg ggcttgagtg ggttgctcaa attagaatga gatctgataa ttatgcaaca 180
cattatgcga agtctgtgaa agggaggttt accatctcaa gagatgattc aaaagtagt  240
gtctacctgc aaatgaacaa cttaagggct gaagacactg gaatttatta ctgcacaggc 300
tttgactggg acgactactg gggccaaggc accactctca cagtctcctc ag        352
```

SEQ ID NO: 25          moltype = AA   length = 116
FEATURE                Location/Qualifiers
source                 1..116
                       mol_type = protein
                       organism = synthetic construct
                       note = Description of Artificial Sequence: Synthetic
                         polypeptide
SEQUENCE: 25
```
EVQMQESGAE LVKPGASVKV SCKASGYPFT RYWMHWVKHR PGQGLEWIGR IHPSDSDTNY  60
NQNFKGKATL TVDRSSNTAY MQISSLTSED SAVYYCLTMP VEGDYWGQGT TLTVSS    116
```

SEQ ID NO: 26          moltype = DNA   length = 349
FEATURE                Location/Qualifiers
source                 1..349
                       mol_type = other DNA
                       organism = synthetic construct
                       note = Description of Artificial Sequence: Synthetic
                         polynucleotide
SEQUENCE: 26
```
gaggtgcaga tgcaggagtc tggggctgaa ctggtgaagc ctggggcttc agtgaaggtg  60
tcctgcaagg cttctggcta tcccttcacc aggtactgga tgcactgggt gaagcacagg 120
cctggccaag gccttgagtg gattggaagg attcatcctt ctgatagtga tactaactac 180
aatcaaaact tcaagggcaa ggccacgttg actgtagaca gatcctccaa cacagcctac 240
atgcagatca gcagcctgac atctgaggac tctgcggtct attactgttt aaccatgccc 300
gtggaggtg actactgggg ccaaggcacc actctcacag tctcctcag              349
```

SEQ ID NO: 27          moltype = AA   length = 116
FEATURE                Location/Qualifiers
source                 1..116
                       mol_type = protein
                       organism = synthetic construct
                       note = Description of Artificial Sequence: Synthetic
                         polypeptide
SEQUENCE: 27
```
EVQLQEYRAE LVKPGASVKV SCKASGYPFT RYWMHWVKHR PGQGLEWIGR IHPSDSDTNY  60
NQNFKGKATL TVDRSSNTAY MQLSSLTSED SAVYYCLTMP VEGDYWGQGT TLTVSS    116
```

SEQ ID NO: 28          moltype = DNA   length = 349
FEATURE                Location/Qualifiers
source                 1..349
                       mol_type = other DNA
                       organism = synthetic construct
                       note = Description of Artificial Sequence: Synthetic
                         polynucleotide
SEQUENCE: 28
```
gaggtgcagc tgcaggagta tagggctgaa ctggtgaagc ctggggcttc agtgaaggtg  60
tcctgcaagg cttctggcta tcccttcacc aggtactgga tgcactgggt gaagcacagg 120
cctggccaag gccttgagtg gattggaagg attcatcctt ctgatagtga tactaactac 180
aatcaaaact tcaagggcaa ggccacgttg actgtagaca gatcctccaa cacagcctac 240
atgcagctca gcagcctgac atctgaggac tctgcggtct attactgttt aaccatgccc 300
gtggaggtg actactgggg ccaaggcacc actctcacag tctcctcag              349
```

```
SEQ ID NO: 29          moltype = AA  length = 116
FEATURE                Location/Qualifiers
source                 1..116
                       mol_type = protein
                       organism = synthetic construct
                       note = Description of Artificial Sequence: Synthetic
                         polypeptide
SEQUENCE: 29
EVQLQESGAE LVKPGASVKV SCKASGYPFT RYWMHWVKHR PGQGLEWIGR IHPSDSDTNY    60
NQNFKGKATL TVDRSSNTAY MQLSSLTSED SAVYYCLTMP VEGDYWGQGT TLTVSS       116

SEQ ID NO: 30          moltype = DNA  length = 349
FEATURE                Location/Qualifiers
source                 1..349
                       mol_type = other DNA
                       organism = synthetic construct
                       note = Description of Artificial Sequence: Synthetic
                         polynucleotide
SEQUENCE: 30
gaggtgcagc tgcaggagtc tggggctgaa ctggtgaagc ctggggcttc agtgaaggtg    60
tcctgcaagg cttctggcta tcccttcacc aggtactgga tgcactgggt gaagcacagg   120
cctggccaag gccttgagtg gattggaagg attcatcctt ctgatagtga tactaactac   180
aatcaaaact tcaagggcaa ggccacgttg actgtagaca gatcctccaa cacagcctac   240
atgcagctca gcagcctgac atctgaggac tctgcggtct attactgttt aaccatgccc   300
gtggagggtg actactgggg ccaaggcacc actctcacag tctcctcag               349

SEQ ID NO: 31          moltype = AA  length = 116
FEATURE                Location/Qualifiers
source                 1..116
                       mol_type = protein
                       organism = synthetic construct
                       note = Description of Artificial Sequence: Synthetic
                         polypeptide
SEQUENCE: 31
EVQLQESGAE LVKPGASVKV SCKASGYPFT RYWMHWVKHR PGQGLEWIGR IHPSDSDTNY    60
NQKFKDKATL TVDRSSNTAY MQLSRLTSED SAVYYCLTMP VEGDYWGQGT TLTVSS       116

SEQ ID NO: 32          moltype = DNA  length = 349
FEATURE                Location/Qualifiers
source                 1..349
                       mol_type = other DNA
                       organism = synthetic construct
                       note = Description of Artificial Sequence: Synthetic
                         polynucleotide
SEQUENCE: 32
gaggtgcagc tgcaggagtc tggggctgaa ctggtgaagc ctggggcttc agtgaaggtg    60
tcctgcaagg cttctggcta tcccttcacc aggtactgga tgcactgggt gaagcacagg   120
cctggccaag gccttgagtg gattggaagg attcatcctt ctgatagtga tactaactac   180
aatcaaaaat tcaaggacaa ggccacgttg actgtagaca gatcctccaa cacagcctac   240
atgcagctca gcaggctgac atctgaggac tctgcggtct attactgttt aaccatgccc   300
gtggagggtg actactgggg ccaaggcacc actctcacag tctcctcag               349

SEQ ID NO: 33          moltype = AA  length = 116
FEATURE                Location/Qualifiers
source                 1..116
                       mol_type = protein
                       organism = synthetic construct
                       note = Description of Artificial Sequence: Synthetic
                         polypeptide
SEQUENCE: 33
EVQLQESGAE LVKPGASVKV SCKASGYTFT RYWMHWVKHR PGQGLEWIGR IHPSDSDTNY    60
NQKFKDKATL TVDRSSNTAY MQLSRLTSED SAVYYCLTMP VEGDYWGQGT TLTVSS       116

SEQ ID NO: 34          moltype = DNA  length = 349
FEATURE                Location/Qualifiers
source                 1..349
                       mol_type = other DNA
                       organism = synthetic construct
                       note = Description of Artificial Sequence: Synthetic
                         polynucleotide
SEQUENCE: 34
gaggtgcagc tgcaggagtc tggggctgaa ctggtgaagc ctggggcttc agtgaaggtg    60
tcctgcaagg cttctggcta taccttcacc aggtactgga tgcactgggt gaagcacagg   120
cctggccaag gccttgagtg gattggaagg attcatcctt ctgatagtga tactaactac   180
aatcaaaaat tcaaggacaa ggccacgttg actgtagaca gatcctccaa cacagcctac   240
atgcagctca gcaggctgac atctgaggac tctgcggtct attactgttt aaccatgccc   300
gtggagggtg actactgggg ccaaggcacc actctcacag tctcctcag               349
```

```
SEQ ID NO: 35              moltype = AA   length = 116
FEATURE                    Location/Qualifiers
source                     1..116
                           mol_type = protein
                           organism = synthetic construct
                           note = Description of Artificial Sequence: Synthetic
                             polypeptide
SEQUENCE: 35
EVQLQESGAE LVKPGASVKV SCKASGYTFT RYWMHWVKHR PGQGLEWIGR IHPSDSDTNY    60
NQKFKDKATL TVDRSSNTAY MQLSRLTSED YAVYYCLTMP VEGDYWGQGT TLTVSS       116

SEQ ID NO: 36              moltype = DNA   length = 349
FEATURE                    Location/Qualifiers
source                     1..349
                           mol_type = other DNA
                           organism = synthetic construct
                           note = Description of Artificial Sequence: Synthetic
                             polynucleotide
SEQUENCE: 36
gaggtgcagt tgcaggagtc tggggctgaa ctggtgaagc ctggggcttc agtgaaggtg    60
tcctgcaagg cttctggcta taccttcacc aggtactgga tgcactgggt gaagcacagg   120
cctggccaag gccttgagtg gattggaagg attcatcctt ctgatagtga tactaactac   180
aatcaaaaat tcaaggacaa ggccacgttg actgtagaca gatcctccaa cacagcctac   240
atgcagctca gcaggctgac atctgaggac tatgcggtct attactgttt aaccatgccc   300
gtggagggtg actactgggg ccaaggcacc actctcacag tctcctcag              349

SEQ ID NO: 37              moltype = AA   length = 116
FEATURE                    Location/Qualifiers
source                     1..116
                           mol_type = protein
                           organism = synthetic construct
                           note = Description of Artificial Sequence: Synthetic
                             polypeptide
SEQUENCE: 37
EVQLQESGAE LVKAGASVKV SCKASGYTFT RYWMHWVKHR PGQGLEWIGR IHPSDSDTNY    60
NQKFKGKATL TVDRSSNTAY MQLSSLTSED SAVYYCLTMP VEGDYWGQGT TLTVSS       116

SEQ ID NO: 38              moltype = DNA   length = 349
FEATURE                    Location/Qualifiers
source                     1..349
                           mol_type = other DNA
                           organism = synthetic construct
                           note = Description of Artificial Sequence: Synthetic
                             polynucleotide
SEQUENCE: 38
gaggtgcagc tgcaggagtc tggggctgaa ctggtgaagg ctggggcttc agtgaaggtg    60
tcctgcaagg cttctggcta taccttcacc aggtactgga tgcactgggt gaagcacagg   120
cctggccaag gccttgagtg gattggaagg attcatcctt ctgacagtga tactaactac   180
aatcaaaagt tcaagggcaa ggccacgttg actgtagaca gatcctccaa cacagcctac   240
atgcagctca gcagcctgac atctgaggac tctgcggtct attactgttt aaccatgccc   300
gtggagggtg actactgggg ccaaggcacc actctcacag tctcctcag              349

SEQ ID NO: 39              moltype = AA   length = 116
FEATURE                    Location/Qualifiers
source                     1..116
                           mol_type = protein
                           organism = synthetic construct
                           note = Description of Artificial Sequence: Synthetic
                             polypeptide
SEQUENCE: 39
EVQLQESGGE LVKAGASVKV SCKASGYTFT RYWMHWVKHR PGQGLEWIGR IHPSDSDTNY    60
NQKFKGKATL TVDRSSNTAY MQLSSLTSED CAVYYCLTMP VEGDYWGQGT TLTVSS       116

SEQ ID NO: 40              moltype = DNA   length = 349
FEATURE                    Location/Qualifiers
source                     1..349
                           mol_type = other DNA
                           organism = synthetic construct
                           note = Description of Artificial Sequence: Synthetic
                             polynucleotide
SEQUENCE: 40
gaggtgcagc tgcaggagtc tgggggtgaa ctggtgaagg ctggggcttc agtgaaggtg    60
tcctgcaagg cttctggcta taccttcacc aggtactgga tgcactgggt gaagcacagg   120
cctggccaag gccttgagtg gattggaagg attcatcctt ctgacagtga tactaactac   180
aatcaaaagt tcaagggcaa ggccacgttg actgtagaca gatcctccaa cacagcctac   240
atgcagctca gcagcctgac atctgaggac tgtgcggtct attactgttt aaccatgccc   300
gtggagggtg actactgggg ccaaggcacc actctcacag tctcctcag              349

SEQ ID NO: 41              moltype = AA   length = 119
```

```
FEATURE                 Location/Qualifiers
source                  1..119
                        mol_type = protein
                        organism = synthetic construct
                        note = Description of Artificial Sequence: Synthetic
                          polypeptide
SEQUENCE: 41
EVQLQESVAE LVRPGASVKL SCTASGFNIK NTYVHWVKLR PEQGLEWIGR IDPTNGNTKY    60
APKFQGKATI TADTSSNTAY LQLSSLTSED TAIYYCAGLG SNYFYSDVWG TGTTVTVSS    119

SEQ ID NO: 42           moltype = DNA   length = 358
FEATURE                 Location/Qualifiers
source                  1..358
                        mol_type = other DNA
                        organism = synthetic construct
                        note = Description of Artificial Sequence: Synthetic
                          polynucleotide
SEQUENCE: 42
gaggtgcagc tgcaggagtc tgtggcagag cttgtgaggc caggggcctc agtcaagttg    60
tcctgcacag cttctggctt caacattaaa aacacctatg tgcattgggt aaagctgagg   120
cctgaacagg gcctggagtg gattggaagg attgatccta cgaatggtaa tactaaatat   180
gccccgaagt tccagggcaa ggccactata actgcagaca catcctccaa cacagcctac   240
ctgcagctca gcagcctgac atctgaggac actgccatct attactgtgc tggtctcggt   300
agtaactact tttactccga tgtctggggc acagggacca cggtcaccgt ctcctcag    358

SEQ ID NO: 43           moltype = AA   length = 119
FEATURE                 Location/Qualifiers
source                  1..119
                        mol_type = protein
                        organism = synthetic construct
                        note = Description of Artificial Sequence: Synthetic
                          polypeptide
SEQUENCE: 43
EVQLQESVAE LVRPGASVKL SCTASGFNIK NTYMHWVKQR PEQGLEWIGR IDPANGYTIY    60
APKFQGKATI TADTSSNTAY LLLSSLTSED TAIYYCAAFS SYVGYFDVWG TGTTVTVSS    119

SEQ ID NO: 44           moltype = DNA   length = 358
FEATURE                 Location/Qualifiers
source                  1..358
                        mol_type = other DNA
                        organism = synthetic construct
                        note = Description of Artificial Sequence: Synthetic
                          polynucleotide
SEQUENCE: 44
gaggtgcagc tgcaggagtc tgtggcagag cttgtgaggc caggggcctc agtcaagttg    60
tcctgcacag cttctggctt caacattaaa aacacctata tgcactgggt gaaacagagg   120
cctgaacagg gcctggagtg gattggaagg attgatcctg cgaatggtta tactatatat   180
gccccgaagt tccagggcaa ggccactata actgcagaca catcctccaa cacagcctac   240
ctgctgctca gcagcctgac atctgaggac actgccatct attactgtgc tgcttttagt   300
agctacgtag gatacttcga tgtctggggc acagggacca cggtcaccgt ctcctcag    358

SEQ ID NO: 45           moltype = AA   length = 122
FEATURE                 Location/Qualifiers
source                  1..122
                        mol_type = protein
                        organism = synthetic construct
                        note = Description of Artificial Sequence: Synthetic
                          polypeptide
SEQUENCE: 45
EVQLQESGPE LVKPGASVKI SCKASGYTFT DYYMNWVKQS HGKSLEWIGD INPNHGGSSY    60
NQKFKGKATL TVDKSSSTAY MELRSLTSED SAVYYCARIG IYHGDYGEFD YWGQGTTLTV   120
SS                                                                  122

SEQ ID NO: 46           moltype = DNA   length = 367
FEATURE                 Location/Qualifiers
source                  1..367
                        mol_type = other DNA
                        organism = synthetic construct
                        note = Description of Artificial Sequence: Synthetic
                          polynucleotide
SEQUENCE: 46
gaggtgcagc tgcaggagtc tggacctgag ctgtgaagc tggggcttc agtgaagata    60
tcctgtaagg cttctggata cacgttcact gactactaca tgaactgggt gaagcagagc   120
catgggaaga gccttgagtg gattggagat attaatccta accatggtgg tagtagttac   180
aaccagaagt tcaagggcaa ggccacattg actgtagaca gtcctccag cacagcctac   240
atggagctcc gcagcctgac atctgaggac tctgcagtct attactgtgc aaggatatggg   300
atctaccatg gtgactacgg ggagtttgac tactggggcc aaggcaccac tctcacagtc   360
tcctcag                                                             367
```

```
SEQ ID NO: 47            moltype = AA   length = 117
FEATURE                  Location/Qualifiers
source                   1..117
                         mol_type = protein
                         organism = synthetic construct
                         note = Description of Artificial Sequence: Synthetic
                          polypeptide
SEQUENCE: 47
EVQLQESGAE LVKPGASVKV SCKASGYTFT SYWMHWVQR  PGQGLEWIGR IHPSDSDTNY   60
NQKFKGKATL TVDKSSSTAY MQLSSLTSED SAVYYCASFI TTVGDVWGTG TTVTVSS     117

SEQ ID NO: 48            moltype = DNA  length = 352
FEATURE                  Location/Qualifiers
source                   1..352
                         mol_type = other DNA
                         organism = synthetic construct
                         note = Description of Artificial Sequence: Synthetic
                          polynucleotide
SEQUENCE: 48
gaggtgcagc tgcaggagtc tggggctgaa ctggtgaagc ctggggcttc agtgaaggtg   60
tcctgcaagg cttctggcta caccttcacc agctactgga tgcactgggt aaagcagagg  120
cctggccaag gccttgagtg gattggaagg attcatcctt ctgatagtga tactaactac  180
aatcaaaagt tcaagggcaa ggccacattg actgtagaca atcctccag  cacagcctac  240
atgcagctca gcagcctgac atctgaggac tctgcggtct attactgtgc ctcatttatt  300
actacggtag gggatgtctg gggcacaggg accacggtca ccgtctcctc ag          352

SEQ ID NO: 49            moltype = AA   length = 11
FEATURE                  Location/Qualifiers
source                   1..11
                         mol_type = protein
                         organism = synthetic construct
                         note = Description of Artificial Sequence: Synthetic peptide
SEQUENCE: 49
QSLLDSDGKT Y                                                        11

SEQ ID NO: 50            moltype =      length =
SEQUENCE: 50
000

SEQ ID NO: 51            moltype = AA   length = 9
FEATURE                  Location/Qualifiers
source                   1..9
                         mol_type = protein
                         organism = synthetic construct
                         note = Description of Artificial Sequence: Synthetic peptide
SEQUENCE: 51
WQGTHFPRT                                                            9

SEQ ID NO: 52            moltype = AA   length = 11
FEATURE                  Location/Qualifiers
source                   1..11
                         mol_type = protein
                         organism = synthetic construct
                         note = Description of Artificial Sequence: Synthetic peptide
SEQUENCE: 52
QSLLDSDGET Y                                                        11

SEQ ID NO: 53            moltype =      length =
SEQUENCE: 53
000

SEQ ID NO: 54            moltype = AA   length = 9
FEATURE                  Location/Qualifiers
source                   1..9
                         mol_type = protein
                         organism = synthetic construct
                         note = Description of Artificial Sequence: Synthetic peptide
SEQUENCE: 54
WQGTFFPRT                                                            9

SEQ ID NO: 55            moltype = AA   length = 6
FEATURE                  Location/Qualifiers
source                   1..6
                         mol_type = protein
                         organism = synthetic construct
                         note = Description of Artificial Sequence: Synthetic peptide
SEQUENCE: 55
ENIYSY                                                               6
```

| | | |
|---|---|---|
| SEQ ID NO: 56<br>SEQUENCE: 56<br>000 | moltype =   length = | |
| SEQ ID NO: 57<br>FEATURE<br>source | moltype = AA   length = 9<br>Location/Qualifiers<br>1..9<br>mol_type = protein<br>organism = synthetic construct<br>note = Description of Artificial Sequence: Synthetic peptide | |
| SEQUENCE: 57<br>WQGTHFPYT | | 9 |
| SEQ ID NO: 58<br>FEATURE<br>source | moltype = AA   length = 11<br>Location/Qualifiers<br>1..11<br>mol_type = protein<br>organism = synthetic construct<br>note = Description of Artificial Sequence: Synthetic peptide | |
| SEQUENCE: 58<br>QSLLETDGRT Y | | 11 |
| SEQ ID NO: 59<br>SEQUENCE: 59<br>000 | moltype =   length = | |
| SEQ ID NO: 60<br>FEATURE<br>source | moltype = AA   length = 9<br>Location/Qualifiers<br>1..9<br>mol_type = protein<br>organism = synthetic construct<br>note = Description of Artificial Sequence: Synthetic peptide | |
| SEQUENCE: 60<br>QHHYVTPPT | | 9 |
| SEQ ID NO: 61<br>FEATURE<br>source | moltype = AA   length = 11<br>Location/Qualifiers<br>1..11<br>mol_type = protein<br>organism = synthetic construct<br>note = Description of Artificial Sequence: Synthetic peptide | |
| SEQUENCE: 61<br>KSLLHSNGNT Y | | 11 |
| SEQ ID NO: 62<br>SEQUENCE: 62<br>000 | moltype =   length = | |
| SEQ ID NO: 63<br>FEATURE<br>source | moltype = AA   length = 9<br>Location/Qualifiers<br>1..9<br>mol_type = protein<br>organism = synthetic construct<br>note = Description of Artificial Sequence: Synthetic peptide | |
| SEQUENCE: 63<br>MQHLKYPFT | | 9 |
| SEQ ID NO: 64<br>FEATURE<br>source | moltype = AA   length = 6<br>Location/Qualifiers<br>1..6<br>mol_type = protein<br>organism = synthetic construct<br>note = Description of Artificial Sequence: Synthetic peptide | |
| SEQUENCE: 64<br>GNIHNY | | 6 |
| SEQ ID NO: 65<br>FEATURE<br>source | moltype = AA   length = 9<br>Location/Qualifiers<br>1..9<br>mol_type = protein<br>organism = synthetic construct<br>note = Description of Artificial Sequence: Synthetic peptide | |
| SEQUENCE: 65<br>QHFWNAPYT | | 9 |
| SEQ ID NO: 66<br>FEATURE<br>source | moltype = AA   length = 12<br>Location/Qualifiers<br>1..12<br>mol_type = protein | |

```
                        organism = synthetic construct
                        note = Description of Artificial Sequence: Synthetic peptide
SEQUENCE: 66
QSLLYSSNQK NY                                                            12

SEQ ID NO: 67           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 67
QQYYSYPPA                                                                9

SEQ ID NO: 68           moltype = AA   length = 112
FEATURE                 Location/Qualifiers
source                  1..112
                        mol_type = protein
                        organism = synthetic construct
                        note = Description of Artificial Sequence: Synthetic
                            polypeptide
SEQUENCE: 68
DIVMTQSPLT LSVTIGQPAS ISCKSSQSLL DSDGKTYLNW LLQRPGQSPK RLIYLVSKLD         60
SGVPDRFTGS GSGTDFTLKI SRVEAEDLGV YYCWQGTHFP RTFGGGTKLE IK                 112

SEQ ID NO: 69           moltype = DNA   length = 337
FEATURE                 Location/Qualifiers
source                  1..337
                        mol_type = other DNA
                        organism = synthetic construct
                        note = Description of Artificial Sequence: Synthetic
                            polynucleotide
SEQUENCE: 69
gacattgtga tgacccagtc tccactcact ttgtcggtta ccattggaca accagcctcc         60
atctcttgca agtcaagtca gagcctctta gatagtgatg gaaagacata tttgaattgg        120
ttgttacaga ggccaggcca gtctccaaag cgcctaatct atctggtgtc taaactggac        180
tctgagtcc ctgacaggtt cactggcagt ggatcaggga cagatttcac actgaaaatc         240
agcagagtgg aggctgagga tttgggagtt tattattgct ggcaaggtac acatttccct        300
cggacgttcg gtggaggcac caagctggaa atcaaac                                 337

SEQ ID NO: 70           moltype = AA   length = 112
FEATURE                 Location/Qualifiers
source                  1..112
                        mol_type = protein
                        organism = synthetic construct
                        note = Description of Artificial Sequence: Synthetic
                            polypeptide
SEQUENCE: 70
DIKMTQSPLT LSVTIGQPAS FSCKSSQSLL DSDGETYLNW LFQGPGQSPK RLIYLVSKLD         60
SRVPDRFTGS GSGTDFTLKI SRVEAEDLGV YYCWQGTFFP RTFGGGTKLE IK                 112

SEQ ID NO: 71           moltype = DNA   length = 337
FEATURE                 Location/Qualifiers
source                  1..337
                        mol_type = other DNA
                        organism = synthetic construct
                        note = Description of Artificial Sequence: Synthetic
                            polynucleotide
SEQUENCE: 71
gacatcaaga tgacccagtc tccactcact ttgtcggtta ccattggaca accagcctcc         60
ttctcttgca agtcaagtca gagcctctta gatagtgatg gagagacata tttgaattgg        120
ttattccagg ggccaggcca gtctccaaag cgcctaatct atctggtatc taaactggac        180
tctagagtcc ctgacaggtt cactggcagt ggatcaggga cagatttcac actgaaaatc        240
agcagagtgg aggctgagga tttgggagtt tattattgct ggcaaggtac atttttcct         300
cggacgttcg gtggaggcac caaactggaa atcaaac                                 337

SEQ ID NO: 72           moltype = AA   length = 112
FEATURE                 Location/Qualifiers
source                  1..112
                        mol_type = protein
                        organism = synthetic construct
                        note = Description of Artificial Sequence: Synthetic
                            polypeptide
SEQUENCE: 72
DIKMTQSPLT LSVTLGQPAS FSCKSSQSLL DSDGETYLNW LFQGPGQSPK RLIYQVSKLD         60
SRVPDRFTGS GSGTDFTLKI SRVEAEDLGV YYCWQGTFFP RTFGGGTKLE IK                 112

SEQ ID NO: 73           moltype = DNA   length = 337
FEATURE                 Location/Qualifiers
```

```
source                  1..337
                        mol_type = other DNA
                        organism = synthetic construct
                        note = Description of Artificial Sequence: Synthetic
                           polynucleotide
SEQUENCE: 73
gacatcaaga tgacccagtc tccactcact ttgtcggtta cccttggaca accagcctcc    60
ttctcttgca agtcaagtca gagcctctta gatagtgatg gagagacata tttgaattgg   120
ttgtttcagg ggccaggcca gtctccaaag cgcctaatct atcaggtgtc taaactggac   180
tctagagtcc ctgacaggtt cactggcagt ggatcaggga cagatttcac actgaaaatc   240
agcagagtgg aggctgagga tttgggagtt tattattgct ggcaaggtac atttttcct    300
cggacgttcg gtggaggcac caaactggaa atcaaac                            337

SEQ ID NO: 74           moltype = AA  length = 112
FEATURE                 Location/Qualifiers
source                  1..112
                        mol_type = protein
                        organism = synthetic construct
                        note = Description of Artificial Sequence: Synthetic
                           polypeptide
SEQUENCE: 74
DIKMTQSPLT LSVTIGQPAS ISCKSSQSLL DSDGKTYLNW LLQRPGQSPK RRIYLVSKLD    60
SGVPDRFTGS GSGTDFTLKI SRVEAEDLGL YYCWQGTHFP YTFGGGTKLE VK           112

SEQ ID NO: 75           moltype = DNA  length = 337
FEATURE                 Location/Qualifiers
source                  1..337
                        mol_type = other DNA
                        organism = synthetic construct
                        note = Description of Artificial Sequence: Synthetic
                           polynucleotide
SEQUENCE: 75
gacatcaaga tgacccagtc tccactcact tgtcggtta ccattggaca accagcctcc     60
atctcttgca agtcaagtca gagcctctta gatagtgatg gaaagacata tttgaattgg   120
ttgttacaga ggccaggcca gtctccaaag cgccgaatct atctggtgtc taaactggac   180
tctggagtcc ctgacaggtt cactggcagt ggatcaggga cagatttcac actgaaaatc   240
agcagagtgg aggctgagga tttgggactt tattattgct ggcaaggtac acattttccg   300
tacacgttcg gaggggggac caagctggaa gtaaaac                            337

SEQ ID NO: 76           moltype = AA  length = 112
FEATURE                 Location/Qualifiers
source                  1..112
                        mol_type = protein
                        organism = synthetic construct
                        note = Description of Artificial Sequence: Synthetic
                           polypeptide
SEQUENCE: 76
DIKMTQSPLT LSVSLGQPAS FSCKSSQSLL DSDGETYLNW LFQGPGQSPK RLIYQVSKLD    60
SRVPDRFTGS GSGTDFTLKI SRVEAEDLGV YYCWQGTFFP RTFGGGTKLE IE           112

SEQ ID NO: 77           moltype = DNA  length = 337
FEATURE                 Location/Qualifiers
source                  1..337
                        mol_type = other DNA
                        organism = synthetic construct
                        note = Description of Artificial Sequence: Synthetic
                           polynucleotide
SEQUENCE: 77
gacatcaaga tgacccagtc tccactcact ttgtcggttt cccttggaca accagcctcc    60
ttctcttgca agtcaagtca gagcctctta gatagtgatg gagagacata tttgaattgg   120
ttatttcagg ggccaggcca gtctccaaag cgcctaatct atcaggtgtc taaactggac   180
tctagagtcc ctgacaggtt cactggcagt ggatcaggga cagatttcac actgaaaatc   240
agcagagtgg aggctgagga tttgggagtt tattattgct ggcaaggtac atttttcct    300
cggacgttcg gtggaggcac caaactggaa atcgaac                            337

SEQ ID NO: 78           moltype = AA  length = 112
FEATURE                 Location/Qualifiers
source                  1..112
                        mol_type = protein
                        organism = synthetic construct
                        note = Description of Artificial Sequence: Synthetic
                           polypeptide
SEQUENCE: 78
DIKMTQTPLT LSVSLGQPAS FSCKSSQSLL DSDGETYLNW LFQGPGQSPK RLIYQVSKLD    60
SRVPDRFTGS GSGTDFTLKI SRVEAEDLGV YYCWQGTFFP RTFGGGTKLE IE           112

SEQ ID NO: 79           moltype = DNA  length = 337
FEATURE                 Location/Qualifiers
source                  1..337
```

```
                              mol_type = other DNA
                              organism = synthetic construct
                              note = Description of Artificial Sequence: Synthetic
                                 polynucleotide
SEQUENCE: 79
gacatcaaga tgacccaaac tccactcact tgtcggttt  cccttggaca accagcctcc  60
ttctcttgca agtcaagtca gagcctctta gatagtgatg gagagacata tttgaattgg 120
ttatttcagg ggccaggcca gtctccaaag cgcctaatct atcaggtgtc taaactggac 180
tctagagtcc ctgacaggtt cactggcagt ggatcaggga cagatttcac actgaaaatc 240
agcagagtgg aggctgagga tttgggagtt tattattgct ggcaaggtac attttttcct 300
cggacgttcg gtggaggcac caaactggaa atcgaac                          337

SEQ ID NO: 80              moltype = AA  length = 112
FEATURE                    Location/Qualifiers
source                     1..112
                              mol_type = protein
                              organism = synthetic construct
                              note = Description of Artificial Sequence: Synthetic
                                 polypeptide
SEQUENCE: 80
DIKMTQSPLT LSVTIGQPAS ISCKSSQSLL DSDGKTYLNW LLQRPGQSPK RLIYLVSRLD  60
SGVPDRFTGS GSGTDFTLKI SRVEAEDLGV YYCWQGTHFP YTFGGGTKLE IK         112

SEQ ID NO: 81              moltype = DNA  length = 337
FEATURE                    Location/Qualifiers
source                     1..337
                              mol_type = other DNA
                              organism = synthetic construct
                              note = Description of Artificial Sequence: Synthetic
                                 polynucleotide
SEQUENCE: 81
gacatcaaga tgacccagtc tccactcact ttgtcggtta ccattggaca gccagcctcc  60
atctcttgca agtcaagtca gagcctctta gatagtgatg gaaagacata tttgaattgg 120
ttattacaga ggccaggcca gtctccaaag cgcctaatct atctggtgtc tagactggac 180
tctggagtcc ctgacaggtt cactggcagt ggatcaggga cagatttcac actgaaaatc 240
agcagagtgg aggctgagga tttgggagtt tattattgct ggcaaggtac gcattttccg 300
tacacgttcg gaggggggac caagctggaa ataaaac                          337

SEQ ID NO: 82              moltype = AA  length = 107
FEATURE                    Location/Qualifiers
source                     1..107
                              mol_type = protein
                              organism = synthetic construct
                              note = Description of Artificial Sequence: Synthetic
                                 polypeptide
SEQUENCE: 82
DIQMTQSPAS LSVSVGETVT ITCRASENIY SYLAWYQQKQ GKSPQLLVYN AKTLAEGVPS  60
RFSGSGSGTQ FSLKINSLQP EDFGSYYCQH HYVTPPTFGG GTKLEIE               107

SEQ ID NO: 83              moltype = DNA  length = 322
FEATURE                    Location/Qualifiers
source                     1..322
                              mol_type = other DNA
                              organism = synthetic construct
                              note = Description of Artificial Sequence: Synthetic
                                 polynucleotide
SEQUENCE: 83
gacatccaga tgactcagtc tccagcctcc ctatctgtat ctgtgggaga aactgtcacc  60
atcacatgtc gagcaagtga gaatatttac agttatttag catggtatca gcagaaacag 120
ggaaaatctc ctcagctcct ggtctataat gcaaaaacct tagcagaagg tgtgccatca 180
aggttcagtg gcagtggatc aggcacacag ttttctctga agatcaacag cctgcagcct 240
gaagattttg ggagttatta ctgtcaacat cattatgtta ctcctccgac gttcggtgga 300
ggcaccaaac tggaaatcga ac                                          322

SEQ ID NO: 84              moltype = AA  length = 107
FEATURE                    Location/Qualifiers
source                     1..107
                              mol_type = protein
                              organism = synthetic construct
                              note = Description of Artificial Sequence: Synthetic
                                 polypeptide
SEQUENCE: 84
DIQMTQSPAS LSVSVGETVT ITCRASENIY SYLAWYQQKQ GKSPQLLVYN AKTLAEGVPS  60
RFSGSGSGTQ FSLKINSLQP EDFGSYYCQH HYVTPPTFGG GTKLEIK               107

SEQ ID NO: 85              moltype = DNA  length = 322
FEATURE                    Location/Qualifiers
source                     1..322
                              mol_type = other DNA
```

```
                            organism = synthetic construct
                            note = Description of Artificial Sequence: Synthetic
                              polynucleotide
SEQUENCE: 85
gacatccaga tgactcagtc tccagcctcc ctatctgtat ctgtgggaga aactgtcacc    60
atcacatgtc gagcaagtga gaatatttac agttatttag catggtatca gcagaaacag   120
ggaaaatctc ctcagctcct ggtctataat gcaaaaacct tagcagaagg tgtgccatca   180
aggttcagtg gcagtggatc aggcacacag ttttctctga agatcaacag cctgcagcct   240
gaagattttg gagttatta ctgtcaacat cattatgtta ctcctccgac gttcggtgga    300
ggcaccaagc tggaaatcaa ac                                            322

SEQ ID NO: 86               moltype = AA length = 112
FEATURE                     Location/Qualifiers
source                      1..112
                            mol_type = protein
                            organism = synthetic construct
                            note = Description of Artificial Sequence: Synthetic
                              polypeptide
SEQUENCE: 86
DIKMTQSPLT LSVTIGQPAS ISCKSSQSLL ETDGRTYLNW LFQRPGQSPK RLIYLVSKLD    60
SGVPDRFTGS GSGTDFTLKI SRVEAEDLGV YYCWQGTHFP RTFGGGTSLE IK           112

SEQ ID NO: 87               moltype = DNA length = 337
FEATURE                     Location/Qualifiers
source                      1..337
                            mol_type = other DNA
                            organism = synthetic construct
                            note = Description of Artificial Sequence: Synthetic
                              polynucleotide
SEQUENCE: 87
gacatcaaga tgacccagtc tccactcact ttgtcggtta ccattggaca accagcctcc    60
atctcttgca agtcaagtca gagcctctta gaaactgatg gaaggacata tttgaattgg   120
ttgtttcaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga cttgggagtt tattattgct ggcaaggtac acatttcct    300
cggacgttcg gtggaggcac cagcttggaa atcaaac                            337

SEQ ID NO: 88               moltype = AA length = 112
FEATURE                     Location/Qualifiers
source                      1..112
                            mol_type = protein
                            organism = synthetic construct
                            note = Description of Artificial Sequence: Synthetic
                              polypeptide
SEQUENCE: 88
DIVMTQAAPS VPVTPGESVS ISCRSSKSLL HSNGNTYLYW FLQRPGQSPQ LLIYRMSNLA    60
SGVPDRFSGS GSGTAFTLRI SRVEAEDVGV YYCMQHLKYP FTFGSGTKLE IK           112

SEQ ID NO: 89               moltype = DNA length = 337
FEATURE                     Location/Qualifiers
source                      1..337
                            mol_type = other DNA
                            organism = synthetic construct
                            note = Description of Artificial Sequence: Synthetic
                              polynucleotide
SEQUENCE: 89
gatattgtga tgactcaggc tgcaccctct gtacctgtca ctcctggaga gtcagtatcc    60
atctcctgca ggtctagtaa gagtctcctg catagtaatg caacactta cttgtattgg    120
ttcctgcaga ggccaggcca gtctcctcag ctcctgtat atcggatgtc aaccttgcc    180
tcaggagtcc cagacaggtt cagtggcagt gggtcaggaa ctgctttcac actgagaatc   240
agtagagtgg aggctgagga tgtgggtgtt tattactgta tgcaacatct aaatatcca    300
ttcacgttcg gctcggggac aaagttggaa ataaaac                            337

SEQ ID NO: 90               moltype = AA length = 112
FEATURE                     Location/Qualifiers
source                      1..112
                            mol_type = protein
                            organism = synthetic construct
                            note = Description of Artificial Sequence: Synthetic
                              polypeptide
SEQUENCE: 90
DIKMTQSPLT LSVTIGQPAS ISCKSSQSLL DSDGKTYLNW LLLRPGQSPK RLLYLVSKLD    60
SGVPDRFTGS GSGTDFTLKI SRVEAEDLGV YYCWQGTHFP RTFGGGTKLE IK           112

SEQ ID NO: 91               moltype = DNA length = 337
FEATURE                     Location/Qualifiers
source                      1..337
                            mol_type = other DNA
                            organism = synthetic construct
```

```
                    note = Description of Artificial Sequence: Synthetic
                        polynucleotide
SEQUENCE: 91
gacatcaaga tgacccagtc tccactcact ttgtcggtta ccattggaca accagcctcc    60
atatcttgca agtcaagtca gagcctctta gatagtgatg gaaagacata tttgaattgg   120
ttgttactaa ggccaggcca gtctccaaag cgcctactct atctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acatttctcct  300
cggacgttcg gtggaggcac caagctggaa atcaaac                            337

SEQ ID NO: 92           moltype = AA  length = 112
FEATURE                 Location/Qualifiers
source                  1..112
                        mol_type = protein
                        organism = synthetic construct
                        note = Description of Artificial Sequence: Synthetic
                            polypeptide
SEQUENCE: 92
DIKMTQSPLT LSVTIGQPAS ISCKSSQSLL DSDGKTYLNW LLQRPGQSPK RLIYLVSKLD    60
SGVPDRFTGS GSGTDFTLKI SRVEAEDLGV YYCWQGTHFP RTFGGGTKLE IK           112

SEQ ID NO: 93           moltype = DNA  length = 337
FEATURE                 Location/Qualifiers
source                  1..337
                        mol_type = other DNA
                        organism = synthetic construct
                        note = Description of Artificial Sequence: Synthetic
                            polynucleotide
SEQUENCE: 93
gacatcaaga tgacccagtc tccactcact ttgtcggtta ccattggaca accagcctcc    60
atctcttgca agtcaagtca gagcctctta gatagtgatg gaaagacata tttgaattgg   120
ttgttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acatttctcct  300
cggacgttcg gtggaggcac caagctggaa atcaaac                            337

SEQ ID NO: 94           moltype = AA  length = 107
FEATURE                 Location/Qualifiers
source                  1..107
                        mol_type = protein
                        organism = synthetic construct
                        note = Description of Artificial Sequence: Synthetic
                            polypeptide
SEQUENCE: 94
DIQMTQSPAS LSASVGETVT ITCRASGNIH NYLAWYQQKQ GKSPQLLVYN AKTLADGVPS    60
RFSGSGSGTQ FSLKINSLQP EDLGSYYCQH FWNAPYTFGG GTKLELK                 107

SEQ ID NO: 95           moltype = DNA  length = 322
FEATURE                 Location/Qualifiers
source                  1..322
                        mol_type = other DNA
                        organism = synthetic construct
                        note = Description of Artificial Sequence: Synthetic
                            polynucleotide
SEQUENCE: 95
gacatccaga tgactcagtc tccagcctcc ctatctgcat ctgtgggaga aactgtcacc    60
atcacatgtc gagcaagtgg gaatattcac aattatttag catggtatca gcagaaacag   120
ggaaaatctc ctcagctcct ggtctataat gcaaaaacct tagcagatgg tgtgccatct   180
aggttcagtg gcagtggatc aggaacacaa ttttctctca agatcaacag cctgcagcct   240
gaagatcttg ggagttatta ctgtcaacat ttttggaatg ctccgtacac gttcggaggg   300
gggaccaagc tggaattaaa ac                                            322

SEQ ID NO: 96           moltype = AA  length = 113
FEATURE                 Location/Qualifiers
source                  1..113
                        mol_type = protein
                        organism = synthetic construct
                        note = Description of Artificial Sequence: Synthetic
                            polypeptide
SEQUENCE: 96
DIKMTQSPSS LAVSVGEKVT MSCKSSQSLL YSSNQKNYLA WYQQKPGQSP KLLIYWASTR    60
ESGVPDRFTG SGSGTDFTLT ISSVKAEDLA VYYCQQYYSY PPAFGGGTKL EIK          113

SEQ ID NO: 97           moltype = DNA  length = 340
FEATURE                 Location/Qualifiers
source                  1..340
                        mol_type = other DNA
                        organism = synthetic construct
                        note = Description of Artificial Sequence: Synthetic
```

```
                        polynucleotide
SEQUENCE: 97
gacatcaaga tgacccagtc tccatcctcc ctagctgtgt cagttggaga gaaggttact    60
atgagctgca agtccagtca gagccttta tatagtagca atcaaaagaa ctacttggcc   120
tggtaccagc agaaaccagg gcagtctcct aaactgctga tttactgggc atccactagg   180
gaatctgggg tccctgatcg cttcacaggc agtggatctg ggacagattt cactctcacc   240
atcagcagtg tgaaggctga agacctggca gtttattact gtcagcaata ttatagctat   300
cctccggcgt tcggtggagg caccaagctg gaaatcaaac                         340

SEQ ID NO: 98           moltype = AA  length = 20
FEATURE                 Location/Qualifiers
source                  1..20
                        mol_type = protein
                        organism = synthetic construct
                        note = Description of Artificial Sequence: Synthetic peptide
SEQUENCE: 98
GGSEGKSSGS GSESKSTGGS                                                20

SEQ ID NO: 99           moltype = AA  length = 20
FEATURE                 Location/Qualifiers
source                  1..20
                        mol_type = protein
                        organism = synthetic construct
                        note = Description of Artificial Sequence: Synthetic peptide
SEQUENCE: 99
GGGGSGGGGS GGGGSGGGGS                                                20

SEQ ID NO: 100          moltype = AA  length = 5
FEATURE                 Location/Qualifiers
source                  1..5
                        mol_type = protein
                        organism = synthetic construct
SEQUENCE: 100
GGGGS                                                                 5
```

What is claimed is:

1. An isolated antibody, or antigen-binding fragment thereof, comprising
a heavy chain complementarity determining region 1 (CDR1), a heavy chain CDR2 and a heavy chain CDR3 of a heavy chain variable region (VH) comprising an amino acid sequence of SEQ ID NO: 29, and a light chain CDR1, a light chain CDR2 and a light chain CDR3 of a light chain variable region (VL) comprising an amino acid sequence of SEQ ID NO: 72.

2. The isolated antibody or antigen-binding fragment thereof of claim 1, wherein the isolated antibody or antigen-binding fragment thereof specifically binds to a linker peptide comprising the amino acid sequence of GGSEGKSSGSGSESKSTGGS (SEQ ID NO: 98).

3. The isolated antibody or antigen-binding fragment thereof of claim 1, wherein the isolated antibody or antigen-binding fragment thereof specifically binds to a linker peptide consisting of the amino acid sequence of GGSEGKSSGSGSESKSTGGS (SEQ ID NO: 98).

4. The isolated antibody or antigen-binding fragment thereof of claim 1, comprising
a heavy chain CDR1 comprising the amino acid sequence of SEQ ID NO: 7, a heavy chain CDR2 comprising the amino acid sequence of SEQ ID NO: 8, and a heavy chain CDR3 comprising the amino acid sequence of SEQ ID NO: 9.

5. The isolated antibody or antigen-binding fragment of claim 1, comprising
a light chain CDR1 comprising the amino acid sequence of SEQ ID NO: 52, a light chain CDR2 comprising the amino acid sequence of QVS, and a light chain CDR3 comprising the amino acid sequence of SEQ ID NO: 54.

6. The isolated antibody or antigen-binding fragment of claim 1, comprising a heavy chain CDR1 comprising the amino acid sequence of SEQ ID NO: 7, a heavy chain CDR2 comprising the amino acid sequence of SEQ ID NO: 8, a heavy chain CDR3 comprising the amino acid sequence of SEQ ID NO: 9, a light chain CDR1 comprising the amino acid sequence of SEQ ID NO: 52, a light chain CDR2 comprising the amino acid sequence of QVS, and a light chain CDR3 comprising the amino acid sequence of SEQ ID NO: 54.

7. The isolated antibody or antigen-binding fragment of claim 1, comprising
a VH comprising an amino acid sequence of SEQ ID NO: 29, and a VL comprising an amino acid sequence of SEQ ID NO: 72.

8. The isolated antibody or antigen-binding fragment of claim 1, wherein said antibody or antigen-binding fragment does not specifically bind to the amino acid sequence GGGGSGGGGSGGGGSGGGGS (SEQ ID NO: 99).

9. The isolated antibody or antigen-binding fragment of claim 1, wherein said antibody or antigen-binding fragment does not specifically bind to Immunoglobulin G (IgG).

10. The isolated antibody or antigen-binding fragment of claim 1, wherein the antibody or antigen-binding fragment is recombinant.

11. The isolated antibody or antigen-binding fragment of claim 1, wherein the antibody or antigen-binding fragment is a human antibody, a monoclonal antibody, a single chain antibody, a Fab, a Fab', a F(ab')2, a Fv, or a scFv.

12. The isolated antibody or antigen-binding fragment of claim 1, wherein the antibody or antigen-binding fragment is of IgG1, IgG2, IgG3, or IgG4 isotype.

13. A kit comprising (i) the isolated antibody or antigen-binding fragment of claim 1 and (ii) packaging for the same.

14. An affinity matrix comprising the isolated antibody or antigen-binding fragment of claim 1.

15. A method of detecting a polypeptide comprising a linker peptide comprising the amino acid sequence of GGSEGKSSGSGSESKSTGGS (SEQ ID NO: 98) in a sample, said method comprising (i) contacting the sample with the isolated antibody or antigen-binding fragment of claim 1, and (ii) detecting the binding of the polypeptide to said isolated antibody or antigen-binding fragment.

16. A method of measuring the amount of a polypeptide comprising a linker peptide comprising the amino acid sequence of GGSEGKSSGSGSESKSTGGS (SEQ ID NO: 98) in a sample, said method comprising (i) contacting the sample with the isolated antibody or antigen-binding fragment of claim 1, and (ii) quantitating the binding of the polypeptide to said isolated antibody or antigen-binding fragment.

\* \* \* \* \*

UNITED STATES PATENT AND TRADEMARK OFFICE
CERTIFICATE OF CORRECTION

| | | |
|---|---|---|
| PATENT NO. | : 12,129,310 B2 | Page 1 of 1 |
| APPLICATION NO. | : 18/122948 | |
| DATED | : October 29, 2024 | |
| INVENTOR(S) | : Sanjaya Singh et al. | |

It is certified that error appears in the above-identified patent and that said Letters Patent is hereby corrected as shown below:

On the Title Page

Item (54), and in the Specification Column 1 Lines 1-2, please change the title from "Materials and Methods for Enhanced Linker Targeting" to -- Antibody Binding to a Linker Peptide --.

Signed and Sealed this
Third Day of December, 2024

Katherine Kelly Vidal
*Director of the United States Patent and Trademark Office*